(12) United States Patent
Hasumi et al.

(10) Patent No.: US 8,207,203 B2
(45) Date of Patent: Jun. 26, 2012

(54) PYRIDYLISOXAZOLE DERIVATIVES

(75) Inventors: Koichi Hasumi, Kawasaki (JP); Shuji Ohta, Kawasaki (JP); Takahisa Saito, Kawasaki (JP); Shuichiro Sato, Kawasaki (JP); Jun-ya Kato, Kawasaki (JP); Jun Sato, Kawasaki (JP); Hiroyuki Suzuki, Kawasaki (JP); Hajime Asano, Kawasaki (JP); Mami Okada, Kawasaki (JP); Yasuhiro Matsumoto, Kawasaki (JP); Kazuhiko Shirota, Kawasaki (JP)

(73) Assignee: Aska Pharmaceutical Co., Ltd., Tokyo (JP)

( * ) Notice: Subject to any disclaimer, the term of this patent is extended or adjusted under 35 U.S.C. 154(b) by 596 days.

(21) Appl. No.: 12/308,875

(22) PCT Filed: Jun. 26, 2007

(86) PCT No.: PCT/JP2007/063207
§ 371 (c)(1),
(2), (4) Date: Dec. 24, 2008

(87) PCT Pub. No.: WO2008/001930
PCT Pub. Date: Jan. 3, 2008

(65) Prior Publication Data
US 2009/0306145 A1    Dec. 10, 2009

(30) Foreign Application Priority Data
Jun. 28, 2006    (JP) .................... 2006-177950

(51) Int. Cl.
*A61K 31/4439*    (2006.01)
*C07D 413/04*    (2006.01)

(52) U.S. Cl. ................... 514/340; 546/272.1
(58) Field of Classification Search ............ 546/272.1; 514/340
See application file for complete search history.

(56) References Cited

U.S. PATENT DOCUMENTS

| | | | |
|---|---|---|---|
| 5,633,272 A | 5/1997 | Talley et al. | |
| 5,656,664 A | 8/1997 | O'Lenick, Jr. | |
| 5,686,455 A | 11/1997 | Adams et al. | |
| 5,859,257 A | 1/1999 | Talley | |
| 5,916,891 A | 6/1999 | Adams et al. | |
| 5,985,902 A | 11/1999 | Talley et al. | |
| 6,268,370 B1 | 7/2001 | Adams et al. | |
| 6,423,713 B1 | 7/2002 | Anantanarayan et al. | |
| 6,511,997 B1 | 1/2003 | Minami et al. | |
| 6,514,977 B1 | 2/2003 | Anantanarayan et al. | |
| 6,525,059 B1 | 2/2003 | Anantanarayan et al. | |
| 6,617,324 B1 | 9/2003 | Naraian et al. | |
| 6,645,989 B2 | 11/2003 | Adams et al. | |
| 6,979,686 B1 | 12/2005 | Naraian et al. | |
| 7,071,198 B1 | 7/2006 | Naraian et al. | |
| 7,153,959 B2 | 12/2006 | Naraian et al. | |
| 2003/0064997 A1 | 4/2003 | Adams et al. | |
| 2004/0132755 A1 | 7/2004 | Ledeboer et al. | |
| 2004/0176433 A1 | 9/2004 | Naraian et al. | |
| 2006/0128759 A1 | 6/2006 | Laufer et al. | |
| 2007/0078146 A1 | 4/2007 | Naraian et al. | |

FOREIGN PATENT DOCUMENTS

| | | |
|---|---|---|
| JP | 2000-86657 | 3/2000 |
| JP | 2002-179656 | 6/2002 |
| WO | 93/14081 | 7/1993 |
| WO | 96/25405 | 8/1996 |
| WO | 98/52940 | 11/1998 |
| WO | 00/39116 | 7/2000 |
| WO | 2004/017968 | 3/2004 |
| WO | 2004/022555 | 3/2004 |
| WO | 2006/070927 | 7/2006 |

OTHER PUBLICATIONS

International Preliminary Report on Patentability and translation of PCT Written Opinion dated Jan. 29, 2009 for International (PCT) Application No. PCT/JP2007/063207 of which the present application is the U.S. National Stage.
Timothy F. Gallagher et al., "Regulation of Stress-Induced Cytokine Production by Pyridinylimidazoles; Inhibition of CSBP Kinase", Bioorganic & Medicinal Chemistry, vol. 5, No. 1, pp. 49-64, 1997.
Katerina Leftheris et al., "The Discovery of Orally Active Triaminotriazine Aniline Amides as Inhibitors of p38 MAP Kinase", J. Med. Chem., vol. 47, pp. 6283-6291, 2004.
English Abstract of JP 2000-86657 published Mar. 28, 2000.
International Search Report dated Jul. 31, 2007 in the International (PCT) Application PCT/JP2007/063207 of which the present application is the U.S. National Stage.

*Primary Examiner* — Patricia Morris
(74) *Attorney, Agent, or Firm* — Wenderoth, Lind & Ponack, L.L.P.

(57) ABSTRACT

This invention offers isoxazole derivatives represented by the following formula (I)

in which $R^1$ and $R^2$ each stands for hydrogen, lower alkyl, amino and the like; $R^3$ stands for substituted or unsubstituted aryl or hetero aryl; $R^4$ stands for hydrogen or lower alkyl; $R^5$ stands for substituted or unsubstituted phenyl, furyl and the like; and Y stands for —$CH_2$—, —CO—, —O—, —NH— and the like, or pharmaceutically acceptable salts thereof which exhibit excellent p38MAPkinase-inhibiting action with reduced side-effects, and are useful for treating such diseases as chronic rheumatoid arthritis, ulcerative colitis and the like.

10 Claims, No Drawings

PYRIDYLISOXAZOLE DERIVATIVES

TECHNICAL FIELD

This invention relates to novel pyridylisoxazole derivatives or salts thereof, methods of their preparation and their use. Compounds of this invention exhibit p38MAPkinase inhibiting action and in consequence inhibitory action to the production of tumor necrosis factor-α (TNF-α), interleukin-1 (IL-1), interleukin-6 (IL-6), interleukin-8 (IL-8), cyclooxygenase-II (COX-II) and the like. They are, therefore, useful as the treating agent of TNF-α-related diseases, IL-1-related diseases, IL-6-related diseases, IL-8-related diseases and COX-II-related diseases and the like.

BACKGROUND ART

TNF-α, IL-1, IL-6, IL-8 and COX-II are mainly the proteins (cytokines) produced by immunocompetent cells such as macrophage and neutrophil, which are known as one of the important factors participating in, besides immunomodulatory function and inflammatory symptoms, the hematopoietic system, endocrine system, nervous system and the like.

On the other hand, p38MAPkinase has the action of activating transcription factors such as NF-κB, AP-1 and CREB. These transcription factors bind to the DNA sequence common among TNF-α, IL-1, IL-6, IL-8, COX-II and the like to promote transcription of mRNA which synthesizes the respective cytokines. p38MAPkinase, therefore, has the action to promote the production of cytokines such as TNF-α. While the transcribed mRNA is inactivated upon binding to specific protein and then quickly degraded, p38MAPkinase has an action to dissociate the bonds between mRNA and the specific proteins. In this respect also p38MAPkinase is deemed to contribute to the production of cytokines such as TNF-α.

Accordingly, inhibition of p38MAPkinase leads to inhibition of the production of cytokines such as TNF-α and, therefore, is expected to be useful for the treatment or prophylaxis of the diseases related to the cytokines such as TNF-α, for example, acute inflammation, chronic inflammation, rheumatoid arthritis, osteoarthritis, gout, inflammatory bowel disease, Crohn's disease, ulcerative colitis, gastritis, colonic polyposis, large bowel cancer, colon cancer, asthma, bronchitis, bronchial asthma, allergic rhinitis, ARDS, chronic obstructive pulmonary disease, pulmonary fibrosis, congestive heart disease, ischemic heart disease, myocardial infarction, arteriosclerosis, hypertension, angina, Alzheimer's disease, reperfusion injury, angiitis, cerebrovascular disease, meningitis, multiple sclerosis, osteoporosis, bony sclerosis, Behcet's Syndrome, bone metastasis, multiple myeloma, acute infectious disease, septic shock, sepsis, toxic-shock syndrome, tuberculosis, DIC, psoriasis, atopic dermatitis, cirrhosis, renal fibrosis, cachexia, AIDS, cancer, autoimmune disease, diabetes, Castleman's disease, mesangial nephritis, endometriosis and preterm delivery.

In the past, as the compounds having p38MAPkinase-inhibiting action, for example, imidazole derivatives (cf. Bioorganic & Medicinal Chemistry, Vol. 5, No. 1, 49-64 (1997) and JP Tokuhyo Hei 7 (1995)-503017), pyrazole derivatives (cf. PCT International Publications WO98/52940 Pamphlet and WO00/39116 Pamphlet) and isoxazole derivatives (cf. JP Tokuhyo Hei 11 (1999)-503722, JP2002-179656A, PCT International Publication WO2004/17968 Pamphlet, JP 2000-86657A and PCT International Publication WO2004/22555 Pamphlet) have been proposed. However, these compounds are subject to such problems that most of them exhibit side effects and have not matured as marketable medicines.

Only recently certain kind of triazine derivatives were found to possess potent p38MAPkinase-inhibiting action and high speed metabolism, and hence were expected to show reduced side effects and to be prospective antirheumatic medicine (cf. J. Med. Chem., Vol. 47, 6283-6291 (2004)).

DISCLOSURE OF THE INVENTION

An object of the present invention is to provide pyridylisoxazole derivatives which exhibit excellent p38MAPkinase-inhibiting activity and reduced side effects.

We have now discovered that a certain kind of novel 4-(4-pyridyl)isoxazole derivatives possess excellent p38MAPkinase-inhibiting activity and high expiration rate of metabolically active substance in blood, and hence have the potential to reduce the side effects which have been the drawback in past p38MAPkinase-inhibitors, and completed the present invention.

Thus, according to the invention, pyridylisoxazole derivatives which are represented by a formula (I)

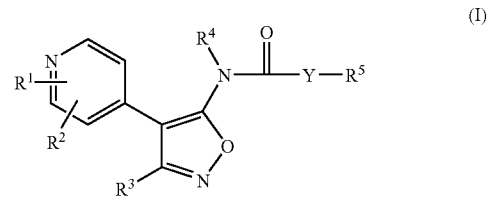

in the formula, $R^1$ and $R^2$ each independently stands for hydrogen, halogen, lower alkyl, lower alkoxy, amino, lower alkylamino, di-lower alkyl-amino, phenyl-lower alkylamino, acylamino, lower alkylthio or lower alkylsulfinyl, $R^3$ stands for naphthyl, optionally lower alkyl-substituted heteroaryl or a group represented by the following formula (A)

wherein $X^1$, $X^2$ and $X^3$ each independently stands for hydrogen, halogen, lower alkyl, lower haloalkyl, lower alkoxy, lower haloalkoxy, hydroxyl, lower alkanoyl, lower haloalkanoyl or phenyl; or $X^1$ and $X^2$ together stand for lower alkylenedioxy group, $R^4$ stands for hydrogen or lower alkyl, $R^5$ stands for phenyl, thienyl, furyl, pyrrolyl, imidazolyl, pyrazolyl, thiazolyl, isothiazolyl, oxazolyl or isoxazolyl, which may be optionally substituted with 1-3 substituents selected from halogen, lower alkyl, lower haloalkyl, lower alkoxy, hydroxyl, lower alkanoyl, lower haloalkanoyl, lower alkylthiocarbonyl, lower haloalkylthio-carbonyl, amino, lower alkylamino, di-lower alkylamino and nitro, Y stands for —(CH$_2$)$_n$—, —CO—, —CH(CH$_3$)—, —C(CH$_3$)$_2$—, —O—, —NH— or

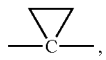

wherein n is an integer of 1-3, with the proviso that, where both of R$^1$ and R$^2$ stand for hydrogen and R$^3$ stands for the group of the formula (A) and two of X$^1$, X$^2$ and X$^3$ stand for hydrogen, the remaining one of X$^1$, X$^2$ and X$^3$ is a group other than hydrogen atom or halogen atom,
or pharmaceutically acceptable salts thereof are provided.

The invention also provides p38MAPkinase inhibitors characterized by containing pyridylisoxazole derivatives of the formula (I) or pharmaceutically acceptable salts thereof.

In the present specification, the term, "lower" signifies that a group modified by this term contains no more than 6, preferably no more than 4, carbon atoms.

"Lower alkyl" can be of straight chain or branched chain, examples of which include methyl, ethyl, n-propyl, isopropyl, n-butyl, isobutyl, sec-butyl, tert-butyl, n-pentyl and n-hexyl; methyl, ethyl, n-propyl, isopropyl and n-butyl being preferred among these. "Lower alkoxy" includes oxy (O) group bound to the lower alkyl, such as, for example, methoxy, ethoxy, n-propoxy, isopropoxy, n-butoxy, isobutyloxy, sec-butyloxy, n-pentyloxy and n-hexyloxy; methoxy, ethoxy, n-propoxy, isopropoxy and n-butoxy being preferred among these. "Lower alkanoyl" includes carbonyl (C=O) group bound to the lower alkyl, such as acetyl, propionyl, butyryl, isobutyryl, valeryl, isovaleryl and pivaloyl; acetyl and propionyl being preferred among these.

Furthermore, "halogen" and "halo" include fluorine, chlorine, bromine and iodine; fluorine, chlorine and bromine being particularly preferred.

"Lower alkylamino" in the definition of R$^1$ signifies amino group (—NH$_2$) of which one of the hydrogen atoms is substituted with the lower alkyl; and "di-lower alkylamino", amino group of which two hydrogen atoms are substituted with the lower alkyl. Here the two lower alkyl groups in such di-lower alkylamino may be the same or different. "Phenyl-lower alkylamino" in the definition of R$^1$ is such a lower alkylamino of which lower alkyl moiety is substituted with phenyl, examples of which include benzylamino, 2-phenylethylamino, 3-phenyl-n-propylamino, 4-phenyl-n-butylamino, 1-phenylethylamino and 1-(phenylmethyl)ethylamino; benzylamino and 2-phenylethyl-amino being preferred among these.

"Acylamino" in the definition of R$^1$ signifies acylated amino, examples of the acyl group including lower alkanoyl groups such as formyl, acetyl, propionyl and butyryl, and aroyl groups such as benzoyl; acetyl and benzoyl being preferred among these.

"Lower alkylthio" and "lower alkylsulfinyl" in the definition of R$^1$ respectively mean thio (S) group and sulfinyl (SO) group, to which the lower alkyl is bound.

"Optionally lower alkyl-substituted heteroaryl" in the definition of R$^3$ signifies unsubstituted or the lower alkyl-substituted monocyclic or polycyclic heteroaryl groups, wherein the heteroaryl groups include 5- to 10-membered aromatic groups having in the ring 1-3 hetero atoms selected from N, O and S, specific examples of which include furyl, pyrrolyl, thienyl, imidazolyl, pyrazolyl, oxazolyl, isoxazolyl, thiazolyl, isothiazolyl, pyridyl, pyrazinyl, pyrimidinyl, pyridazinyl, indolyl, benzoimidazolyl, benzoxazolyl, benzoisoxazolyl, benzothiazolyl, benzoisothiazolyl, quinolyl, isoquinolyl and quinazolyl; furyl, pyrrolyl, thienyl and pyridyl being preferred among these.

In the groups represented by the following formula

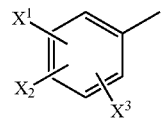

(A)

in the definition of R$^3$, X$^1$, X$^2$ and X$^3$ may substitute at any of the different positions on the benzene ring, and their binding sites are subject to no particular limitation.

"Lower haloalkyl" in the definition of X$^1$, X$^2$ and X$^3$ in the above formula (A) includes lower alkyl groups as earlier defined, which are substituted with one or more same or different halogen atoms, examples of which include fluoromethyl, trifluoromethyl, 1,2-dichloroethyl, 1-chloro-2-bromoethyl, pentafluoroethyl, 1-chloro-n-propyl, 2-bromo-2-methylethyl, 3-chloro-n-pentyl, 2-bromo-3-chloro-n-hexyl and the like. Of these, C$_{1-2}$ lower alkyl substituted with 1-5 same or different halogen atoms are preferred.

"Lower haloalkoxy" in the definition of X$^1$, X$^2$ and X$^3$ in the above formula (A) includes oxy (O) group to which above lower haloalkyl is bound. In particular, C$_{1-2}$ lower haloalkoxy groups substituted with 1-5 same or different halogen atoms are preferred.

"Lower haloalkanoyl" in the definition of X$^1$, X$^2$ and X$^3$ in the formula (A) includes aforesaid lower alkanoyl groups which are substituted with 1 or more halogen atoms, examples of which include fluoroacetyl, chloroacetyl, bromoacetyl, trifluoroacetyl, 3-fluoropropionyl, 3-chloropropionyl, 3-bromopropionyl, 4-chlorobutyryl and the like. Of these, fluoroacetyl, trifluoroacetyl, 3-fluoropropionyl and 3-chloropropionyl are preferred.

As examples of "lower alkylenedioxy" in the definition of X$^1$, X$^2$ and X$^3$ in the formula (A), methylenedioxy, ethylenedioxy, trimethylenedioxy and the like can be named, among which methylenedioxy and ethylenedioxy are preferred.

As examples of "lower haloalkyl", "lower alkanoyl" and "lower haloalkanoyl" in the definition of R$^5$, respectively those groups named as for "lower haloalkyl" "lower alkanoyl" and "lower haloalkanoyl" in the definition of X$^1$, X$^2$ and X$^3$ in the formula (A) can be named, among which the preferred groups also are the same.

"Lower alkylthiocarbonyl" in the definition of R$^5$ signifies thiocarbonyl (C=S) to which aforesaid lower alkyl is bound, examples of which include thioacetyl, thiopropionyl, thiobutyryl, thiopentanoyl, thiohexanoyl and the like, thioacetyl and thiopropionyl being preferred among these.

"Lower haloalkylthiocarbonyl" in the definition of R$^5$ signifies above lower alkylthiocarbonyl which is substituted with 1 or more halogen atoms, examples of which include fluorothioacetyl, chlorothioacetyl, bromothioacetyl, trifluorothioacetyl, chlorothio-propionyl, chlorothiobutyryl, bromothiopentanoyl, fluorothiohexanoyl and the like, fluorothioacetyl, chlorothioacetyl, bromothioacetyl and trifluorothioacetyl being preferred among these.

Where both R$^1$ and R$^2$ in the formula (I) are hydrogen, R$^3$ stands for the group of formula (A) and two of X$^1$, X$^2$ and X$^3$ stand for hydrogen, the compounds in which the remaining one of X$^1$, X$^2$ and X$^3$ stands for hydrogen or halogen are disclosed in JP 2000-86657A and hence are excluded from the compounds of the formula (I) of the present invention.

A preferred group of compounds in the present invention are those of the formula (I) in which $R^1$ and $R^2$ each independently stands for hydrogen, amino, lower alkylamino or di-lower alkylamino, in particular, those of the formula (I) in which both $R^1$ and $R^2$ stand for hydrogen. When either one of $R^1$ and $R^2$ stands for hydrogen and the other stands for a group other than hydrogen, that group preferably is substituted at 2-position of the pyrimidine ring.

Another preferred group of compounds in the present invention are those of the formula (I) in which $R^2$ stands for a group represented by the following formula

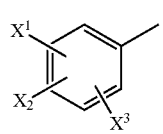

(A)

in particular, those in which $X^1$, $X^2$ and $X^3$ each independently stands for hydrogen, halogen, lower alkyl or lower alkoxy.

Still another preferred group of compounds in the present invention are those of the formula (I) in which $R^4$ stands for hydrogen.

A further preferred group of compounds in the present invention are those of the formula (I) in which $R^5$ stands for phenyl which is optionally substituted with 1-3 substituents selected from halogen, lower alkyl, lower haloalkyl, lower alkoxy, hydroxyl, lower alkanoyl, lower haloalkanoyl, lower alkylthiocarbonyl, lower haloalkylthiocarbonyl, amino, lower alkylamino, di-lower alkylamino and nitro. In particular, those compounds of the formula (I) in which $R^5$ stands for phenyl which is optionally substituted with 1 or 2 substituents selected from halogen and lower alkyl are better preferred, inter alia, the compounds of the formula (I) in which $R^5$ is phenyl, 2-halophenyl, 2,6-dihalophenyl, 2-lower alkylphenyl, 3-lower alkylphenyl or 2,5-di-lower alkylphenyl are best preferred.

Another preferred group of compounds in the present invention are the compounds of the formula (I) in which Y stands for —$CH_2$— or —$(CH_2)_2$—.

Particularly preferred compounds according to the invention are as follows:

3-(3-methylphenyl)-5-(3-phenylpropionylamino)-4-(4-pyridyl)-isoxazole,
3-(3-methylphenyl)-5-[(2-methylphenyl)propionylamino]-4-(4-pyridyl)isoxazole,
5-[(3-chlorophenyl)propionylamino]-3-(2-fluoro-5-methylphenyl)-4-(4-pyridyl)isoxazole,
3-(4-fluoro-3-methylphenyl)-5-(phenylacetylamino)-4-(4-pyridyl)isoxazole,
5-[(2-chlorophenyl)acetylamino]-3-(4-fluoro-3-methylphenyl)-4-(4-pyridyl)isoxazole, and
3-(4-fluoro-3-methylphenyl)-5-(3-phenylpropionylamino)-4-(4-pyridyl)isoxazole.

Also as the typical examples of the compounds of the formula (I) offered by the present invention, the following can be named other than those given in the later appearing Examples:

3-(4-fluorophenyl)-4-[4-(2-methylaminopyridyl)]-5-phenylacetylaminoisoxazole,
3-(4-fluorophenyl)-4-[4-(2-methylaminopyridyl)]-5-(3-phenylpropionylamino)isoxazole,
4-[4-(2-benzylaminopyridyl)]-3-(4-fluorophenyl)-5-phenylacetylaminoisoxazole,
4-[4-(2-benzylaminopyridyl)]-3-(4-fluorophenyl)-5-(3-phenyl-propionylamino)isoxazole,
4-[4-(2-acetylaminopyridyl)]-3-(4-fluorophenyl)-5-phenylacetylaminoisoxazole,
4-[4-(2-acetylaminopyridyl)]-3-(4-fluorophenyl)-5-(3-phenyl-propionylamino)isoxazole,
4-[4-(2-benzoylaminopyridyl)]-3-(4-fluorophenyl)-5-phenyl-acetylaminoisoxazole,
4-[4-(2-benzoylaminopyridyl)]-3-(4-fluorophenyl)-5-(3-phenyl-propionylamino)isoxazole,
3-(4-fluoro-3-methylphenyl)-5-(N-methyl-phenylacetylamino)-4-(4-pyridyl)isoxazole,
3-(4-fluoro-3-methylphenyl)-5-[N-methyl-(3-phenylpropionyl)-amino]-4-(4-pyridyl)isoxazole,
5-[(2-aminophenyl)acetylamino]-3-(4-fluoro-3-methylphenyl)-4-(4-pyridyl)isoxazole,
3-(4-fluoro-3-methylphenyl)-5-[(2-hydroxyphenyl)-acetylamino]-4-(4-pyridyl)isoxazole,
3,4-di(4-pyridyl)-5-phenylacetylaminoisoxazole,
3,4-di(4-pyridyl)-5-(3-phenylpropionylamino)isoxazole,
3-[4-(2-methylpyridyl)]-5-phenylacetylamino-4-(4-pyridyl)-isoxazole,
3-[4-(2-methylpyridyl)]-5-(3-phenylpropionylamino)-4-(4-pyridyl)isoxazole, and the like.

The compounds of the formula (I) of the present invention can also be present in the form of salt. As examples of the salts, those with inorganic acids such as hydrochloric acid, hydrobromic acid, sulfuric acid, nitric acid, phosphoric acid and the like; and those with organic acids such as acetic acid, oxalic acid, citric acid, lactic acid, tartaric acid, p-toluenesulfonic acid and the like can be name. Of these, pharmaceutically acceptable salts are preferred.

The compounds of the formula (I) according to the invention can be prepared, for example, by the following method (a) or (b).

Method (a):

A compound of the formula (I) in which $R^4$ stands for hydrogen, i.e., a compound of the following formula,

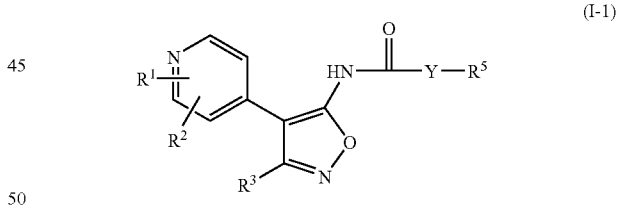

(I-1)

in the formula, $R^1$, $R^2$, $R^3$, $R^5$ and Y have the previously given significations, can be prepared by reaction of a compound represented by the following formula,

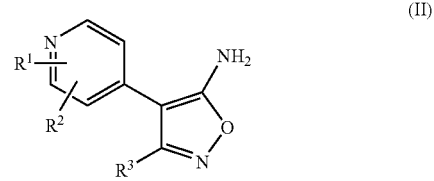

(II)

in the formula, $R^1$, $R^2$ and $R^3$ have the previously given significations,
with a carboxylic acid compound of the following formula,

 (III)

in the formula, $R^5$ and Y have the previously given significations,
or its reactive derivative (for example, acid halide, acid anhydride, mixed acid anhydride, active amide, active ester or the like).

Method (b):

A compound of the formula (I) in which $R^4$ stands for a lower alkyl, i.e., a compound represented by the following formula,

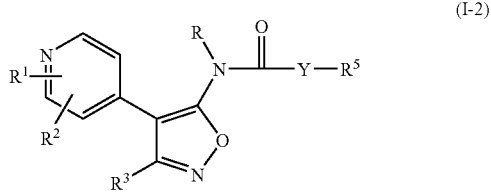 (I-2)

in the formula, $R^1$, $R^2$, $R^3$, $R^5$ and Y have the previously given significations, and R stands for a lower alkyl,
can be prepared by N-lower alkylation of a compound of the formula (I-1).

In the method (a), it is desirable that the carboxylic acid compound of the formula (III) is advancedly treated with, for example, 1,1-carbonyldiimidazole (CDI), 1,1-thionyldiimidazole or the like, to be converted to a reactive derivative thereof such as active amide. It is also possible when acid halide, for example, acid chloride, is used as the reactive derivative of the carboxylic acid compound of the formula (III), to treat the acid halide in advance with, for example, imidazole and DBU or the like to convert it to other reactive derivative such as imidazolide.

Furthermore, when $R^1$ in the compounds of the formula (II) represents amino, lower alkylamino or phenyl-loweralkylamino, it is advantageous to protect the amino, lower alkylamino or phenyl-lower alkylamino in advance with a suitable protective group, for example, with the use of di-tert-butyl dicarbonate (BOC), acetonyl acetone, benzyloxycarbonyl chloride (Z-chloride) or the like where necessary, removing the protective group after termination of the reaction.

The reaction of a compound of the formula (II) with a carboxylic acid compound of the formula (III) or a reactive derivative thereof can generally be conducted in inert organic solvent, for example, ethers such as dioxane, tetrahydrofuran and dimethoxyethane; aromatic hydrocarbons such as benzene, toluene and xylene; halogenated hydrocarbons such as dichloromethane and chloroform; amides such as dimethylformamide and dimethyl-acetamide; dimethylsulfoxide; and, where necessary, in the presence of a base, for example, 1,8-diazabicyclo[5.4.0]undec-7-ene (DBU), triethylamine, diisopropylethylamine, pyridine or the like. The suitable reaction temperature is normally within a range of 0° C. to the reflux temperature of the reaction mixture, preferably from the temperature under cooling with ice up to 50° C.

The carboxylic acid compound of the formula (III) or reactive derivative thereof can be generally used in an amount of at least 1 mol, preferably 1.5-10 mols, inter alia, 2-5 mols, per mol of the compound of the formula (II). Also the use rate of the base is generally at least 1 mol, preferably 1-2 mols, per mol of the carboxylic acid compound of the formula (III) or reactive derivative thereof.

Compounds of the formula (II) which are used as the starting material can be readily synthesized by those synthesis methods known per se, for example, following the route indicated by the following reaction scheme 1. Concerning the particulars of the reaction conditions and the like of the reaction scheme 1, refer to Example 1, a) given later.

Reaction scheme 1:

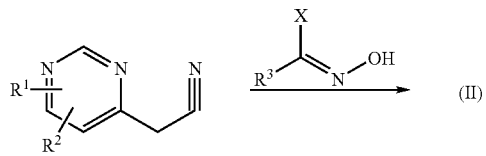 (II)

in which $R^1$, $R^2$ and $R^3$ have the previously given significations, and X stands for halogen.

The N-lower alkylation of the compounds of the formula (I-1) according to the method (b) can generally be carried out by reacting the compounds with lower alkyl halide, for example, iodomethane, ethyl bromide, propyl bromide and the like, in inert organic solvent, for example, alcohols such as methanol, ethanol and isopropanol; ethers such as dioxane, tetrahydrofuran and dimethoxyethane; aromatic hydrocarbons such as benzene, toluene and xylene; amides such as dimethylformamide and dimethylacetamide; and dimethylsulfoxide; and in the presence of a suitable base such as sodium hydride, potassium carbonate, pyridine and the like. The suitable reaction temperature is normally within a range of 0° C. to the reflux temperature of the reaction mixture, preferably from room temperature to 50° C.

The lower alkyl halide can be used generally in an amount of at least 1 mol, preferably 1.1-5 mols, inter alia, 1.2-4 mols, per mol of a compound of the formula (I-1). The use rate of the base is generally at least 1 mol, preferably within a range of 1-5 mols, per mol of a compound of the formula (I-1).

Those compounds of the formula (I) of the present invention which are prepared following the above-described methods can be isolated and purified by the means known per se, for example, recrystallization, column chromatography, thin-layer chromatography and the like.

The pyridylisoxazole derivatives represented by the formula (I) of the present invention or their pharmaceutically acceptable salts possess excellent p38MAPkinase-inhibiting action with reduced side effects, and are useful for the treatment or prophylaxis of human and other mammals' TNF-α-, IL-1-, IL-6-, IL-8- and COX-II-related diseases, for example, acute inflammation, chronic inflammation, rheumatoid arthritis, osteoarthritis, gout, inflammatory bowel disease, Crohn's disease, ulcerative colitis, gastritis, colonic polyposis, large bowel cancer, colon cancer, asthma, bronchitis, bronchial asthma, allergic rhinitis, ARDS, chronic obstructive pulmonary disease, pulmonary fibrosis, congestive heart disease, ischemic heart disease, myocardial infarction, arteriosclerosis, hypertension, angina, Alzheimer's disease, reperfusion injury, angiitis, cerebrovascular disease, meningitis, multiple sclerosis, osteoporosis, bony sclerosis, Behcet's Syndrome, bone metastasis, multiple myeloma, acute infectious disease, septic shock, sepsis, toxic-shock syndrome, tuberculosis, DIC, psoriasis, atopic dermatitis, cirrhosis, renal fibrosis, cachexia, AIDS, cancer, autoimmune disease, diabetes, Castleman's disease, mesangial nephritis, endometriosis and preterm delivery.

The TNF-α production inhibitory action based on the p38MAPkinase-inhibiting action possessed by the compounds of the formula (I) of the present invention and metabolic expiration rate in blood of the compounds of the formula (I) of the present invention can be demonstrated by the following experiments.

(1) Measurement of TNF-α Production-Inhibiting Action

THP-1, human-derived culture cells (purchased from Dainippon Pharmaceutical Co.), was suspended ($1\times10^5$ cells/mL) in RPMI 1640 medium (10% fetal bovine serum, containing 100 units/mL of penicillin). The THP-1 cell suspension 1.6 mL was inoculated in a 24-well culture plate, to which further a solution of test substance as dissolved in RPMI 1640 medium to make the final concentration of the test substance 100 nM and 0.2 mL of LPS (*E. coli* 055: B5-derived, dissolved in RPMI 1640 medium, Difco) of 10 μg/mL in concentration were added, followed by 2 hours' culture under the conditions of 37° C. and 5% $CO_2$. The supernatant which was obtained upon centrifuge (500×g, 5 minutes) was measured with ELISA (Amersham Biosciences, TNF-α Human, ELISA Biotrak System) to quantize TNF-α. The TNF-α production inhibition rate (%) at 100 nM of each test substance was calculated according to the following formula, $$\left[1 - \frac{\text{quantity of } TNF\text{-}\alpha \text{ when each test substance was used}}{\text{quantity of } TNF\text{-}\alpha \text{ in control experiment}}\right] \times 100$$

The results are shown in the later-appearing Table A.

(2) Measurement of the Compounds' Metabolic Rate:

Each test compound was added to potassium phosphate buffer (50 mmol/L, pH7.4) containing NADPH generating system (comprising 3.3 mmol/L $MgCl_2$, 3.3 mmol/L glucose 6-phosphate, 1.3 mmol/L β-$NADP^+$ and 0.4 unit/mL glucose 6-phosphate dehydrogenase) (in which occasion the final concentration was rendered 1 μmol/L) and incubated at 37° C. for 2 minutes. After the incubation, a suspension of human liver S9 (the supernatant fraction obtained by centrifuging comminuted human liver cell fluid at 9000×g) in potassium phosphate buffer was added to the system, to the final concentration of 0.5 mg protein/mL. This reaction mixture was incubated at 37° C. for 5 minutes, and to which 4 volume times the reaction mixture of acetonitrile was added, mixed, cooled with ice and centrifuged (2000×g, 10 minutes). A part of the supernatant was taken and analyzed by LC/MS/MS, to determine the remaining rate of unchanged substance in the reaction solution. The results are shown in the following Table A, concurrently with the measured results of TNF-α production-inhibiting action in (1) above.

TABLE A

| Compound | Structural formula | TNF-α generation-inhibiting action (inhibition: rate: %, 100 nM) | Metabolic rate (remaining ratio of unchanged substance: %) |
| --- | --- | --- | --- |
| Example 103 | | 65.5 | 17.6 |
| Example 106 | | 52.9 | 23.3 |
| Example 117 | | 58.1 | 50.5 |

TABLE A-continued

| Compound | Structural formula | TNF-α generation-inhibiting action (inhibition: rate: %, 100 nM) | Metabolic rate (remaining ratio of unchanged substance: %) |
|---|---|---|---|
| Example 123 | | 78.1 | 58.0 |
| Example 124 | | 85.2 | 59.7 |
| Example 125 | | 66.0 | 20.1 |

Thus the pyridylisoxazole derivatives represented by the formula (I) of the present invention or their pharmaceutically acceptable salts can be orally or parenterally (e.g., intramuscular injection, intravenous injection, intrarectal or percutaneous administration and the like) administered to patients who need the therapy, treatment or prophylaxis as medicines for therapy, treatment or prophylaxis of human or other mammals' diseases, as p38MAPkinase inhibitor having excellent activity and high metabolic rate.

Where the compounds of the present invention are used as medicines, they can be formulated into certain preparation forms according to their utility, with non-toxic excipients, such as solids (e.g., tablet, hard capsule, soft capsule, granule, powder, grain, pill, troche and the like); semi-solids (e.g., suppository, ointment and the like) or liquid (e.g., injection, emulsion, suspension, lotion, spray and the like). As the non-toxic excipients useful for such preparations, for example, starch, gelatine, glucose, lactose, fructose, maltose, magnesium carbonate, talc, magnesium stearate, methyl cellulose, carboxymethyl cellulose or salts thereof, gum arabic, polyethylene glycol, alkyl p-hydroxybenzoate, syrup, ethanol, propylene glycol, petrolatum, carbowax, glycerine, sodium chloride, sodium sulfite, sodium phosphate, citric acid and the like can be named. The preparations can also contain other therapeutically useful medicines.

Thus, according to the present invention, pharmaceutical compositions containing effective amount of the pyridylisoxazole derivatives represented by the formula (I) or pharmaceutically acceptable salts thereof, concurrently with non-toxic excipients are provided.

While the content of a compound of the present invention in such preparations or compositions differs according to the preparation form, in general terms it is desirable to be within a range of 0.1-50% by weight for solid and semi-solid forms, and within a range of 0.05-10% by weight for liquid forms.

The administration dosage of a compound of the present invention is variable over a wide range according to the species, age, body weight, administration route, seriousness of symptoms and doctor's diagnosis, of the patients including human and other warm-blooded animals. Whereas, in general terms, it can range 0.02-20 mg/kg, preferably 0.2-8 mg/kg, per day. Obviously, dosages less than the lower limit or more than the upper limit of the above-specified range may be administered depending on seriousness of the patient's symptoms, doctor's diagnosis and the like. The dosage can be administered as a single dose or plural divided doses per day.

EXAMPLES

Hereinafter the present invention is explained in further details, referring to Examples and Preparation Examples.

Example 1

3-(2,3-Difluorophenyl)-5-(phenylacetylamino)-4-(4-pyridyl)isoxazole a) 5-Amino-3-(2,3-difluorophenyl)-4-(4-pyridyl)isoxazole In 15 mL of methanol, 2.31 g of 28% sodium methoxide-methanol solution was dissolved, and a suspension of 0.93 g of 4-pyridylacetonitrile hydrochloride in 10 mL of THF was added, followed by an hour's stirring at room temperature. Then a solution of 1.15 g of 2,3-difluorobenzhydroxymoyl chloride in 5 mL of methanol was added dropwise, followed by 20 hours' stirring at room temperature. The reaction solution was extracted with ethyl acetate after addition of water. The ethyl acetate extract was washed with brine, dried over anhydrous magnesium sulfate, and removed of the solvent by reduced pressure distillation. The resultant residue was purified on 100 g silica gel column chromatography (eluent, ethyl acetate→ethyl acetate:methanol=9:1) to provide 1.06 g (yield: 65%) of the title compound as pale yellow crystal.

$^1$H-NMR(CDCl$_3$)δ:8.51(dd,J=1.7 Hz,4.4 Hz,2H),7.31-7.21(m,2H),7.19-7.13(m,1H),7.00(dd,J=1.7 Hz,4.4 Hz,2H),4.94(bs,2H)

Mass,m/e:273(M$^+$),63(base)

b) 3-(2,3-Difluorophenyl)-5-(Phenylacetylamino)-4-(4-pyridyl)-isoxazole

In 3 mL of THF, 68 mg of imidazole and 152 mg of DBU were dissolved, into which 155 mg of phenylacetyl chloride was dropped under cooling with ice and stirring, followed by 1.5 hours' stirring at room temperature. Then a solution of 137 mg of 5-amino-3-(2,3-difluorophenyl)-4-(4-pyridyl)isoxazole and 152 mg of DBU in 3 mL of THF was added dropwise, followed by 26 hours' stirring at room temperature. After addition of water, the reaction solution was extracted with ethyl acetate. The ethyl acetate extract was washed first with saturated aqueous NaHCO$_3$ solution and then with brine, dried over anhydrous magnesium sulfate, and removed of the solvent by reduced pressure distillation. The resultant residue was purified by thin-layer silica gel chromatography (developer, hexane:ethyl acetate=1:1) to provide 88 mg (yield: 45%) of the title compound as colorless crystal.

$^1$H-NMR(CDCl$_3$)δ:8.43(dd,J=1.6 Hz,4.5 Hz,2H),7.78(bs,1H),7.43-7.13(m,8H),6.81(dd,J=1.6 Hz,4.5 Hz,2H),3.78(s,2H)

Mass,m/e:391(M$^+$),91(base)

Example 2

5-[2-(2-chlorophenyl)acetylamino]-3-(2,3-difluorophenyl)-4-(4-pyridyl)isoxazole

To a solution of 0.171 g of 2'-chlorophenylacetic acid in 5 mL of THF, 0.162 g of CDI was added, and stirred at room temperature for 1.5 hours. Then a solution of 0.152 g of DBU and 0.137 g of 5-amino-3-(2,3-difluorophenyl)-4-(4-pyridyl)isoxazole in 1 mL of THF was added, and stirred at room temperature for 18 hours. After addition of water, the reaction solution was extracted with ethyl acetate. The ethyl acetate extract was washed first with saturated aqueous NaHCO$_3$ solution and then with brine, dried over anhydrous magnesium sulfate, and removed of the solvent by reduced pressure distillation. The resultant residue was purified on 3 g silica gel column chromatography (eluent, ethyl acetate) to provide 0.126 g (yield, 59%) of the title compound as pale yellow crystal.

$^1$H-NMR(CDCl$_3$)δ:8.45(dd,J=1.5 Hz,4.4 Hz,2H),7.83(bs,1H),7.47-7.43(m,1H),7.36-7.12(m,6H),6.91(dd,J=1.5 Hz,4.4 Hz,2H),3.89(s,2H)

Mass,m/e:425(M$^+$),125(base)

In the following, the compounds of Examples 3-183 were synthesized in the manner similar to Examples 1 and 2.

Example 3

3-(2,3-Difluorophenyl)-5-(phenylpropionylamino)-4-(4-pyridyl)-isoxazole $^1$H-NMR(CDCl$_3$)δ:8.41(dd,J=1.5 Hz,4.6 Hz,2H),8.02(bs,1H),7.32-7.13(m,8H),6.87(dd,J=1.5 Hz,4.6 Hz,2H),3.01(t,J=7.3 Hz,2H),2.77(t,J=7.3 Hz,2H)

Mass,m/e:405(M$^+$),91(base)

Example 4

3-(2,4-Difluorophenyl)-5-(phenylacetylamino)-4-(4-pyridyl)isoxazole a) 5-Amino-3-(2,4-difluorophenyl-4-(4-pyridyl)isoxazole $^1$H-NMR(CDCl$_3$)δ:8.50(dd,J=1.5 Hz,4.6 Hz,2H),7.52-7.45(m,1H),7.00-6.96(m,3H),6.87-6.80(m,1H),4.93(bs,2H)

Mass,m/e:273(M$^+$),63(base)

b) 3-(2,4-Difluorophenyl)-5-(phenylacetylamino)-4-(4-pyridyl)-isoxazole $^1$H-NMR(CDCl$_3$)δ:8.43(dd,J=1.5 Hz,4.6 Hz,2H),7.50-7.34(m,4H),7.30-7.25(m,2H),7.00-6.94(m,1H),6.83-6.77(m,3H),3.77(s,2H)

Mass,m/e:391(M$^+$),91(base)

Example 5

5-[2-(2-Chlorophenyl)acetylamino]-3-(2,4-difluorophenyl)-4-(4-pyridyl)isoxazole $^1$H-NMR(DMSO-d$_6$)δ:11.24(bs,1H),8.49(dd,J=1.6 Hz,4.5 Hz,2H),7.68-7.61(m,1H),7.46-7.36(m,3H),7.33-7.24(m,3H),7.09(dd,J=1.6 Hz,4.5 Hz,2H),3.91(s,2H)

Mass,m/e:425(M$^+$),125(base)

Example 6

3-(2,4-Difluorophenyl)-5-(phenylpropionylamino)-4-(4-pyridyl)-isoxazole $^1$H-NMR(CDCl$_3$)δ:8.45(dd,J=1.6 Hz,4.5 Hz,2H),7.76(bs,1H),7.50-7.43(m,1H),7.33-7.17(m,5H),7.01-6.95(m,1H),6.88(dd,J=1.6 Hz,4.5 Hz,2H),6.84-6.78(m,1H),3.01(t,J=7.4 Hz,2H),2.77(t,J=7.4 Hz,2H)

Mass,m/e:405(M$^+$),91(base)

Example 7

5-[(2-Chlorophenyl)propionylamino]-3-(2,4-difluorophenyl)-4-(4-pyridyl)isoxazole $^1$H-NMR(CDCl$_3$)δ:8.42(d,J=6.1 Hz,2H),8.26(bs,1H), 7.49-7.43(m,1H),7.35-7.31(m,1H),7.24-7.15(m,3H),6.99-6.94(m,1H),6.91(d,J=6.1 Hz,2H),6.82-6.77(m,1H),3.11(t, J=7.6 Hz,2H),2.78(t,J=7.6 Hz,2H)
Mass,m/e:439(M$^+$),273(base)

Example 8

5-[(3-Chlorophenyl)propionylamino]3-(2,4-difluorophenyl)-4-(4-pyridyl)isoxazole $^1$H-NMR(CDCl$_3$)δ:8.44(bs,1H),8.39(d,J=5.8 Hz,2H), 7.48-7.43(m,1H),7.21-7.18(m,3H),7.08-7.06(m,1H),6.99-6.94(m,1H),6.88(d,J=6.0 Hz,2H),6.82-6.77(m,1H),2.98(t, J=7.0 Hz,2H),2.77(t,J=7.0 Hz,2H)
Mass,m/e:439(M$^+$),273(base)

Example 9

3-(2,4-Difluorophenyl)-5-[(2-methylphenyl)propionylamino]-4-(4-pyridyl)isoxazole $^1$H-NMR(CDCl$_3$)δ:8.40(d,J=5.9 Hz,2H),8.22(bs,1H), 7.49-7.43(m,1H),7.15-7.10(m,4H),6.99-6.94(m,1H),6.89(d, J=5.9 Hz,2H),6.82-6.77(m,1H),3.00(t,J=7.6 Hz,2H),2.72(t, J=7.6 Hz,2H),2.28(s,3H)
Mass,m/e:419(M$^+$),105(base)

Example 10

3-(2,4-Difluorophenyl)-5-[(3-methylphenyl)propionylamino]-4-(4-pyridyl)isoxazole $^1$H-NMR(CDCl$_3$)δ:8.43(dd,J=1.7 Hz,4.5 Hz,2H),7.83(bs, 1H),7.49-7.43(m,1H),7.11-7.06(m,4H),6.99-6.95(m,1H), 6.87(dd,J=1.7 Hz,4.5 Hz,2H),6.83-6.77(m,1H),2.96(t,J=7.2 Hz,2H),2.74(t,J=7.2 Hz,2H),2.32(s,3H)
Mass,m/e:419(M$^+$),105(base)

Example 11

3-(2,6-Difluorophenyl)-5-(phenylacetylamino)-4-(4-pyridyl)isoxazole a) 5-Amino-3-(2,6-difluorophenyl)-4-(4-pyridyl)isoxazole $^1$H-NMR(CDCl$_3$)δ:8.48(dd,J=1.5 Hz,4.6 Hz,2H),7.47-7.39(m,1H),7.00-6.95(m,4H),4.97(bs,2H)
Mass,m/e:273(M$^+$),63(base)

b) 3-(2,6-Difluorophenyl)-5-(phenylacetylamino)-4-(4-pyridyl)-isoxazole $^1$H-NMR(CDCl$_3$)δ:8.42(dd,J=1.5 Hz,4.7 Hz,2H),7.45-7.37(m,5H),7.31-7.29(m,2H),6.98-6.92(m,2H),6.81(dd, J=1.5 Hz,4.6 Hz,2H),3.79(s,2H)
Mass,m/e:391(M$^+$),91(base)

Example 12

5-[2-(2-Chlorophenyl)acetylamino]-3-(2,6-difluorophenyl)-4-(4-pyridyl)isoxazole $^1$H-NMR(CDCl$_3$)δ:8.43(dd,J=1.5 Hz,4.4 Hz,2H),7.79(bs, 1H),7.47-7.30(m,5H),6.97-6.93(m,2H),6.91(dd,J=1.5 Hz,4.4 Hz,2H),3.90(s,2H)
Mass,m/e:425(M$^+$),125(base)

Example 13

3-(3,4-Difluorophenyl)-5-(phenylacetylamino)-4-(4-pyridyl)isoxazole a) 5-Amino-3-(3,4-difluorophenyl)-4-(4-pyridyl)isoxazole $^1$H-NMR(DMSO-d$_6$)δ:8.44(dd,J=1.2 Hz,4.8 Hz,2H), 7.54-7.36(m,2H),7.32(bs,2H),7.19-7.13(m,1H),7.05(dd, J=1.2 Hz,4.8 Hz,2H)
Mass,m/e:273(M$^+$),63(base)

b) 3-(3,4-Difluorophenyl)-5-(phenylacetylamino)-4-(4-pyridyl)-isoxazole $^1$H-NMR(DMSO-d$_6$)δ:11.09(bs,1H),8.47(dd,J=1.3 Hz,4.8 Hz,2H),7.56-7.45(m,2H),7.36-7.23(m,5H),7.22-7.17 (m,1H),7.07(dd,J=1.3 Hz,4.8 Hz,2H),3.67(s,2H)
Mass,m/e:391(M$^+$),91(base)

Example 14

5-[2-(2-Chlorophenyl)acetylamino]-3-(3,4-difluorophenyl)-4-(4-pyridyl)isoxazole $^1$H-NMR(DMSO-d$_6$)δ:11.14(bs,1H),8.54(dd,J=1.5 Hz,4.4 Hz,2H),7.51-7.18(m,7H),7.18(dd,J=1.5 Hz,4.4 Hz,2H),3.87(s,2H)
Mass,m/e:391(M$^+$),91(base)

Example 15

3-(3-Chloro-2-fluorophenyl)-5-(phenylacetylamino)-4-(4-pyridyl)-isoxazole a) 5-Amino-3-(3-chloro-2-fluorophenyl)-4-(4-pyridyl)isoxazole $^1$H-NMR(DMSO-d$_6$)δ:8.40(dd,J=1.5 Hz,4.5 Hz,2H), 7.78-7.73(m,1H),7.48-7.44(m,3H),7.36(td,J=0.8 Hz,7.9 Hz,1H),6.98(dd,J=1.5 Hz,4.5 Hz,2H)
Mass,m/e:289(M$^+$),63(base)

b) 3-(3-Chloro-2-fluorophenyl)-5-(phenylacetylamino)-4-(4-pyridyl)isoxazole $^1$H-NMR(CDCl$_3$)δ:8.43(dd,J=1.7 Hz,4.4 Hz,2H),7.78(bs, 1H),7.53-7.48(m,1H),7.43-7.32(m,5H),7.30-7.28(m,1H), 7.17(td,J=1.2 Hz,7.9 Hz,1H),6.80(dd,J=1.7 Hz,4.4 Hz,2H), 3.78(s,2H)
Mass,m/e:407(M$^+$),91(base)

Example 16

5-[(2-Chlorophenyl)acetylamino]-3-(3-chloro-2-fluorophenyl)-4-(4-pyridyl)isoxazole $^1$H-NMR(DMSO-d$_6$)δ:11.28(bs,1H),8.49(dd,J=1.6 Hz,4.5 Hz,2H),7.82-7.76(m,1H),7.55-7.50(m,1H),7.47-7.36(m,3H),7.34-7.29(m,2H),7.10(dd,J=1.6 Hz,4.5 Hz,2H),3.91(s,2H)
Mass,m/e:441(M$^+$),125(base)

Example 17

3-(3-Chloro-2-fluorophenyl)-5-(phenylpropionylamino)-4-(4-pyridyl)-isoxazole $^1$H-NMR(CDCl$_3$)δ:8.42(dd,J=1.5 Hz,4.6 Hz,2H),8.00(bs,1H),7.54-7.49(m,1H),7.37-7.27(m,3H),7.25-7.15(m,4H),6.86(dd,J=1.5 Hz,4.6 Hz,2H),3.02(t,J=7.4 Hz,2H),2.78(t,J=7.4 Hz,2H)
Mass,m/e:421(M$^+$),91(base)

Example 18

3-(4-Chloro-2-fluorophenyl)-5-(phenylacetylamino)-4-(4-pyridyl)-isoxazole a) 5-Amino-3-(4-chloro-2-fluorophenyl)-4-(4-pyridyl)isoxazole $^1$H-NMR(DMSO-d$_6$)δ:8.40(d,J=5.4 Hz,2H),7.53-7.51(m,2H),7.43(m,3H),6.98(d,J=5.4 Hz,2H)
Mass,m/e:289(M$^+$),63(base)

b) 3-(4-Chloro-2-fluorophenyl)-5-(phenylacetylamino)-4-(4-pyridyl)isoxazole $^1$H-NMR(CDCl$_3$)δ:8.43(dd,J=1.5 Hz,4.6 Hz,2H),7.66(bs,1H),7.43-7.35(m,4H),7.28-7.22(m,3H),7.07(dd,J=1.9 Hz,9.6 Hz,1H),6.79(dd,J=1.5 Hz,4.6 Hz,2H),3.77(s,2H)
Mass,m/e:407(M$^+$),91(base)

Example 19

5-[(2-Chlorophenyl)acetylamino]-3-(4-chloro-2-fluorophenyl)-4-(4-pyridyl)isoxazole $^1$H-NMR(DMSO-d$_6$)δ:11.25(bs,1H),8.49(dd,J=1.5 Hz,4.6 Hz,2H),7.62-7.56(m,2H),7.48-7.38(m,3H),7.33-7.28(m,2H),7.10(dd,J=1.5 Hz,4.6 Hz,2H),3.91(s,2H)
Mass,m/e:441(M$^+$),125(base)

Example 20

3-(4-Chloro-2-fluorophenyl)-5-(phenylpropionylamino)-4-(4-pyridyl)-isoxazole $^1$H-NMR(CDCl$_3$)δ:8.44(bs,1H),8.37(d,J=5.5 Hz,2H),7.40(t,J=7.7 Hz,1H),7.30-7.17(m,6H),7.07(dd,J=1.9 Hz,9.6 Hz,1H),6.85(d,J=5.5 Hz,2H),3.00(t,J=7.3 Hz,2H),2.76(t,J=7.3 Hz,2H)
Mass,m/e:421(M$^+$),91(base)

Example 21

3-(4-Chloro-3-fluorophenyl)-5-(phenylacetylamino)-4-(4-pyridyl)-isoxazole a) 5-Amino-3-(4-chloro-3-fluorophenyl)-4-(4-pyridyl)isoxazole $^1$H-NMR(CDCl$_3$)δ:8.56(dd,J=1.5 Hz,4.2 Hz,2H),7.38(t,J=8.0 Hz,1H),7.25(dd,J=1.9 Hz,9.6 Hz,1H),7.13-7.11(m,1H),7.05(dd,J=1.5 Hz,4.2 Hz,2H),4.91(bs,2H)
Mass,m/e:289(M$^+$),63(base)

b) 3-(4-Chloro-3-fluorophenyl)-5-(phenylacetylamino)-4-(4-pyridyl)-isoxazole $^1$H-NMR(DMSO-d$_6$)δ:11.12(bs,1H),8.48(dd,J=1.7 Hz,4.4 Hz,2H),7.68(t,J=8.0 Hz,1H),7.45(dd,J=1.9 Hz,10 Hz,1H),7.35-7.25(m,5H),7.19(dd,J=1.1 Hz,8.1 Hz,1H),7.08(dd,J=1.7 Hz,4.4 Hz,2H),3.68(s,2H)
Mass,m/e:407(M$^+$),91(base)

Example 22

5-[(2-Chlorophenyl)acetylamino]-3-(4-chloro-3-fluorophenyl)-4-(4-pyridyl)isoxazole $^1$H-NMR(DMSO-d$_6$)δ:11.17(bs,1H),8.54(dd,J=1.5 Hz,4.2 Hz,2H),7.68(t,J=8.0 Hz,1H),7.47(dd,J=1.9 Hz,10 Hz,1H),7.44-7.41(m,1H),7.38-7.35(m,1H),7.31-7.29(m,2H),7.22-7.20(m,1H),7.19(dd,J=1.5 Hz,4.2 Hz,2H),3.87(s,2H)
Mass,m/e:442(M$^+$),125(base)

Example 23

3-(4-Chloro-3-fluorophenyl)-5-(phenylpropionylamino)-4-(4-pyridyl)-isoxazole $^1$H-NMR(DMSO-d$_6$)δ:10.91(bs,1H),8.52(dd,J=1.5 Hz,4.4 Hz,2H),7.68(t,J=8.0 Hz,1H),7.45(dd,J=1.9 Hz,10 Hz,1H),7.30-7.27(m,2H),7.22-7.18(m,4H),7.09(dd,J=1.5 Hz,4.4 Hz,2H),2.86(t,J=7.3 Hz,2H),2.68(t,J=7.3 Hz,2H)
Mass,m/e:421(M$^+$),91(base)

Example 24

3-(2-Chloro-4-fluorophenyl)-5-(phenylacetylamino)-4-(4-pyridyl)-isoxazole a) 5-Amino-3-(2-chloro-4-fluorophenyl)-4-(4-pyridyl)isoxazole $^1$H-NMR(DMSO-d$_6$)δ:8.36(dd,J=1.6 Hz,4.5 Hz,2H),7.61-7.56(m,2H),7.37(td,J=2.7 Hz,8.5 Hz,1H),6.92(dd,J=1.6 Hz,4.5 Hz,2H)
Mass,m/e:289(M$^+$),63(base)

b) 3-(2-Chloro-4-fluorophenyl)-5-(phenylacetylamino)-4-(4-pyridyl)isoxazole $^1$H-NMR(CDCl$_3$)δ:8.39(dd,J=1.7 Hz,4.4 Hz,2H),7.84(bs,1H),7.45-7.27(m,6H),7.14(dd,J=2.8 Hz,8.4 Hz,1H),7.08(td,J=2.8 Hz,8.4 Hz,1H),6.73(dd,J=1.7 Hz,4.4 Hz,2H),3.78(s,2H)
Mass,m/e:407(M$^+$),91(base)

Example 25

5-[(2-Chlorophenyl)acetylamino]-3-(2-chloro-4-fluorophenyl)-4-(4-pyridyl)isoxazole $^1$H-NMR(CDCl$_3$)δ:8.41(dd,J=1.5 Hz,4.2 Hz,2H),7.89(bs,1H),7.48-7.29(m,5H),7.15(dd,J=2.5 Hz,8.3 Hz,1H),7.09(td,J=2.5 Hz,8.3 Hz,1H),6.84(dd,J=1.5 Hz,4.2 Hz,2H),3.90(s,2H)

Mass,m/e:441(M$^+$),125(base)

Example 26

3-(2-Chloro-4-fluorophenyl)-5-(3-phenylpropionylamino)-4-(4-pyridyl)-isoxazole $^1$H-NMR(CDCl$_3$)δ:8.39(dd,J=1.7 Hz,4.4 Hz,2H),7.99(bs,1H),7.42(dd,J=5.8 Hz,8.5 Hz,1H),7.33-7.27(m,2H),7.24-7.18(m,3H),7.15(dd,J=2.7 Hz,8.5 Hz,1H),7.11-7.06(m,1H),6.81(dd,J=1.7 Hz,4.4 Hz,2H),3.02(t,J=7.3 Hz,2H),2.78(t,J=7.3 Hz,2H)

Mass,m/e:421(M$^+$),91(base)

Example 27

3-(3-Chloro-4-fluorophenyl)-5-(phenylacetylamino)-4-(4-pyridyl)-isoxazole a) 5-Amino-3-(3-chloro-4-fluorophenyl)-4-(4-pyridyl)isoxazole $^1$H-NMR(DMSO-d$_6$)δ:8.45(dd,J=1.6 Hz,4.5 Hz,2H),7.56(dd,J=2.1 Hz,7.1 Hz,1H),7.48(t,J=8.9 Hz,1H),7.35-7.29(m,3H),7.05(dd,J=1.6 Hz,4.5 Hz,2H)

Mass,m/e:289(M$^+$),63(base)

b) 3-(3-Chloro-4-fluorophenyl)-5-(phenylacetylamino)-4-(4-pyridyl)-isoxazole $^1$H-NMR(DMSO-d$_6$)δ:11.10(bs,1H),8.47(dd,J=1.5 Hz,4.6 Hz,2H),7.62(dd,J=2.5 Hz,7.1 Hz,1H),7.50(t,J=8.9 Hz,1H),7.37-7.24(m,6H),7.07(dd,J=1.5 Hz,4.6 Hz,2H),3.68(s,2H)

Mass,m/e:407(M$^+$),91(base)

Example 28

5-[2-(2-Chlorophenyl)acetylamino]-3-(3-chloro-4-fluorophenyl)-4-(4-pyridyl)isoxazole $^1$H-NMR(DMSO-d$_6$)δ:11.15(bs,1H),8.54(dd,J=1.5 Hz,4.4 Hz,2H),7.63(dd,J=2.1 Hz,7.1 Hz,1H),7.50(t,J=8.9 Hz,1H),7.45-7.27(m,5H),7.19(dd,J=1.5 Hz,4.4 Hz,2H),3.87(s,2H)

Mass,m/e:441(M$^+$),125(base)

Example 29

3-(3-Bromo-4-fluorophenyl)-5-(Phenylacetylamino)-4-(4-pyridyl)-isoxazole a) 5-Amino-3-(3-bromo-4-fluorophenyl)-4-(4-pyridyl)isoxazole $^1$H-NMR(CDCl$_3$)δ:8.57(dd,J=1.5 Hz,4.2 Hz,2H),7.72(dd,J=1.9 Hz,6.6 Hz,1H),7.30-7.26(m,1H),7.10(t,J=8.5 Hz,1H),7.05(dd,J=1.5 Hz,4.2 Hz,2H),4.69(bs,2H)

Mass,m/e:333(M$^+$),63(base)

b) 3-(3-Bromo-4-fluorophenyl)-5-(phenylacetylamino)-4-(4-pyridyl)isoxazole $^1$H-NMR(CDCl$_3$)δ:8.51(dd,J=1.5 Hz,4.2 Hz,2H),7.68(dd,J=2.3 Hz,6.6 Hz,1H),7.50(bs,1H),7.42-7.37(m,3H),7.27-7.18(m,3H),7.07(t,J=8.5 Hz,1H),6.90(dd,J=1.5 Hz,4.2 Hz,2H),3.76(s,2H)

Mass,m/e:451(M$^+$),91(base)

Example 30

3-(3-Bromo-4-fluorophenyl)-5-[2-(2-chlorophenyl)acetylamino]-4-(4-pyridyl)isoxazole $^1$H-NMR(CDCl$_3$)δ:8.53(dd,J=1.5 Hz,4.6 Hz,2H),7.69(dd,J=2.3 Hz,6.6 Hz,1H),7.54(bs,1H),7.46-7.43(m,1H),7.34-7.29(m,3H),7.21-7.20(m,1H),7.08(t,J=8.5 Hz,1H),6.99(dd,J=1.5 Hz,4.6 Hz,2H),3.87(s,2H)

Mass,m/e:487(M$^+$),125(base)

Example 31

3-(3-Bromo-4-fluorophenyl)-5-[2-(3-methoxyphenyl)acetylamino]-4-(4-pyridyl)isoxazole $^1$H-NMR(CDCl$_3$)δ:8.52(dd,J=1.5 Hz,4.2 Hz,2H),7.67(dd,J=2.3 Hz,6.4 Hz,1H),7.53(bs,1H),7.31(t,J=7.7 Hz,1H),7.20-7.18(m,1H),7.08(t,J=8.4 Hz,1H),6.90(dd,J=1.5 Hz,4.2 Hz,3H),6.83(d,J=7.7 Hz,1H),6.78(bs,1H),3.80(s,3H),3.72(s,2H)

Mass,m/e:482(M$^+$),121(base)

Example 32

3-(3-Bromo-4-fluorophenyl)-5-(3-phenylpropionylamino)-4-(4-pyridyl)isoxazole $^1$H-NMR(CDCl$_3$)δ:8.53(dd,J=1.5 Hz,4.6 Hz,2H),7.67(dd,J=1.9 Hz,6.6 Hz,1H),7.58(bs,1H),7.32-7.17(m,6H),7.08(t,J=8.1 Hz,1H),6.96(dd,J=1.5 Hz,4.6 Hz,2H),3.01(t,J=7.3 Hz,2H),2.75(t,J=7.3 Hz,2H)

Mass,m/e:465(M$^+$),91(base)

Example 33

5-(Phenylacetylamino)-3-(3,4-dichlorophenyl)-4-(4-pyridyl)isoxazole a) 5-Amino-3-(3,4-dichlorophenyl-4-(4-pyridyl)isoxazole $^1$H-NMR(CDCl$_3$)δ:8.57(dd,J=1.6 Hz,4.5 Hz,2H),7.59(d,J=1.9 Hz,1H),7.43(d,J=8.3 Hz,1H),7.20(dd,J=1.9 Hz,8.3 Hz,1H),7.05(dd,J=1.6 Hz,4.5 Hz,2H),4.89(bs,2H)

Mass,m/e:305(M$^+$),63(base)

b) 5-(Phenylacetylamino)-3-(3,4-dichlorophenyl)-4-(4-pyridyl)-isoxazole $^1$H-NMR(CDCl$_3$)δ:8.51(dd,J=1.5 Hz,4.3 Hz,2H),7.55(bs,1H),7.54(d,J=2.3 Hz,1H),7.42-7.34(m,4H),7.27-7.24(m,2H),7.11(dd,J=1.9 Hz,8.4 Hz,1H),6.90(dd,J=1.6 Hz,4.3 Hz,2H),3.76(s,2H)

Mass,m/e:423(M$^+$),91(base)

Example 34

5-[(2-Chlorophenyl)acetylamino]-3-(3,4-dichlorophenyl)-4-(4-pyridyl)-isoxazole $^1$H-NMR(CDCl$_3$)δ:8.53(dd,J=1.6 Hz,4.5 Hz,2H),7.70(bs,1H),7.56(d,J=2.1 Hz,1H),7.46-7.39(m,2H),7.35-7.28(m,3H),7.13(dd,J=2.1 Hz,8.3 Hz,1H),6.99(dd,J=1.6 Hz,4.5 Hz,2H),3.87(s,2H)
Mass,m/e:457(M$^+$),125(base)

Example 35

3-(3,4-Dichlorophenyl)-5-(3-phenylpropionylamino)-4-(4-pyridyl)-isoxazole $^1$H-NMR(DMSO-d$_6$)δ:8.53(dd,J=1.5 Hz,4.4 Hz,2H),7.72(d,J=8.1 Hz,1H),7.65(d,J=1.9 Hz,1H),7.33-7.25(m,3H),7.24-7.18(m,3H),7.10(dd,J=1.5 Hz,4.4 Hz,2H),2.86(t,J=7.3 Hz,2H),2.68(t,J=7.3 Hz,2H)
Mass,m/e:437(M$^+$),91(base)

Example 36

5-[(2-chlorophenyl)acetylamino]-3-(2,6-dichlorophenyl)-4-(4-pyridyl)-isozazole a) 5-Amino-3-(2,6-dichlorophenyl)-4-(4-pyridyl)isoxazole $^1$H-NMR(DMSO-d$_6$)δ:8.36(dd,J=1.9 Hz,4.6 Hz,2H),7.64-7.54(m,5H),6.90(dd,J=1.9 Hz,4.6 Hz,2H)
Mass,m/e:305(M$^+$),63(base)

b) 5-[(2-Chlorophenyl)acetylamino]-3-(2,6-dichlorophenyl)-4-(4-pyridyl)isozazole $^1$H-NMR(DMSO-d$_6$)δ:11.44(bs,1H),8.44(dd,J=1.7 Hz,4.6 Hz,2H),7.67-7.58(m,3H),7.46-7.40(m,2H),7.33-7.29(m,2H),6.99(dd,J=1.7 Hz,4.6 Hz,2H),3.93(s,2H)
Mass,m/e:457(M$^+$),125(base)

Example 37

3-(2,6-Dichlorophenyl)-5-(3-phenylpropionylamino)-4-(4-pyridyl)-isoxazole $^1$H-NMR(CDCl$_3$)δ:8.38(dd,J=1.5 Hz,4.4 Hz,2H),8.10(bs,1H),7.38-7.18(m,8H),6.86(dd,J=1.5 Hz,4.4 Hz,2H),3.01(t,J=7.3 Hz,2H),2.78(t,J=7.3 Hz,2H)
Mass,m/e:437(M$^+$),91(base)

Example 38

3-(3,5-Dichlorophenyl)-5-(phenylacetylamino)-4-(4-pyridyl)isoxazole a) 5-Amino-3-(3,5-dichlorophenyl)-4-(4-pyridyl)isoxazole $^1$H-NMR(DMSO-d$_6$)δ:8.47(dd,J=1.6 Hz,4.5 Hz,2H),7.75(t,J=1.9 Hz,1H),7.41-7.37(bs,2H),7.35(d,J=1.9 Hz,2H),7.06(dd,J=1.6 Hz,4.5 Hz,2H)
Mass,m/e:305(M$^+$),63(base)

b) 3-(3,5-Dichlorophenyl)-5-(phenylacetylamino)-4-(4-pyridyl)-isoxazole $^1$H-NMR(CDCl$_3$)δ:8.52(dd,J=1.5 Hz,4.4 Hz,2H),7.60(bs,1H),7.42-7.36(m,4H),7.28-7.23(m,4H),6.89(dd,J=1.5 Hz,4.4 Hz,2H),3.76(s,2H)
Mass,m/e:423(M$^+$),91(base)

Example 39

5-[(2-Fluorophenyl)acetylamino]-3-(3,5-dichlorophenyl)-4-(4-pyridyl)-isoxazole $^1$H-NMR(CDCl$_3$)δ:8.53(dd,J=4.5 Hz,6.2 Hz,2H),7.79-7.72(bs,1H),7.42(t,J=1.7 Hz,1H),7.39-7.09(m,6H),6.97(dd,J=4.5 Hz,6.2 Hz,2H),3.77(s,2H)
Mass,m/e:441(M$^+$),109(base)

Example 40

5-[(2-Chlorophenyl)acetylamino]-3-(3,5-dichlorophenyl)-4-(4-pyridyl)-isoxazole $^1$H-NMR(CDCl$_3$)δ:8.55(dd,J=4.4 Hz,6.2 Hz,2H),7.55-7.50(bs,1H),7.47-7.40(m,2H),7.36-7.29(m,3H),7.28-7.24(m,2H),6.99(dd,J=4.4 Hz,6.2 Hz,2H),3.87(s,2H)
Mass,m/e:457(M$^+$),125(base)

Example 41

3-(3,5-Dichlorophenyl)-5-(3-phenylpropionylamino)-4-(4-pyridyl)-isoxazole $^1$H-NMR(CDCl$_3$)δ:8.54(dd,J=1.6 Hz,4.3 Hz,2H),7.56-7.52(bs,1H),7.42(t,J=1.9 Hz,1H),7.33-7.16(m,7H),6.96(dd,J=1.6 Hz,4.3 Hz,2H),3.01(t,J=7.3 Hz,2H),2.75(t,J=7.3 Hz,2H)
Mass,m/e:437(M$^+$),91(base)

Example 42

5-(Phenylacetylamino)-4-(4-pyridyl)-3-(2,3,4-trifluorophenyl)isoxazole a) 5-Amino-4-(4-pyridyl)-3-(2,3,4-trifluorophenyl)isoxazole $^1$H-NMR(CDCl$_3$)δ:8.53(dd,J=1.5 Hz,4.4 Hz,2H),7.23-7.19(m,1H),7.09-7.03(m,1H),6.99(dd,J=1.5H, 4.4 Hz,2H),4.95(bs,2H)
Mass,m/e:291(M$^+$),63(base)

b) 5-(Phenylacetylamino)-4-(4-pyridyl)-3-(2,3,4-trifluorophenyl)-isoxazole $^1$H-NMR(CDCl$_3$)δ:8.45(dd,J=1.5 Hz,4.6 Hz,2H),7.67(bs,1H),7.43-7.35(m,3H),7.30-7.27(m,2H),7.22-7.18(m,1H),7.09-7.05(m,1H),6.80(dd,J=1.5 Hz,4.6 Hz,2H),3.77(s,2H)
Mass,m/e:409(M$^+$),91(base)

Example 43

5-[2-(2-Chlorophenyl)acetylamino]-4-(4-pyridyl)-3-(2,3,4-trifluorophenyl)isoxazole $^1$H-NMR(CDCl$_3$)δ:8.47(dd,J=1.5 Hz,4.2 Hz,2H),7.75(bs,1H),7.35-7.30(m,4H),7.23-7.19(m,1H),7.10-7.03(m,1H),6.90(dd,J=1.5 Hz,4.2 Hz,2H),3.89(s,2H)
Mass,m/e:443(M$^+$),125(base)

Example 44

5-(Phenylacetylamino)-4-(4-pyridyl)-3-(2,4,5-trifluorophenyl)-isoxazole a) 5-Amino-4-(4-pyridyl)-3-(2,4,5-trifluorophenyl)isoxazole $^1$H-NMR(CDCl$_3$)δ:8.53(dd,J=1.5 Hz,4.6 Hz,2H),7.40-7.34(m,1H),7.00-6.92(m,3H),4.94(bs,2H)
Mass,m/e:291(M$^+$),63(base)

b) 5-(Phenylacetylamino)-4-(4-pyridyl)-3-(2,4,5-trifluorophenyl)-isoxazole $^1$H-NMR(CDCl$_3$)δ:8.45(dd,J=1.5 Hz,4.2 Hz,2H),7.63(bs,1H),7.41-7.28(m,7H),6.94-6.88(m,1H),6.80(dd,J=1.5 Hz,4.2 Hz,1H),3.77(s,2H)
Mass,m/e:409(M$^+$),91(base)

Example 45

5-[2-(2-Chlorophenyl)acetylamino]-4-(4-pyridyl)-3-(2,4,5-trifluorophenyl)isoxazole $^1$H-NMR(CDCl$_3$)δ:8.47(dd,J=1.5 Hz,4.6 Hz,2H),7.69(bs,1H),7.47-7.44(m,1H),7.37-7.30(m,4H),6.95-6.89(m,3H) 3.89(s,2H)
Mass,m/e:443(M$^+$),125(base)

Example 46

5-(3-Phenylpropionylamino)-4-(4-pyridyl)-3-(2,4,5-trifluorophenyl)-isoxazol $^1$H-NMR(DMSO-d$_6$)δ:11.00(bs,1H),8.47(dd,J=1.5 Hz,4.4 Hz,2H),7.83-7.66(m,2H),7.32-7.28(m,2H),7.23-7.20(m,3H),7.01(dd,J=1.5 Hz,4.4 Hz,2H),2.88(t,J=7.3 Hz,2H),2.71(t,J=7.3H, 2H)
Mass,m/e:423(M$^+$),91(base)

Example 47

5-(Phenylacetylamino)-4-(4-pyridyl)-3-(2,4,6-trifluorophenyl)isoxazole a) 5-Amino-4-(4-pyridyl)-3-(2,4,6-trifluorophenyl)isoxazole $^1$H-NMR(CDCl$_3$)δ:8.51(dd,J=1.5 Hz,4.6 Hz,2H),7.03-6.64(m,4H),4.96(bs,2H)
Mass,m/e:291(M$^+$),63(base)

b) 5-(Phenylacetylamino)-4-(4-pyridyl)-3-(2,4,6-trifluorophenyl)-isoxazole $^1$H-NMR(CDCl$_3$)δ:8.45(dd,J=1.5 Hz,4.6 Hz,2H),7.53(bs,1H),7.43-7.35(m,3H),7.29-7.27(m,2H),6.81(dd,J=1.5 Hz,4.4 Hz,2H),6.75-6.70(m,2H),3.78(s,2H)
Mass,m/e:409(M$^+$),91(base)

Example 48

5-[2-(2-Chlorophenyl)acetylamino]-4-(4-pyridyl)-3-(2,4,6-trifluorophenyl)isoxazole $^1$H-NMR(CDCl$_3$)δ:8.46(dd,J=1.5 Hz,4.4 Hz,2H),7.77(bs,1H),7.47-7.45(m,1H),7.37-7.30(m,3H),6.91(dd,J=1.5 Hz,4.4 Hz,2H),6.76-6.70(m,2H),3.90(s,2H)
Mass,m/e:443(M$^+$),125(base)

Example 49

5-(3-Phenylpropionylamino)-4-(4-pyridyl)-3-(2,4,6-trifluorophenyl)-isoxazole $^1$H-NMR(DMSO-d$_6$)δ:11.10(bs,1H),8.46(dd,J=1.5 Hz,4.2 Hz,2H),7.44-7.39(m,2H),7.32-7.29(m,2H),7.23-7.20(m,3H),6.98(dd,J=1.5 Hz,4.2 Hz,2H),2.89(t,J=7.3 Hz,2H),2.73(t,J=7.3H, 2H)
Mass,m/e:423(M$^+$),91(base)

Example 50

5-(Phenylacetylamino)-4-(4-pyridyl)-3-(3,4,5-trifluorophenyl)isoxazole a) 5-Amino-4-(4-pyridyl)-3-(3,4,5-trifluorophenyl)isoxazole $^1$H-NMR(CDCl$_3$)δ:8.58(dd,J=1.9 Hz,4.6 Hz,2H),7.09-7.05(m,4H),4.90(bs,2H)
Mass,m/e:291(M$^+$,base)

b) 5-(Phenylacetylamino)-4-(4-pyridyl)-3-(3,4,5-trifluorophenyl)-isoxazole $^1$H-NMR(CDCl$_3$)δ:8.52(dd,J=1.5 Hz,4.4 Hz,2H),7.66(bs,1H),7.41-7.23(m,5H),7.01(dd,J=6.5 Hz,8.0 Hz,2H),6.90(dd,J=1.5 Hz,4.4 Hz,2H),3.74(s,2H)
Mass,m/e:409(M$^+$),91(base)

Example 51

5-[(2-Chlorophenyl)acetylamino]-4-(4-pyridyl)-3-(3,4,5-trifluorophenyl)isoxazole $^1$H-NMR(CDCl$_3$)δ:8.54(dd,J=1.5 Hz,4.4 Hz,2H),7.76(bs,1H),7.44-7.42(m,1H),7.33-7.28(m,3H),7.02(dd,J=6.5 Hz,7.7 Hz,2H),6.99(dd,J=1.5 Hz,4.4 Hz,2H),3.85(s,2H)
Mass,m/e:443(M$^+$),125(base)

Example 52

5-(3-Phenylpropionylamino)-4-(4-pyridyl)-3-(3,4,5-trifluorophenyl)-isoxazole $^1$H-NMR(DMSO-d$_6$)δ:10.93(bs,1H),8.52(dd,J=1.7 Hz,4.4 Hz,2H),7.36(dd,J=6.9 Hz,8.4 Hz,2H),7.30-7.27(m,2H),7.23-7.19(m,3H),7.09(dd,J=1.7 Hz,4.4 Hz,2H),2.86(t,J=7.5 Hz,2H),2.68(t,J=7.5 Hz,2H)
Mass,m/e:423(M$^+$),91(base)

Example 53

3-(2-Methoxyphenyl)-5-(phenylacetylamino)-4-(4-pyridyl)-isoxazole a) 5-Amino-3-(2-methoxyphenyl)-4-(4-pyridyl)isoxazole $^1$H-NMR(CDCl$_3$)δ:8.45(dd,J=4.6 Hz,6.2 Hz,2H),7.49-7.40(m,2H),7.04(td,J=1.0 Hz,7.8 Hz,1H),6.97(dd,J=4.6 Hz,6.2 Hz,2H),6.85(d,J=7.8 Hz,1H),4.88-4.77(bs,2H),3.37(s,3H)

Mass,m/e:267(M$^+$),63(base)

b) 3-(2-Methoxyphenyl)-5-(phenylacetylamino)-4-(4-pyridyl)-isoxazole $^1$H-NMR(CDCl$_3$)δ:8.39(dd,J=1.5 Hz,4.2 Hz,2H),7.53-7.26(m,7H),7.04(td,J=0.8 Hz,7.7 Hz,1H),6.82-6.75(m,3H),3.78(s,2H),3.24(s,3H)

Mass,m/e:385(M$^+$),91(base)

Example 54

5-[(2-Chlorophenyl)acetylamino]-3-(2-methoxyphenyl)-4-(4-pyridyl)-isoxazole $^1$H-NMR(CDCl$_3$)δ:8.40(d,J=6.0 Hz,2H),7.58-7.51(bs,1H),7.50-7.28(m,6H),7.05(t,J=7.3 Hz,1H),6.88(d,J=6.0 Hz,2H),6.80(d,J=8.5 Hz,1H),3.90(s,2H),3.25(s,3H)

Mass,m/e:419(M$^+$),125(base)

Example 55

3-(2-Methoxyphenyl)-5-(3-phenylpropionylamino)-4-(4-pyridyl)-isoxazole $^1$H-NMR(CDCl$_3$)δ:8.42(d,J=5.8 Hz,2H),7.61-7.54(bs,1H),7.50-7.40(m,2H),7.32-7.17(m,5H),7.05(m,1H),6.87(dd,J=1.5 Hz,4.6 Hz,2H),6.80(d,J=8.1 Hz,1H),3.26(s,3H),3.01(t,J=7.3 Hz,2H),2.76(t,J=7.3 Hz,2H)

Mass,m/e:399(M$^+$),91(base)

Example 56

3-(4-Methoxyphenyl)-5-(phenylacetylamino)-4-(4-pyridyl)isoxazole a) 5-Amino-3-(4-methoxyphenyl)-4-(4-pyridyl)isoxazole $^1$H-NMR(CDCl$_3$)δ:8.54(dd,J=1.5 Hz,4.6 Hz,2H),7.35(dt,J=2.5 Hz,8.9 Hz,2H),7.07(dd,J=1.5 Hz,4.6 Hz,2H),6.88(dd,J=2.5 Hz,8.9 Hz,2H),4.76(bs,2H),3.82(s,3H)

Mass,m/e:267(M$^+$),63(base)

b) 3-(4-Methoxyphenyl)-5-(phenylacetylamino)-4-(4-pyridyl)-isoxazole $^1$H-NMR(DMSO-d$_6$)δ:10.99(bs,1H),8.46(dd,J=1.5 Hz,4.2 Hz,2H),7.36-7.24(m,7H),7.06(dd,J=1.5 Hz,4.2 Hz,2H),7.02-6.97(m,2H),3.78(s,3H),3.67(s,2H)

Mass,m/e:385(M$^+$),91(base)

Example 57

5-[(2-Chlorophenyl)acetylamino]-3-(4-methoxyphenyl)-4-(4-pyridyl)-isoxazole $^1$H-NMR(CDCl$_3$)δ:8.50(dd,J=1.5 Hz,4.4 Hz,2H),7.53(bs,1H),7.45-7.42(m,1H),7.35-7.26(m,5H),7.00(dd,J=1.5 Hz,4.4 Hz,2H),6.88-6.84(m,2H),3.87(s,2H),3.81(s,3H)

Mass,m/e:419(M$^+$),125(base)

Example 58

3-(4-Methoxyphenyl)-5-(3-phenylpropionylamino)-4-(4-pyridyl)-isoxazole $^1$H-NMR(CDCl$_3$)δ:8.48(dd,J=1.4 Hz,4.5 Hz,2H),7.77(bs,1H),7.32-7.16(m,7H),6.98(dd,J=1.4 Hz,4.5 Hz,2H),6.88-6.83(m,2H),3.81(s,3H),3.00(t,J=7.4 Hz,2H),2.75(t,J=7.4 Hz,2H)

Mass,m/e:399(M$^+$),91(base)

Example 59

5-[(2-Chlorophenyl)propionylamino]-3-(4-methoxyphenyl)-4-(4-pyridyl)isoxazole $^1$H-NMR(DMSO-d$_6$)δ:10.81(bs,1H),8.51(dd,J=1.5 Hz,4.6 Hz,2H),7.44-7.41(m,1H),7.30-7.24(m,5H),7.09(dd,J=1.5 Hz,4.6 Hz,2H),6.99(d,J=6.6 Hz,2H),3.79(s,3H),2.95(t,J=7.3 Hz,2H),2.69(t,J=7.3 Hz,2H)

Mass,m/e:433(M$^+$),267(base)

Example 60

5-[(3-Chlorophenyl)propionylamino]-3-(4-methoxyphenyl)-4-(4-pyridyl)isoxazole $^1$H-NMR(CDCl$_3$)δ:8.46(d,J=5.8 Hz,2H),7.99(bs,1H),7.28(d,J=8.9 Hz,2H),7.20-7.18(m,3H),7.07-7.05(m,1H),6.99(d,J=5.8 Hz,2H),6.85(d,J=8.9 Hz,2H),3.81(s,3H),2.97(t,J=7.1 Hz,2H),2.74(t,J=7.1 Hz,2H)

Mass,m/e:433(M$^+$),135(base)

Example 61

5-[(4-Chlorophenyl)propionylamino]-3-(4-methoxyphenyl)-4-(4-pyridyl)isoxazole $^1$H-NMR(DMSO-d$_6$)δ:10.77(bs,1H),8.50(dd,J=1.7 Hz,4.4 Hz,2H),7.33(d,J=8.3 Hz,2H),7.28(d,J=8.9 Hz,2H),7.22(d,J=8.3 Hz,2H),7.06(dd,J=1.7 Hz,4.4 Hz,2H),6.99(d,J=8.9 Hz,2H),3.78(s,3H),2.84(t,J=7.3 Hz,2H),2.66(t,J=7.3 Hz,2H)

Mass,m/e:433(M$^+$),125(base)

Example 62

3-(4-Methoxyphenyl)-5-[(2-Methylphenyl)propionylamino]-4-(4-pyridyl)isoxazole $^1$H-NMR(DMSO-d$_6$)δ:10.77(bs,1H),8.51(dd,J=1.5 Hz,4.6 Hz,2H),7.29(d,J=8.9 Hz,2H),7.16-7.10(m,4H),7.08(dd,J=1.5 Hz,4.6 Hz,2H),6.99(d,J=8.9 Hz,2H),3.78(s,3H),2.83(t,J=7.5 Hz,2H),2.62(t,J=7.5 Hz,2H),2.27(s,3H)

Mass,m/e:413(M$^+$),105(base)

Example 63

3-(4-Methoxyphenyl)-5-[(3-methylphenyl)propionylamino]-4-(4-pyridyl)isoxazole $^1$H-NMR(CDCl$_3$)δ:8.47(d,J=5.8 Hz,2H),7.73(bs,1H),7.28(d,J=8.6 Hz,2H),7.17(t,J=7.7 Hz,1H),7.04-7.00(m,3H),6.97(d,J=5.8 Hz,2H),6.85(d,J=8.6 Hz,2H),3.80(s,3H),2.96(t,J=7.3 Hz,2H),2.73(t,J=7.3 Hz,2H),2.31(s,3H)
Mass,m/e:413(M$^+$),105(base)

Example 64

3-(4-Ethoxyphenyl)-5-(phenylacetylamino)-4-(4-pyridyl)isoxazole a) 5-Amino-3-(4-ethoxyphenyl)-4-(4-pyridyl)isoxazole $^1$H-NMR(CDCl$_3$)δ:8.52(dd,J=1.6 Hz,4.5 Hz,2H),7.33(dt,J=2.5 Hz,8.9 Hz,2H),7.07(dd,J=1.6 Hz,4.5 Hz,2H),6.87(dt,J=2.5 Hz,8.9 Hz,2H),4.83(bs,2H),4.04(q,J=6.9 Hz,2H),1.42(t,J=6.9 Hz,3H)
Mass,m/e:281(M$^+$,base)

b) 3-(4-Ethoxyphenyl)-5-(phenylacetylamino)-4-(4-pyridyl)-isoxazole $^1$H-NMR(CDCl$_3$)δ:8.46(dd,J=1.9 Hz,4.6 Hz,2H),7.55(bs,1H),7.40-7.31(m,3H),7.27-7.24(m,4H),6.91(dd,J=1.9 Hz,4.6 Hz,2H),6.83(d,J=8.9 Hz,2H),4.02(q,J=6.9 Hz,2H),3.75(s,2H),1.40(t,J=6.9 Hz,3H)
Mass,m/e:399(M$^+$),91(base)

Example 65

5-(2-Chlorophenylacetylamino)-3-(4-ethoxyphenyl)-4-(4-pyridyl)-isoxazole $^1$H-NMR(DMSO-d$_6$)δ:11.02(bs,1H),8.52(dd,J=1.9 Hz,4.6 Hz,2H),7.44-7.42(m,1H),7.38-7.36(m,1H),7.32-7.27(m,4H),7.16(dd,J=1.9 Hz,4.6 Hz,2H),6.97(d,J=8.9 Hz,2H),4.05(q,J=6.9 Hz,2H),3.75(s,2H),1.32(t,J=6.9 Hz,3H)
Mass,m/e:433(M$^+$),125(base)

Example 66

3-(4-Ethoxyphenyl)-5-(3-phenylpropionylamino)-4-(4-pyridyl)-isoxazole $^1$H-NMR(CDCl$_3$)δ:8.46(dd,J=1.5 Hz,4.4 Hz,2H),7.76(bs,1H),7.30-7.17(m,7H),6.97(dd,J=1.5 Hz,4.4 Hz,2H),6.83(d,J=8.9 Hz,2H),4.02(q,J=6.9 Hz,2H),2.99(t,J=7.5 Hz,2H),2.74(t,J=7.5 Hz,2H),1.40(t,J=6.9 Hz,3H)
Mass,m/e:413(M$^+$),91(base)

Example 67

3-(2-Fluoro-4-methoxyphenyl)-5-(phenylacetylamino)-4-(4-pyridyl)-isoxazole a) 5-Amino-3-(2-fluoro-4-methoxyphenyl)-4-(4-pyridyl)isoxazole $^1$H-NMR(CDCl$_3$)δ:8.49(dd,J=1.5 Hz,4.6 Hz,2H),7.38(t,J=8.2 Hz,1H),7.00(dd, 1.5 Hz,4.6 Hz,2H),6.76(dd,J=6.1 Hz,8.2 Hz,1H),6.61(dd,J=2.7 Hz,11.9 Hz,1H),4.84(bs,2H),3.82(s,3H)
Mass,m/e:285(M$^+$),63(base)

b) 3-(2-Fluoro-4-methoxyphenyl)-5-(phenylacetylamino)-4-(4-pyridyl)isoxazole

Example 68

5-[(2-Chlorophenyl)acetylamino]-3-(2-fluoro-4-methoxyphenyl)-4-(4-pyridyl)isoxazole $^1$H-NMR(DMSO-d$_6$)δ:11.19(bs,1H),8.48(dd,J=1.5 Hz,4.6 Hz,2H),7.48-7.38(m,3H),7.33-7.28(m,2H),7.09(dd,J=1.5 Hz,4.6 Hz,2H),6.94(s,1H),6.91-6.90(m,1H),3.90(s,2H),3.81(s,3H)
Mass,m/e:437(M$^+$),125(base)

Example 69

3-(2-Fluoro-4-methoxyphenyl)-5-(3-phenylpropionylamino)-4-(4-pyridyl)isoxazole $^1$H-NMR(CDCl$_3$)δ:8.37(d,J=5.78 Hz,2H),7.34(t,J=8.0 Hz,1H),7.30-7.17(m,5H),6.88(dd,J=1.5 Hz,4.2 Hz,2H),6.74(dd,J=2.3 Hz,8.48 Hz,1H),6.56(dd,J=2.3 Hz,11.5 Hz,1H),3.79(s,3H),3.00(t,J=7.3 Hz,2H),2.76(t,J=7.3 Hz,2H)
Mass,m/e:417(M$^+$),91(base)

Example 70

3-(4-Fluoro-3-methoxyphenyl)-5-(phenylacetylamino)-4-(4-pyridyl)-isoxazole a) 5-Amino-3-(4-fluoro-3-methoxyphenyl)-4-(4-pyridyl)isoxazole $^1$H-NMR(CDCl$_3$)δ:8.55(dd,J=1.7 Hz,4.4 Hz,2H),7.10-7.01(m,4H),6.91-6.87(m,1H),4.87(s,2H),3.78(s,3H)
Mass,m/e:285(M$^+$),151(base)

b) 3-(4-Fluoro-3-methoxyphenyl)-5-(phenylacetylamino)-4-(4-pyridyl)isoxazole $^1$H-NMR(CDCl$_3$)δ:8.50(dd,J=1.7 Hz,4.4 Hz,2H),7.53(bs,1H),7.42-7.35(m,4H),7.28-7.24(m,1H),7.05-6.98(m,2H),6.92(dd,J=1.7 Hz,4.4 Hz,2H),6.83-6.79(m,1H),3.76(bs,2H),3.75(s,3H)
Mass,m/e:403(M$^+$),91(base)

Example 71

5-[(2-Chlorophenyl)acetylamino]-3-(2-fluoro-4-methoxyphenyl)-4-(4-pyridyl)isoxazole $^1$H-NMR(CDCl$_3$)δ:8.51(dd,J=1.5 Hz,4.2 Hz,2H),7.63(bs,1H),7.46-7.42(m,1H),7.35-7.28(m,3H),7.05-6.99(m,4H),6.85-6.80(m,1H),3.87(s,2H),3.75(s,3H)
Mass,m/e:437(M$^+$),125(base)

Example 72

3-(4-Fluoro-3-methoxyphenyl)-5-(phenylpropionylamino)-4-(4-pyridyl)isoxazole $^1$H-NMR(CDCl$_3$)δ:8.51(dd,J=1.5 Hz,4.6 Hz,2H),7.69(bs,1H),7.32-7.16(m,5H),7.05-7.01(m,2H),6.98(dd,J=1.5 Hz,4.6 Hz,2H),6.84-6.79(m,1H),3.74(s,3H),3.00(t,J=7.3 Hz,2H),2.75(t,J=7.3 Hz,2H)
Mass,m/e:417(M$^+$),91(base)

Example 73

3-(2,3-Dimethoxyphenyl)-5-(phenylacetylamino)-4-(4-pyridyl)-isoxazole a) 5-Amino-3-(2,3-dimethoxyphenyl)-4-(4-pyridyl)isoxazole $^1$H-NMR(CDCl$_3$)δ:8.43(dd,J=1.7 Hz,4.5 Hz,2H),7.09(t,J=7.7 Hz,1H),7.02(dd,J=1.7 Hz,8.5 Hz,1H),6.99(dd,J=1.7 Hz,4.5 Hz,2H),6.92(dd,J=1.7 Hz,7.7 Hz,1H),4.91-4.85(bs,2H),3.86(s,3H),3.59(s,3H)
Mass,m/e:297(M$^+$),51(base)

b) 3-(2,3-Dimethoxyphenyl)-5-(phenylacetylamino)-4-(4-pyridyl)-isoxazole $^1$H-NMR(CDCl$_3$)δ:8.36(dd,J=1.5 Hz,4.6 Hz,2H), 7.65-7.58(bs,1H),7.43-7.33(m,3H),7.29(d,J=6.2 Hz,2H),7.09(t,J=7.8 Hz,1H),7.01(dd,J=1.5 Hz,8.5 Hz,1H),6.90(dd,J=1.5 Hz,7.8 Hz,1H),6.80(dd,J=1.5 Hz,4.6 Hz,2H),3.83(s,3H),3.79(s,2H),3.48(s,3H)
Mass,m/e:415(M$^+$),91(base)

Example 74

5-[(2-Chlorophenyl)acetylamino]-3-(2,3-dimethoxyphenyl)-4-(4-pyridyl)isoxazole $^1$H-NMR(CDCl$_3$)δ:8.38(d,J=5.8 Hz,2H),7.83-7.75(bs,1H),7.50-7.27(m,4H),7.09(t,J=8.0 Hz,1H),7.01(dd,J=1.5 Hz,8.0 Hz,1H),6.94-6.89(m,3H),3.90(s,2H),3.83(s,3H),3.49(s,3H)
Mass,m/e:449(M$^+$),125(base)

Example 75

3-(2,3-Dimethoxyphenyl)-5-(3-phenylpropionylamino)-4-(4-pyridyl)isoxazole $^1$H-NMR(CDCl$_3$)δ:8.37(dd,J=1.5 Hz,4.6 Hz,2H),8.00-7.80(bs,1H),7.32-7.17(m,5H),7.10(t,J=8.5 Hz,1H),7.02(dd,J=1.5 Hz,8.5 Hz,1H),6.91(dd,J=1.5 Hz,7.7 Hz,1H),6.89(dd,J=1.5 Hz,4.6 Hz,2H),3.83(s,3H),3.50(s,3H),3.01(t,J=7.3 Hz,2H),2.76(t,J=7.3 Hz,2H)
Mass,m/e:429(M$^+$),91(base)

Example 76

3-(3,4-Dimethoxyphenyl)-5-(phenylacetylamino)-4-(4-pyridyl)-isoxazole a) 5-Amino-3-(3,4-dimethoxyphenyl)-4-(4-pyridyl)isoxazole $^1$H-NMR(CDCl$_3$)δ:8.55(dd,J=1.5 Hz,4.2 Hz,2H),7.10(dd,J=1.5 Hz,4.2 Hz,2H),6.99(d,J=1.9 Hz,1H),6.93(dd,J=1.9 Hz,8.3 Hz,1H),6.82(d,J=8.3 Hz,1H),4.80(s,2H),3.89(s,3H),3.76(s,3H)
Mass,m/e:297(M$^+$),164(base)

b) 3-(3,4-Dimethoxyphenyl)-5-(phenylacetylamino)-4-(4-pyridyl)-isoxazole $^1$H-NMR(CDCl$_3$)δ:8.50(d,J=4.4 Hz,6.2 Hz,2H),7.42-7.33(m,4H),7.28-7.23(m,2H),6.96-6.93(m,3H),6.85(dd,J=1.9 Hz,8.3 Hz,1H),6.79(d,J=8.3 Hz,1H),3.87(s,3H),3.76(s,2H),3.73(s,3H)
Mass,m/e:415(M$^+$),91(base)

Example 77

5-[(2-Fluorophenyl)acetylamino]-3-(3,4-dimethoxyphenyl)-4-(4-pyridyl)isoxazole $^1$H-NMR(CDCl$_3$)δ:8.51(dd,J=4.4 Hz,6.0 Hz,2H),7.54-7.48(bs,1H),7.39-7.08(m,4H),7.02(dd,J=4.4 Hz,6.0 Hz,2H),6.95(d,J=2.1 Hz,1H),6.87(dd,J=2.1 Hz,8.2 Hz,1H),6.79(d,J=8.2 Hz,1H),3.88(s,3H),3.77(s,2H),3.73(s,3H)
Mass,m/e:433(M$^+$),109(base)

Example 78

5-[(2-Chlorophenyl)acetylamino]-3-(3,4-dimethoxyphenyl)-4-(4-pyridyl)isoxazole $^1$H-NMR(CDCl$_3$)δ:8.51(dd,J=4.6 Hz,6.2 Hz,2H),7.56-7.51(bs,1H),7.47-7.40(m,1H),7.35-7.27(m,3H),7.03(dd,J=4.6 Hz,6.2 Hz,2H),6.94(d,J=1.9 Hz,1H),6.87(dd,J=1.9 Hz,8.3 Hz,1H),6.79(d,J=8.3 Hz,1H),3.87(s,3H),3.87(s,2H),3.73(s,3H)
Mass,m/e:449(M$^+$),125(base)

Example 79

3-(3,4-Dimethoxyphenyl)-5-(3-phenylpropionylamino)-4-(4-pyridyl)-isoxazole $^1$H-NMR(CDCl$_3$)δ:8.53(dd,J=1.6 Hz,4.3 Hz,2H),7.33-7.14(m,5H),7.02(dd,J=1.6 Hz,4.3 Hz,2H),6.94(d,J=1.9 Hz,1H),6.86(dd,J=1.9 Hz,8.5 Hz,1H),6.79(d,J=8.5 Hz,1H),3.88(s,3H),3.73(s,3H),3.00(t,J=7.4 Hz,2H),2.75(t,J=7.4 Hz,2H)
Mass,m/e:429(M$^+$),91(base)

Example 80

3-(2,6-Dimethoxyphenyl)-5-(Phenylacetylamino)-4-(4-pyridyl)-isoxazole $^1$H-NMR(CDCl$_3$)δ:8.35(dd,J=1.5 Hz,4.4 Hz,2H),7.57(bs,1H),7.39-7.28(m,6H),6.79(dd,J=1.5 Hz,4.4 Hz,2H),6.54(d,J=8.5 Hz,2H),3.77(s,2H),3.58(s,6H)
Mass,m/e:415(M$^+$),91(base)

Example 81

5-[2-(2-Chlorophenyl)acetylamino]-3-(2,6-dimethoxyphenyl)-4-(4-pyridyl)isoxazole $^1$H-NMR(DMSO-d$_6$)δ:11.13(bs,1H),8.39(dd-like, 2H),7.47-7.40(m,3H),7.34-7.30(m,2H),6.98(dd,J=1.5 Hz,4.6 Hz,2H),6.75(d,J=8.5 Hz,2H),3.90(s,2H),3.59(s,6H)
Mass,m/e:450(M$^+$),125(base)

Example 82

3-(2,3-Methylenedioxyphenyl)-5-(phenylacetylamino)-4-(4-pyridyl)-isoxazole a) 5-Amino-3-(2,3-methylenedioxyphenyl)-4-(4-pyridyl)isoxazole $^1$H-NMR(CDCl$_3$)δ:8.52(dd,J=1.5 Hz,4.6 Hz,2H),7.08(dd,J=1.5 Hz,4.6 Hz,1H),6.91-6.80(m,4H),5.78(s,2H),4.88(bs,2H)
Mass,m/e:281(M$^+$),63(base)

b) 3-(2,3-Methylenedioxyphenyl)-5-(phenylacetylamino)-4-(4-pyridyl)isoxazole

¹H-NMR(CDCl₃)δ:8.45(dd,J=1.5 Hz,4.6 Hz,2H),7.56(bs,1H),7.41-7.36(m,3H),7.28-7.26(m,2H),6.90-6.81(m,5H),5.70(s,2H),3.77(s,2H)
Mass,m/e:399(M⁺),91(base)

Example 83

3-(2,3-Methylenedioxyphenyl)-5-[2-(2-chlorophenyl)acetylamino]-4-(4-pyridyl)isoxazole ¹H-NMR(CDCl₃)δ:8.47(dd,J=1.5 Hz,4.6 Hz,2H),7.63(bs,1H),7.45-7.43(m,1H),7.35-7.29(m,3H),6.99(dd,J=1.5 Hz,4.6 Hz,2H),6.89-6.81(m,3H),5.71(s,2H),3.88(s,2H)
Mass,m/e:433(M⁺),125(base)

Example 84

3-(3,4-Methylenedioxyphenyl)-5-(phenylacetylamino)-4-(4-pyridyl)-isoxazole a) 5-Amino-3-(3,4-methylenedioxyphenyl)-4-(4-pyridyl)isoxazole ¹H-NMR(DMSO-d₆)δ:8.41(dd,J=1.5 Hz,4.6 Hz,2H),7.18(bs,2H),7.04(dd,J=1.5 Hz,4.6 Hz,2H),6.93(d,J=8.1 Hz,1H),6.82(d,J=1.5 Hz,1H),6.78(dd,J=1.5 Hz,8.1 Hz,1H),6.05(s,2H)
Mass,m/e:281(M⁺),148(base)

b) 3-(3,4-Methylenedioxyphenyl)-5-(phenylacetylamino)-4-(4-pyridyl)isoxazole

¹H-NMR(CDCl₃)δ:8.49(dd,J=1.5 Hz,4.2 Hz,2H),7.62(bs,1H),7.42-7.35(m,3H),7.28-7.24(m,2H),6.92(dd,J=1.5 Hz,4.2 Hz,2H),6.85(d,J=1.5 Hz,1H),6.82(dd,J=1.5 Hz,8.1 Hz,1H),6.76(d,J=8.1 Hz,1H),5.99(s,2H),3.76(s,2H)
Mass,m/e:399(M⁺),91(base)

Example 85

5-[(2-Chlorophenyl)acetylamino]-3-(3,4-methylenedioxyphenyl)-4-(4-pyridyl)isoxazole ¹H-NMR(CDCl₃)δ:11.02(bs,1H),8.52(dd,J=1.4 Hz,4.7 Hz,2H),7.43-7.38(m,1H),7.37-7.33(m,1H),7.32-7.25(m,2H),7.16(dd,J=1.4 Hz,4.7 Hz,2H),6.95(d,J=8.1 Hz,1H),6.89(d,J=1.5 Hz,1H),6.81(dd,J=1.5 Hz,8.1 Hz,1H),6.06(s,2H),3.84(s,2H)
Mass,m/e:433(M⁺),125(base)

Example 86

3-(3,4-Methylenedioxyphenyl)-5-(3-phenylpropionylamino)-4-(4-pyridyl)isoxazole

¹H-NMR(DMSO-d₆)δ:10.78(s,1H),8.51(dd,J=1.5 Hz,4.6 Hz,2H),7.32-7.17(m,5H),7.08(dd,J=1.5 Hz,4.6 Hz,2H),6.97(d,J=8.1 Hz,1H),6.90(d,J=1.5 Hz,1H),6.81(dd,J=1.5 Hz,8.1 Hz,1H),2.86(t,J=7.3 Hz,2H), 2.67(t,J=7.3 Hz,2H)
Mass,m/e:413(M⁺),91(base)

Example 87

3-(3,4-Ethylenedioxyphenyl)-5-(phenylacetylamino)-4-(4-pyridyl)-isoxazole a) 5-Amino-3-(3,4-ethylenedioxyphenyl)-4-(4-pyridyl)isozazle ¹H-NMR(DMSO-d₆)δ:8.44(dd,J=1.6 Hz,4.5 Hz,2H),7.18(bs,2H), 7.06(dd,J=1.6 Hz,4.5 Hz,2H),6.88(d,J=8.3 Hz,1H),6.81(d,J=2.1 Hz,1H),6.76(dd,J=2.1 Hz,8.3 Hz,1H),4.30-4.22(m,4H)
Mass,m/e:295(M⁺),51(base)

b) 3-(3,4-Ethylenedioxyphenyl)-5-(phenylacetylamino)-4-(4-pyridyl)isoxazole

¹H-NMR(CDCl₃)δ:8.22(dd,J=1.5 Hz,4.6 Hz,2H),7.51(bs,1H),7.40-7.32(m,3H),7.25-7.23(m,2H),6.91-6.90(m,3H),6.79(s,2H),4.28-4.21(m,4H),3.74(s,2H)
Mass,m/e:413(M⁺),91(base)

Example 88

5-[(2-Chlorophenyl)acetylamino]-3-(3,4-ethylenedioxyphenyl)-4-(4-pyridyl)isoxazole ¹H-NMR(DMSO-d₆)δ:11.02(bs,1H),8.54(dd,J=1.7 Hz,4.4 Hz,2H),7.44-7.41(m,1H),7.37-7.27(m,3H),7.18(dd,J=1.7 Hz,4.4 Hz,2H),6.90(d,J=8.1 Hz,1H),6.85(d,J=1.9 Hz,1H),6.80(dd,J=1.9 Hz,8.1 Hz,1H),4.28-4.23(m,4H),3.85(s,2H)
Mass,m/e:447(M⁺),125(base)

Example 89

3-(3,4-Ethylenedioxyphenyl)-5-(3-phenylpropionylamino)-4-(pyridyl)-isoxazole

¹H-NMR(DMSO-d₆)δ:10.76(bs,1H),8.51(dd,J=1.5 Hz,4.6 Hz,2H),7.30-7.26(m,2H),7.22-7.18(m,3H),7.08(dd,J=1.7 Hz,4.6 Hz,2H),6.89(d,J=8.1 Hz,1H),6.84(d,J=1.9 Hz,1H),6.78(dd,J=1.9 Hz,8.1 Hz,1H),4.28-4.23(m,4H),2.85(t,J=7.5 Hz,2H),2.65(t,J=7.5 Hz,2H),
Mass,m/e:427(M⁺),91(base)

Example 90

5-(Phenylacetylamino)-4-(4-pyridyl)-3-(3-trifluoromethoxyphenyl)-isoxazole a) 5-Amino-4-(4-pyridyl)-3-(3-trifluoromethoxyphenyl)isozazole ¹H-NMR(CDCl₃)δ:8.56(dd,J=1.5 Hz,4.4 Hz,2H),7.53-7.28(m,4H),7.05(dd,J=1.5 Hz,4.4 Hz,2H),4.89(bs,2H)
Mass,m/e:321(M⁺), 63(base)

b) 5-(Phenylacetylamino)-4-(4-pyridyl)-3-(3-trifluoromethoxy-phenyl)isoxazole

¹H-NMR(CDCl₃)δ:8.50(dd,J=1.5 Hz,4.6 Hz,2H),7.52(bs,1H),7.40-7.23(m,9H),6.89(dd,J=1.5 Hz,4.6 Hz,2H),3.76(s,2H)
Mass,m/e:439(M⁺),91(base)

Example 91

5-[2-(2-Chlorophenyl)acetylamino]-4-(4-pyridyl)-3-(3-trifluoro-methoxyphenyl)isoxazole $^1$H-NMR(CDCl$_3$)δ:8.51(dd,J=1.5 Hz,4.2 Hz,2H),7.65(bs,1H),7.45-7.37(m,2H),7.35-7.24(m,6H),6.98(dd,J=1.5 Hz,4.2 Hz,2H),3.87(s,2H)
Mass,m/e:473(M$^+$),125(base)

Example 92

5-(3-Phenylpropionylamino)-4-(4-pyridyl)-3-(3-trifluoromethoxy-phenyl)isoxazole $^1$H-NMR(CDCl$_3$)δ:8.53(dd,J=1.5 Hz,4.6 Hz,2H),7.53(bs,1H),7.43-7.39(m,2H),7.32-7.17(m,7H),6.97(dd,J=1.5 Hz,4.6 Hz,2H),3.01(t,J=7.3 Hz,2H),2.75(t,J=7.3 Hz,2H)
Mass,m/e:453(M$^+$),91(base)

Example 93

5-(Phenylacetylamino)-4-(4-pyridyl)-3-(4-trifluoromethoxy-phenyl)isoxazole a) 5-Amino-4-(4-pyridyl)-3-(4-trifluoromethoxyphenyl)isoxazole $^1$H-NMR(CDCl$_3$)δ:8.57(dd,J=1.5 Hz,4.5 Hz,2H),7.53-7.40(m,2H),7.19-7.02(m,4H),4.85(bs,2H)
Mass,m/e:321(M$^+$,base)

b) 5-(Phenylacetylamino)-4-(4-pyridyl)-3-(4-trifluoro-methoxyphenyl)isoxazole $^1$H-NMR(CDCl$_3$)δ:8.50(dd,J=1.5 Hz,4.2 Hz,2H),7.59(bs,1H),7.42-7.18(m,9H),6.90(dd,J=1.5 Hz,4.2 Hz,2H),3.75(s,2H)
Mass,m/e:439(M$^+$),91(base)

Example 94

5-[2-(2-Chlorophenyl)acetylamino]-4-(4-pyridyl)-3-(4-trifluoro-methoxyphenyl)isoxazole $^1$H-NMR(CDCl$_3$)δ:8.52(dd,J=1.5 Hz,4.2 Hz,2H),7.56(bs,1H),7.46-7.40(m,3H),7.34-7.29(m,3H),7.21-7.19(m,2H),6.99(dd,J=1.5 Hz,4.2 Hz,2H),3.87(s,2H)
Mass,m/e:473(M$^+$),125(base)

Example 95

3-(2-Methylphenyl)-5-(phenylacetylamino)-4-(4-pyridyl)isoxazole a) 5-Amino-3-(2-methylphenyl)-4-(4-pyridyl)isoxazole $^1$H-NMR(CDCl$_3$)δ:8.42(dd,J=1.6 Hz,4.5 Hz,2H),7.38-7.32(m,1H),7.30-7.21(m,3H),6.89(dd,J=1.6 Hz,4.5 Hz,2H),4.95(s,2H),2.10(s,3H)
Mass,m/e:251(M$^+$),65(base)

b) 3-(2-Methylphenyl)-5-(phenylacetylamino)-4-(4-pyridyl)-isoxazole $^1$H-NMR(CDCl$_3$)δ:8.36(dd,J=4.6 Hz,6.2 Hz,2H),7.66-7.61(bs,1H),7.45-7.28(m,6H),7.24-7.17(m,3H),6.71(dd,J=4.6 Hz,6.2 Hz,2H),3.81(s,2H),2.03(s,3H)
Mass,m/e:369(M$^+$),91(base)

Example 96

5-[(2-Fluorophenyl)acetylamino]-3-(2-methylphenyl)-4-(4-pyridyl)-isoxazole $^1$H-NMR(CDCl$_3$)δ:8.37(dd,J=4.5 Hz,6.2 Hz,2H),7.90-7.80(bs,1H),7.39-7.29(m,4H),7.25-7.10(m,4H),6.80(dd,J=4.5 Hz,6.2 Hz,2H),3.82(s,2H),2.04(s,3H)
Mass,m/e:387(M$^+$),109(base)

Example 97

5-[(2-Chlorophenyl)acetylamino]-3-(2-methylphenyl)-4-(4-pyridyl)-isoxazole $^1$H-NMR(CDCl$_3$)δ:8.38(dd,J=4.6 Hz,6.0 Hz,2H),7.67-7.62(bs,1H),7.49-7.44(m,1H),7.40-7.30(m,4H),7.24-7.18(m,3H),6.82(dd,J=4.6 Hz,6.0 Hz,2H),3.92(s,2H),2.04(s,3H)
Mass,m/e:403(M$^+$),125(base)

Example 98

3-(2-Methylphenyl)-5-(3-phenylpropionylamino)-4-(4-pyridyl)isoxazole $^1$H-NMR(CDCl$_3$)δ:8.38(dd,J=1.6 Hz,4.6 Hz,2H),7.71-7.63(bs,1H),7.38-7.18(m,9H),6.79(dd,J=1.6 Hz,4.6 Hz,2H),3.03(t,J=7.3 Hz,2H),2.80(t,J=7.3 Hz,2H),2.05(s,3H)
Mass,m/e:383(M$^+$),91(base)

Example 99

3-(3-Methylphenyl)-5-(phenylacetylamino)-4-(4-pyridyl)isoxazole a) 5-Amino-3-(3-methylphenyl)-4-(4-pyridyl)isoxazole $^1$H-NMR(CDCl$_3$)δ:8.47(dd,J=1.5 Hz,4.4 Hz,2H),7.27(s,1H),7.22(d,J=5.0 Hz,2H),7.14-7.11(m,1H),7.03(dd,J=1.5 Hz,4.4 Hz,2H),5.06(bs,2H),2.31(s,3H)
Mass,m/e:251(M$^+$),91(base)

b) 3-(3-Methylphenyl)-5-(phenylacetylamino)-4-(4-pyridyl)-isoxazole $^1$H-NMR(CDCl$_3$)δ:8.44(dd,J=1.7 Hz,4.6 Hz,2H),7.68(bs,1H),7.40-7.17(m,8H),7.04(d,J=6.9 Hz,1H),6.88(dd,J=1.7 Hz,4.6 Hz,2H),3.75(s,2H),2.29(s,3H)
Mass,m/e:369(M$^+$),91(base)

Example 100

5-[(2-Chlorophenyl)acetylamino]-3-(3-methylphenyl)-4-(4-pyridyl)-isoxazole $^1$H-NMR(CDCl$_3$)δ:8.46(dd,J=1.7 Hz,4.6 Hz,2H),7.80(bs,1H),7.44-7.41(m,1H),7.34-7.18(m,6H),7.06(d,J=6.9 Hz,1H),6.98(dd,J=1.7 Hz,4.6 Hz,2H),3.87(s,2H),2.30(s,3H)
Mass,m/e:403(M$^+$),125(base)

Example 101

5-[(2-Fluorophenyl)acetylamino]-3-(3-methylphenyl)-4-(4-pyridyl)-isoxazole $^1$H-NMR(CDCl$_3$)δ:8.45(dd,J=1.5 Hz,4.6 Hz,2H),7.96(bs,1H),7.34-7.18(m,8H),6.96(dd,J=1.5 Hz,4.6 Hz,2H),3.77(s,2H),2.30(s,3H)
Mass,m/e:387(M$^+$),109(base)

Example 102

3-(3-Methylphenyl)-5-[(1-phenyl)cyclopropylcarboxyamino]-4-(4-pyridyl)isoxazole $^1$H-NMR(CDCl$_3$)δ:8.48(dd,J=1.7 Hz,4.6 Hz,2H),7.46-7.37(m,6H),7.23-7.17(m,3H),7.04(d,J=6.9 Hz,1H),6.87(dd,J=1.7 Hz,4.6 Hz,2H),2.29(s,3H),1.69(q,J=3.8 Hz,2H),1.23(q,J=3.8 Hz,2H)
Mass,m/e:395(M$^+$),117(base)

Example 103

3-(3-Methylphenyl)-5-(3-phenylpropionylamino)-4-(4-pyridyl)-isoxazole $^1$H-NMR(CDCl$_3$)δ:8.39(dd,J=1.5 Hz,4.6 Hz,2H),8.34(bs,1H),7.30-7.16(m,8H),7.03(d,J=7.3 Hz,1H),6.94(dd,J=1.5 Hz,4.6 Hz,2H),3.00(t,J=7.3 Hz,2H),2.75(t,J=7.3 Hz,2H),2.29(s,3H)
Mass,m/e:383(M$^+$),91(base)

Example 104

5-[(2-Chlorophenyl)propionylamino]-3-(3-methylphenyl)-4-(4-pyridyl)-isoxazole $^1$H-NMR(CDCl$_3$)δ:8.46(d,J=5.9 Hz,2H),7.95(bs,1H),7.35-7.31(m,1H),7.25-7.15(m,6H),7.06(d,J=6.8 Hz,1H),6.99(d,J=5.9 Hz,2H),3.11(t,J=7.4 Hz,2H),2.77(t,J=7.4 Hz,2H),2.30(s,3H)
Mass,m/e:417(M$^+$),251(base)

Example 105

5-[(3-Chlorophenyl)propionylamino]-3-(3-methylphenyl)-4-(4-pyridyl)-isoxazole $^1$H-NMR(CDCl$_3$)δ:8.43(d,J=5.9 Hz,2H),8.18(bs,1H),7.23-7.18(m,6H),7.07-7.04(m,2H),6.97(d,J=5.9 Hz,2H),2.98(t,J=7.4 Hz,2H),2.75(t,J=7.4 Hz,2H),2.30(s,3H)
Mass,m/e:417(M$^+$),251(base)

Example 106

3-(3-Methylphenyl)-5-[(2-methylphenyl)propionylamino]-4-(4-pyridyl)isoxazole $^1$H-NMR(CDCl$_3$)δ:8.44(d,J=6.0 Hz,2H),8.03(bs,1H),7.24-7.18(m,3H),7.15-7.10(m,4H),7.05(d,J=7.03 Hz,1H),6.97(d,J=6.0 Hz,2H),2.99(t,J=7.6 Hz,2H),2.71(t,J=7.6 Hz,2H),2.30(s,3H),2.29(s,3H)
Mass,m/e:397(M$^+$),105(base)

Example 107

3-(3-Methylphenyl)-5-[(3-methylphenyl)propionylamino]-4-(4-pyridyl)isoxazole $^1$H-NMR(CDCl$_3$)δ:8.45(dd,J=1.4 Hz,4.4 Hz,2H),7.79(bs,1H),7.24-7.18(m,3H),7.10-7.04(m,5H),6.95(dd,J=1.4 Hz,4.4 Hz,2H),2.96(t,J=7.3 Hz,2H),2.73(t,J=7.3 Hz,2H),2.32(s,3H),2.30(s,3H)
Mass,m/e:397(M$^+$),105(base)

Example 108

3-(4-Methylphenyl)-5-(phenylacetylamino)-4-(4-pyridyl)isoxazole a) 5-Amino-3-(4-methylphenyl)-4-(4-pyridyl)isoxazole $^1$H-NMR(DMSO-d$_6$)δ:8.40(dd,J=1.6 Hz,4.5 Hz,2H),7.21(s,4H),7.20(bs,1H),7.01(dd,J=1.6 Hz,4.5 Hz,2H),2.33(bs,2H)
Mass,m/e:251(M$^+$),118(base)

b) 3-(4-Methylphenyl)-5-(phenylacetylamino)-4-(4-pyridyl)-isoxazole $^1$H-NMR(CDCl$_3$)δ:8.46(dd,J=1.5 Hz,4.5 Hz,2H),7.67(bs,1H),7.42-7.35(m,3H),7.28-7.22(m,4H),7.15(d,J=7.7 Hz,2H),6.90(dd,J=1.5 Hz,4.4 Hz,2H),3.76(s,2H),2.36(s,3H)
Mass,m/e:369(M$^+$),91(base)

Example 109

5-[(2-Chlorophenyl)acetylamino]-3-(4-methylphenyl)-4-(4-pyridyl)-isoxazole $^1$H-NMR(DMSO-d$_6$)δ:11.04(bs,1H),8.50(dd,J=1.5 Hz,4.4 Hz,2H),7.44-7.34(m,2H),7.31-7.27(m,2H),7.24(s,4H),7.13(dd,J=1.5 Hz,4.4 Hz,2H),3.85(s,2H),2.33(s,3H)
Mass,m/e:403(M$^+$),125(base)

Example 110

3-(4-Methylphenyl)-5-(phenylpropionylamino)-4-(4-pyridyl)isoxazole $^1$H-NMR(CDCl$_3$)δ:8.45(dd,J=1.7 Hz,4.6 Hz,2H),7.82(bs,1H),7.30-7.13(m,9H),6.95(dd,J=1.7 Hz,4.6 Hz,2H),3.00(t,J=7.3 Hz,2H),2.75(t,J=7.3 Hz,2H),2.35(s,3H)
Mass,m/e:383(M$^+$),91(base)

Example 111

3-(4-Ethylphenyl)-5-(phenylacetylamino)-4-(4-pyridyl)isoxazole a) 5-Amino-3-(4-ethylphenyl)-4-(4-pyridyl)isoxazole $^1$H-NMR(CDCl$_3$)δ:8.52(dd,J=1.7 Hz,4.4 Hz,2H),7.33(d,J=8.5 Hz,2H),7.19(d,J=8.5 Hz,2H),7.07(dd,J=1.7 Hz,4.4 Hz,2H),4.83(bs,2H),2.67(q,J=7.6 Hz,2H),1.24(t,J=7.6 Hz,3H)
Mass,m/e:265(M$^+$),132(base)

b) 3-(4-Ethylphenyl)-5-(Phenylacetylamino)-4-(4-pyridyl)-isoxazole $^1$H-NMR(CDCl$_3$)δ:8.46(dd,J=1.5 Hz,4.4 Hz,2H),7.57(bs,1H),7.40-7.33(m,3H),7.27-7.24(m,4H),7.16(d,J=8.1

Hz,2H),6.90(dd,J=1.5 Hz,4.4 Hz,2H),3.75(s,2H),2.65(q,J=7.5 Hz,2H),1.22(t,J=7.5 Hz,3H)
Mass,m/e:383(M+),91(base)

Example 112

5-(2-Chlorophenylacetylamino)-3-(4-ethylphenyl)-4-(4-pyridyl)-isoxazole

¹H-NMR(CDCl₃)δ:8.47(dd,J=1.7 Hz,4.4 Hz,2H),7.71(bs,1H),7.44-7.41(m,1H),7.33-7.26(m,5H),7.16(d,J=8.1 Hz,2H),6.99(dd,J=1.7 Hz,4.4 Hz,2H),3.84(s,2H),2.65(q,J=7.3 Hz,2H),1.22(t,J=7.3 Hz,3H)
Mass,m/e:417(M+),125(base)

Example 113

3-(4-Ethylphenyl)-5-(3-phenylpropionylamino)-4-(4-pyridyl)isoxazole

¹H-NMR(CDCl₃)δ:8.45(dd,J=1.5 Hz,4.4 Hz,2H),7.84(bs,1H),7.30-7.15(m,9H),6.96(dd,J=1.5 Hz,4.4 Hz,2H),3.00(t,J=7.3 Hz,2H),2.75(t,J=7.3 Hz,2H),2.65(q,J=7.7 Hz,2H),1.22(t,J=7.7 Hz,3H)
Mass,m/e:397(M+),91(base)

Example 114

3-(2-Fluoro-5-methylphenyl)-5-(phenylacetylamino)-4-(4-pyridyl)-isoxazole a) 5-Amino-3-(2-fluoro-5-methylphenyl)-4-(4-pyridyl)isoxazole ¹H-NMR(CDCl₃)δ:8.43(dd,J=1.7 Hz,4.6 Hz,2H),7.28(dd,J=1.9 Hz,6.5 Hz,1H),7.23-7.20(m,1H),6.98(dd,J=1.7 Hz,4.6 Hz,2H),6.93(t,J=8.8 Hz,1H),5.11(bs,2H),2.33(s,3H)
Mass,m/e:269(M+),63(base)

b) 3-(2-Fluoro-5-methylphenyl)-5-(phenylacetylamino)-4-(4-pyridyl)isoxazole

¹H-NMR(CDCl₃)δ:8.41(dd,J=1.9 Hz,4.6 Hz,2H),7.57(bs,1H),7.43-7.35(m,3H),7.29-7.27(m,3H),7.24-7.20(m,1H),6.89(dd,J=8.4 Hz,9.2 Hz,1H),6.80(dd,J=1.5 Hz,4.6 Hz,2H),3.77(s,2H),2.33(s,3H)
Mass,m/e:387(M+),91(base)

Example 115

3-(2-Fluoro-5-methylphenyl)-5-(3-phenylpropionylamino)-4-(4-pyridyl)isoxazole

¹H-NMR(CDCl₃)δ:8.36(d,J=5.9 Hz,2H),8.25(bs,1H),7.30-7.17(m,7H),6.90(d,J=9.3 Hz,1H),6.87(d,J=5.9 Hz,2H),3.01(t,J=7.3 Hz,2H),2.76(t,J=7.3 Hz,2H),2.33(s,3H)
Mass,m/e:401(M+),91(base)

Example 116

5-[(2-Chlorophenyl)propionylamino]3-(2-fluoro-5-methylphenyl)-4-(4-pyridyl)isoxazole ¹H-NMR(CDCl₃)δ:8.41(d,J=5.9 Hz,2H),8.03(bs,1H),7.35-7.32(m,1H),7.28(dd,J=1.7 Hz,6.3 Hz,2H),7.25-7.17(m,4H),6.93-6.88(m,3H),3.12(t,J=7.6 Hz,2H),2.78(t,J=7.6 Hz,2H),2.34(s,3H)
Mass,m/e:435(M+),269(base)

Example 117

5-[(3-Chlorophenyl)propionylamino]-3-(2-fluoro-5-methylphenyl)-4-(4-pyridyl)isoxazole ¹H-NMR(CDCl₃)δ:8.41(d,J=5.8 Hz,2H),8.07(bs,1H),7.28(dd,J=1.7 Hz,6.2 Hz,1H),7.23-7.19(m,4H),7.08-7.06(m,1H),6.92-6.88(m,3H),2.99(t,J=7.4 Hz,2H),2.76(t,J=7.4 Hz,2H),2.33(s,3H)
Mass,m/e:435(M+),269(base)

Example 118

3-(2-Fluoro-5-methylphenyl)-5-[(2-methylphenyl)propionylamino]-4-(4-pyridyl)isoxazole ¹H-NMR(CDCl₃)δ:8.49(d,J=6.0 Hz,2H),7.70(bs,1H),7.27(d,J=7.4 Hz,1H),7.16-7.10(m,4H),7.08-7.04(m,1H),6.98(d,J=6.0 Hz,2H),6.95(t,J=8.6 Hz,1H),2.99(t,J=7.6 Hz,2H),2.71(t,J=7.6 Hz,2H),2.29(s,3H),2.22(d,J=1.6 Hz,3H)
Mass,m/e:415(M+),105(base)

Example 119

3-(2-Fluoro-5-methylphenyl)-5-[(3-methylphenyl)propionylamino]-4-(4-pyridyl)isoxazole ¹H-NMR(CDCl₃)δ:8.39(d,J=6.1 Hz,2H),7.99(bs,1H),7.28(dd,J=2.1 Hz,6.8 Hz,1H),7.23-7.20(m,1H),7.11-7.06(m,4H),6.91(d,J=9.3 Hz,1H),6.87(d,J=6.1 Hz,2H),2.97(t,J=7.4 Hz,2H),2.74(t,J=7.4 Hz,2H),2.33(s,3H),2.31(s,3H)
Mass,m/e:415(M+),105(base)

Example 120

3-(3-Fluoro-4-methylphenyl)-5-(phenylacetylamino)-4-(4-pyridyl)-isoxazole a) 5-Amino-3-(3-fluoro-4-methylphenyl)-4-(4-pyridyl)isoxazole ¹H-NMR(CDCl₃) δ :8.51(dd,J=1.5 Hz,4.6 Hz,2H),7.16(t,J=7.7 Hz,1H),7.09(dd,J=1.9 Hz,10.4 Hz,1H),7.06-7.04(m,3H),4.96(bs,2H),2.28(s,3H)
Mass,m/e:269(M+),63(base)

b) 3-(3-Fluoro-4-methylphenyl)-5-(phenylacetylamino)-4-(4-pyridyl)isoxazole

¹H-NMR(CDCl₃)δ:8.46(dd,J=1.7 Hz,4.6 Hz,2H),7.71(bs,1H),7.40-7.33(m,3H),7.26-7.24(m,2H),7.13(t,J=7.7 Hz,1H),7.04(dd,J=1.9 Hz,10 Hz,1H),6.98(dd,J=1.9 Hz,8.1 Hz,1H),6.89(dd,J=1.7 Hz,4.6 Hz,2H),3.75(s,2H),2.27(d,J=1.9 Hz,3H)
Mass,m/e:387(M+),91(base)

Example 121

5-[(2-Chlorophenyl)acetylamino]-3-(3-fluoro-4-methylphenyl)-4-(4-pyridyl)isoxazole H-NMR (DMSO-d₆)δ:11.1(bs,1H),8.53(dd,J=1.5 Hz,4.6 Hz,2H),7.44-7.42(m,1H),7.38-7.34(m,2H),7.32-7.28(m, 2H),7.17(dd,J=1.5 Hz,4.6 Hz,2H),7.15(dd,J=1.5 Hz,8.8 Hz,1H),7.08(dd,J=1.9 Hz,8.0 Hz,1H),3.86(s,2H),2.26(d, J=1.5 Hz,3H)
Mass,m/e:421(M$^+$),125(base)

Example 122

3-(3-Fluoro-4-methylphenyl)-5-(3-phenylpropionylamino)-4-(4-pyridyl)isoxazole $^1$H-NMR(CDCl$_3$)δ:8.46(dd,J=1.7 Hz,4.6 Hz,2H),7.96(bs,1H),7.31-7.27(m,2H),7.24-7.17(m,3H),7.14(t,J=8.0 Hz,1H),7.04(dd,J=1.5 Hz,10 Hz,1H),6.98(dd,J=1.5 Hz,7.7 Hz,1H),6.96(dd,J=1.7 Hz,4.6 Hz,2H),3.00(t,J=7.32 Hz,2H),2.75(t,J=7.32 Hz,2H),2.27(d,J=1.5 Hz,3H)
Mass,m/e:401(M$^+$),91(base)

Example 123

3-(4-Fluoro-3-methylphenyl)-5-(phenylacetylamino)-4-(4-pyridyl)-isoxazole a) 5-Amino-3-(4-fluoro-3-methylphenyl)-4-(4-pyridyl)isoxazole $^1$H-NMR(CDCl$_3$)δ:8.54(dd,J=1.7 Hz,4.4 Hz,2H),7.34-7.30(m,1H),7.16-7.12(m,1H),7.05(dd,J=1.7 Hz,4.4 Hz,2H),6.98(t,J=9.1 Hz,1H),4.84(s,2H),2.24(d,J=1.9 Hz,3H)
Mass,m/e:269(M$^+$),63(base)

b) 3-(4-Fluoro-3-methylphenyl)-5-(phenylacetylamino)-4-(4-pyridyl)isoxazole $^1$H-NMR(CDCl$_3$)δ:8.45(dd,J=1.5 Hz,4.6 Hz,2H),7.60(bs,1H),7.42-7.33(m,3H),7.29-7.22(m,3H),7.08-7.03(m,1H),6.94(t,J=9.1 Hz,1H),6.89(dd,J=1.5 Hz,4.6 Hz,2H),3.76(s,2H),2.22(d,J=1.9 Hz,3H)
Mass,m/e:387(M$^+$),91(base)

Example 124

5-[(2-Chlorophenyl)acetylamino]-3-(4-fluoro-3-methylphenyl)-4-(4-pyridyl)isoxazole $^1$H-NMR(CDCl$_3$)δ:8.49(dd,J=1.7 Hz,4.4 Hz,2H),7.63(bs,1H),7.45-7.42(m,1H),7.35-7.26(m,4H),7.09-7.05(m,1H),6.98(dd,J=1.7 Hz,4.4 Hz,2H),6.95(t,J=8.9 Hz,1H),3.87(s,2H),2.22(d,J=1.9 Hz,3H)
Mass,m/e:421(M$^+$),125(base)

Example 125

3-(4-Fluoro-3-methylphenyl)-5-(3-phenylpropionylamino)-4-(4-pyridyl)isoxazole $^1$H-NMR(CDCl$_3$)δ:8.49(d,J=5.8 Hz,2H),7.69(s,1H),7.32-7.16(m,5H),7.09-7.04(m,1H),6.98-6.94(m,3H),3.01(t,J=7.4 Hz,2H),2.77(t,J=7.4 Hz,2H),2.23(s,3H)
Mass,m/e:401(M$^+$),91(base)

Example 126

5-[(2-Chlorophenyl)propionylamino]-3-(4-fluoro-5-methylphenyl)-4-(4-pyridyl)isoxazole $^1$H-NMR(CDCl$_3$)δ:8.49(dd,J=1.5 Hz,4.4 Hz,2H),7.79(bs,1H),7.35-7.32(m,1H),7.28(dd,J=1.7 Hz,7.2 Hz,1H),7.24-7.17(m,3H),7.08-7.04(m,1H),6.99(dd,J=1.5 Hz,4.4 Hz,2H),6.95(t,J=8.9 Hz,1H),3.11(t,J=7.4 Hz,2H),2.76(t,J=7.4 Hz,2H),2.22(d,J=1.7 Hz,3H)
Mass,m/e:435(M$^+$),269(base)

Example 127

5-[(3-Chlorophenyl)propionylamino]-3-(4-fluoro-5-methylphenyl)-4-(4-pyridyl)isoxazole $^1$H-NMR(CDCl$_3$)δ:8.52(d,J=5.8 Hz,2H),7.53(bs,1H),7.29-7.27(m,1H),7.21-7.18(m,3H),7.09-7.05(m,2H),6.98(d,J=5.8 Hz,2H),6.95(m,1H),2.98(t,J=7.4 Hz,2H),2.74(t,J=7.4 Hz,2H),2.22(d,J=1.7 Hz,3H)
Mass,m/e:435(M$^+$),269(base)

Example 128

3-(4-Fluoro-5-methylphenyl)-5-[(2-methylphenyl)propionylamino]-4-(4-pyridyl)isoxazole $^1$H-NMR(CDCl$_3$)δ:8.39(d,J=6.2 Hz,2H),8.17(bs,1H),7.29(dd,J=2.0 Hz,6.6 Hz,1H),7.23-7.21(m,1H),7.14-7.12(m,4H),6.92-6.88(m,3H),3.00(t,J=7.8 Hz,2H),2.72(t,J=7.8 Hz,2H),2.33(s,3H),2.29(s,3H)
Mass,m/e:415(M$^+$),105(base)

Example 129

3-(4-Fluoro-5-methylphenyl)-5-[(3-methylphenyl)propionylamino]-4-(4-pyridyl)isoxazole $^1$H-NMR(CDCl$_3$)δ:8.48(dd,J=1.3 Hz,4.7 Hz,2H),7.66(bs,1H),7.27(dd,J=1.7 Hz,7.2 Hz,1H),7.11-7.04(m,5H),6.97-6.92(m,3H),2.96(t,J=7.4 Hz,2H),2.72(t,J=7.4 Hz,2H),2.32(s,3H),2.22(d,J=1.7 Hz,3H)
Mass,m/e:415(M$^+$),105(base)

Example 130

3-(4-Chloro-3-methylphenyl)-5-(phenylacetylamino)-4-(4-pyridyl)-isoxazole a) 5-Amino-3-(4-chloro-3-methylphenyl)-4-(4-pyridyl)isoxazole $^1$H-NMR(CDCl$_3$)δ:8.53(dd,J=1.5 Hz,4.6 Hz,2H),7.35(d,J=1.9 Hz,1H),7.31(d,J=8.1 Hz,1H),7.10(dd,J=2.3 Hz,8.5 Hz,1H),7.05(dd,J=1.5 Hz,4.6 Hz,2H),4.87(bs,2H),2.34(s,3H)
Mass,m/e:285(M$^+$),63(base)

b) 3-(4-Chloro-3-methylphenyl)-5-(phenylacetylamino)-4-(4-pyridyl)isoxazole $^1$H-NMR(CDCl$_3$)δ:8.48(dd,J=1.5 Hz,4.2 Hz,2H),7.55(bs,1H),7.42-7.25(m,7H),7.02(dd,J=1.9 Hz,8.1 Hz,1H),6.89(dd,J=1.5 Hz,4.2 Hz,2H),3.76(s,2H),2.32(s,3H)
Mass,m/e:403(M$^+$),91(base)

Example 131

3-(4-Chloro-3-methylphenyl)-5-[(2-chlorophenyl)acetylamino]-4-(4-pyridyl)isoxazole $^1$H-NMR(CDCl$_3$)δ:8.50(dd,J=1.5 Hz,4.4 Hz,2H),7.69(bs,1H),7.46-7.41(m,1H),7.35-7.26(m,5H),7.03(dd,J=1.9 Hz,8.5 Hz,1H),6.98(dd,J=1.5 Hz,4.4 Hz,2H),3.87(s,2H),2.30(s,3H)
Mass,m/e:437(M$^+$),125(base)

Example 132

3-(4-Chloro-3-methylphenyl)-5-(3-phenylpropionylamino)-4-(4-pyridyl)isoxazole $^1$H-NMR(CDCl$_3$)δ:8.48(dd,J=1.6 Hz,4.5 Hz,2H),7.78(bs, 1H),7.32-7.16(m,7H),7.02(dd,J=2.1 Hz,8.3 Hz,1H),6.95(dd, J=1.6 Hz,4.5 Hz,2H),3.01(t,J=7.3 Hz,2H),2.75(t,J=7.3 Hz,2H),2.34(s,3H)
Mass,m/e:417(M$^+$),91(base)

Example 133

3-(4-Methoxy-3-methylphenyl)-5-(phenylacetylamino)-4-(4-pyridyl)-isoxazole a) 5-Amino-3-(4-methoxy-3-methylphenyl)-4-(4-pyridyl)isoxazole $^1$H-NMR(CDCl$_3$)δ:8.52(dd,J=1.7 Hz,4.6 Hz,2H),7.25(m, 1H),7.15(dd,J=2.3 Hz,8.5 Hz,1H),7.07(dd,J=1.7 Hz,4.6 Hz,2H),6.77(d,J=8.5 Hz,1H),4.81(bs,2H),3.83(s,3H),2.17(s, 3H)
Mass,m/e:281(M$^+$),148(base)

b) 3-(4-Methoxy-3-methylphenyl)-5-(phenylacetylamino)-4-(4-pyridyl)isoxazole $^1$H-NMR(CDCl$_3$)δ:8.46(dd,J=1.6 Hz,4.5 Hz,2H),7.57(bs, 1H),7.41-7.32(m,3H),7.28-7.23(m,2H),7.22-7.19(m,1H), 7.06(dd,J=1.9 Hz,8.1 Hz,1H),6.91(dd,J=1.6 Hz,4.5 Hz,2H), 6.73(d,J=8.5 Hz,1H),3.82(s,3H),3.75(s,2H),2.14(s,3H)
Mass,m/e:399(M$^+$),91(base)

Example 134

5-[(2-Chlorophenyl)acetylamino]-3-(4-methoxy-3-methylphenyl)-4-(4-pyridyl)isoxazole $^1$H-NMR(CDCl$_3$)δ:8.48(dd,J=1.5 Hz,4.4 Hz,2H),7.65(bs, 1H),7.45-7.41(m,1H),7.34-7.27(m,3H),7.23-7.21(m,1H), 7.08(dd,J=2.3 Hz,8.7 Hz,1H),7.01(dd,J=1.5 Hz,4.4 Hz,2H), 6.74(d,J=8.7 Hz,1H),3.87(s,2H),3.82(s,3H),2.15(s,3H)
Mass,m/e:433(M$^+$),125(base)

Example 135

3-(4-Methoxy-3-methylphenyl)-5-(3-phenylpropionylamino)-4-(4-pyridyl)isoxazole $^1$H-NMR(CDCl$_3$)δ:8.46(d,J=5.9 Hz,2H),7.74(bs,1H), 7.30-7.17(m,6H),7.06(dd,J=1.9 Hz,8.4 Hz,1H),6.97(d,J=5.9 Hz,2H),6.73(d,J=8.4 Hz,1H),3.82(s,3H),3.00(t,J=7.3 Hz,2H),2.73(t,J=7.3 Hz,2H),2.14(s,3H)
Mass,m/e:413(M$^+$),91(base)

Example 136

3-(2,3-Dimethylphenyl)-5-(phenylacetylamino)-4-(4-pyridyl)isoxazole a) 5-Amino-3-(2,3-dimethylphenyl)-4-(4-pyridyl)isoxazole $^1$H-NMR(CDCl$_3$)δ:8.40(dd,J=1.7 Hz,4.4 Hz,2H),7.24-7.22(m,1H),7.16-7.13(m,2H),6.88(dd,J=1.7 Hz,4.4 Hz,2H), 4.98(bs,2H),2.26(s,3H),1.99(s,3H)
Mass,m/e:265(M$^+$),77(base)

b) 3-(2,3-Dimethylphenyl)-5-(phenylacetylamino)-4-(4-pyridyl)-isoxazole $^1$H-NMR(CDCl$_3$)δ:8.34(dd,J=1.5 Hz,4.4 Hz,2H),7.62(bs, 1H),7.43-7.30(m,5H),7.22(d,J=7.3 Hz,1H),7.12(t,J=7.3 Hz,1H),7.06(d,J=6.9 Hz,1H),6.70(dd,J=1.5 Hz,4.4 Hz,2H), 3.80(s,2H),2.23(s,3H),1.89(s,3H)
Mass,m/e:383(M$^+$),91(base)

Example 137

5-[(2-Chlorophenyl)acetylamino]-3-(2,3-dimethylphenyl)-4-(4-pyridyl)-isoxazole $^1$H-NMR(CDCl$_3$)δ:8.35(dd,J=1.5 Hz,4.6 Hz,2H),8.01(bs, 1H),7.46-7.43(m,1H),7.37-7.35(m,1H),7.33-7.29(m,2H), 7.23(d,J=7.5 Hz,1H),7.12(t,J=7.5 Hz,1H),7.07(d,J=6.5 Hz,1H),6.81(dd,J=1.5 Hz,4.6 Hz,2H),3.91(s,2H),2.23(s,3H), 1.90(s,3H)
Mass,m/e:417(M$^+$),125(base)

Example 138

3-(2,3-Dimethylphenyl)-5-(3-phenylpropionylamino)-4-(4-pyridyl)-isoxazole $^1$H-NMR(CDCl$_3$)δ:8.34(d,J=5.9 Hz,2H),8.00(bs,1H), 7.31-7.19(m,6H),7.12(t,J=7.3 Hz,1H),7.06(d,J=6.9 Hz,1H), 6.78(d,J=5.9 Hz,2H),3.02(t,J=7.3 Hz,2H),2.79(t,J=7.3 Hz,2H),2.23(s,3H),1.91(s,3H)
Mass,m/e:397(M$^+$),91(base)

Example 139

5-[(2-Chlorophenyl)propionylamino]-3-(2,3-dimethylphenyl)-4-(4-pyridyl)isoxazole $^1$H-NMR(CDCl$_3$)δ:8.35(dd,J=1.5 Hz,4.6 Hz,2H),8.19(bs, 1H),7.35-7.31(m,1H),7.27-7.09(m,6H),6.82(dd,J=1.5 Hz,4.6 Hz,2H),3.12(t,J=7.6 Hz,2H),2.80(t,J=7.6 Hz,2H), 2.23(s,3H),1.91(s,3H)
Mass,m/e:431(M$^+$),265(base)

Example 140

5-[(3-Chlorophenyl)propionylamino]-3-(2,3-dimethylphenyl)-4-(4-pyridyl)isoxazole $^1$H-NMR(CDCl$_3$)δ:8.37(d,J=6.0 Hz,2H),7.92(bs,1H), 7.22-7.20(m,4H),7.13(t,J=7.4 Hz,1H),7.10-7.06(m,2H),6.81 (d,J=6.0 Hz,2H),3.00(t,J=7.4 Hz,2H),2.78(t,J=7.4 Hz,2H), 2.24(s,3H),1.92(s,3H)
Mass,m/e:431(M$^+$),265(base)

Example 141

3-(2,4-Dimethylphenyl)-5-[(2-methylphenyl)propionylamino]-4-(4-pyridyl)isoxazole $^1$H-NMR(CDCl$_3$)δ:8.37(d,J=6.0 Hz,2H),7.82(bs,1H), 7.24(d,J=8.6 Hz,2H),7.15-7.07(m,5H),6.81(d,J=6.0 Hz,2H), 3.02(t,J=7.6 Hz,2H),2.75(t,J=7.6 Hz,2H),2.30(s,3H),2.24(s, 3H),1.92(s,3H)
Mass,m/e:411(M$^+$),105(base)

Example 142

3-(2,4-Dimethylphenyl)-5-[(3-methylphenyl)propionylamino]-4-(4-pyridyl)isoxazole $^1$H-NMR(CDCl$_3$)δ:8.35(dd,J=1.7 Hz,4.6 Hz,2H),7.84(bs,1H),7.23(d,J=9.7 Hz,1H),7.15-7.06(m,6H),6.78(dd,J=1.7 Hz,4.6 Hz,2H),2.98(t,J=7.2 Hz,2H),2.76(t,J=7.2 Hz,2H),2.32(s,3H),2.23(s,3H),1.91(s,3H)
Mass,m/e:411(M$^+$),105(base)

Example 143

3-(2,5-Dimethylphenyl)-5-(phenylacetylamino)-4-(4-pyridyl)isoxazole a) 5-Amino-3-(2,5-dimethylphenyl)-4-(4-pyridyl)isoxazole $^1$H-NMR(CDCl$_3$)δ:8.42(dd,J=1.7 Hz,4.4 Hz,2H),7.18-7.08(m,3H),6.90(dd,J=1.7 Hz,4.4 Hz,2H),4.93(bs,2H),2.31(s,3H),2.01(s,3H)
Mass,m/e:266(M$^+$),77(base)

b) 3-(2,5-Dimethylphenyl)-5-(phenylacetylamino)-4-(4-pyridyl)-isoxazole $^1$H-NMR(CDCl$_3$)δ:8.35(dd,J=1.7 Hz,4.6 Hz,2H),7.68(bs,1H),7.43-7.37(m,3H),7.31-7.30(m,2H),7.14(d,J=8.0 Hz,1H),7.08-7.04(m,2H),6.71(dd,J=1.7 Hz,4.6 Hz,2H),3.80(s,2H),2.28(s,3H),1.92(s,3H)
Mass,m/e:383(M$^+$),91(base)

Example 144

5-[(2-Chlorophenyl)acetylamino]-3-(2,5-dimethylphenyl)-4-(4-pyridyl)isoxazole $^1$H-NMR(CDCl$_3$)δ:8.38(d,J=5.9 Hz,2H),7.66(bs,1H),7.48-7.45(m,1H),7.39-7.36(m,1H),7.33-7.31(m,2H),7.15(d,J=8.1 Hz,1H),7.08-7.06(m,2H),6.83(d,J=5.9 Hz,2H),3.80(s,2H),2.28(s,3H),1.92(s,3H)
Mass,m/e:417(M$^+$),125(base)

Example 145

3-(2,5-Dimethylphenyl)-5-(3-phenylpropionylamino)-4-(4-pyridyl)-isoxazole $^1$H-NMR(CDCl$_3$)δ:8.35(dd,J=1.5 Hz,4.6 Hz,2H),7.97(bs,1H),7.32-7.28(m,2H),7.24-7.19(m,3H),7.15(d,J=7.7 Hz,1H),7.09-7.05(m,2H),6.79(dd,J=1.5 Hz,4.6 Hz,2H),3.02(t,J=7.3 Hz,2H),2.78(t,J=7.3 Hz,2H),2.29(s,3H),1.94(s,3H)
Mass,m/e:397(M$^+$),91(base)

Example 146

3-(3,4-Dimethylphenyl)-5-(phenylacetylamino)-4-(4-pyridyl)isoxazole a) 5-Amino-3-(3,4-dimethylphenyl)-4-(4-pyridyl)isoxazole $^1$H-NMR(CDCl$_3$)δ:8.52(dd,J=1.5 Hz,4.5 Hz,2H),7.18-7.03(m,5H),4.83(bs,2H),2.28(s,3H),2.23(s,3H)
Mass,m/e:265(M$^+$),77(base)

b) 3-(3,4-Dimethylphenyl)-5-(phenylacetylamino)-4-(4-pyridyl)isoxazole $^1$H-NMR(CDCl$_3$)δ:8.46(dd,J=1.5 Hz,4.6 Hz,2H),7.51(bs,1H),7.40-7.20(m,6H),7.07(d,J=7.7 Hz,1H),6.98(dd,J=1.5 Hz,7.7 Hz,1H),6.90(dd,J=1.5 Hz,4.6 Hz,2H),3.76(s,2H),2.26(s,3H),2.20(s,3H)
Mass,m/e:383(M$^+$),91(base)

Example 147

5-[2-(2-Fluorophenyl)acetylamino]-3-(3,4-dimethylphenyl)-4-(4-pyridyl)isoxazole $^1$H-NMR(CDCl$_3$)δ:8.48(dd,J=1.5 Hz,4.6 Hz,2H),7.65(bs,1H),7.37-7.26(m,3H),7.21(m,1H),7.18-7.07(m,3H),6.98(dd,J=1.5 Hz,4.6 Hz,2H),3.77(s,2H),2.26(s,3H),2.21(s,3H)
Mass,m/e:401(M$^+$),109(base)

Example 148

5-[2-(2-Chlorophenyl)acetylamino]-3-(3,4-dimethylphenyl)-4-(4-pyridyl)isoxazole $^1$H-NMR(CDCl$_3$)δ:8.48(d,J=6.2 Hz,2H),7.45-7.43(m,1H),7.35-7.29(m,4H),7.21(bs,1H),7.07(d,J=8.1 Hz,1H),7.01-6.99(m,3H),3.87(s,2H),2.26(s,3H),2.21(s,3H)
Mass,m/e:417(M$^+$),125(base)

Example 149

5-[2-(2-Chloro-4-fluorophenyl)acetylamino]-3-(3,4-dimethylphenyl)-4-(4-pyridyl)isoxazole $^1$H-NMR(DMSO-d$_6$)δ:11.05(bs,1H),8.53(dd,J=1.5 Hz,4.4 Hz,2H),7.46-7.41(m,2H),7.22-7.15(m,5H),7.01(dd,J=1.5 Hz,7.7 Hz,1H),3.86(s,2H),2.25(s,3H),2.20(s,3H)
Mass,m/e:435(M$^+$),143(base)

Example 150

3-(3,4-Dimethylphenyl)-5-(3-phenylpropionylamino)-4-(4-pyridyl)-isoxazole $^1$H-NMR(CDCl$_3$)δ:8.49(dd,J=1.5 Hz,4.6 Hz,2H),7.58(bs,1H),7.31-7.17(m,6H),7.08-7.06(m,1H),7.00(d,J=1.5 Hz,1H),6.98(dd,J=1.5 Hz,4.6 Hz,2H),3.00(t,J=7.3 Hz,2H),2.75(t,J=7.3 Hz,2H),2.26(s,3H),2.20(s,3H)
Mass,m/e:397(M$^+$),91(base)

Example 151

3-(3,5-Dimethylphenyl)-5-(phenylacetylamino)-4-(4-pyridyl)isoxazole a) 5-Amino-3-(3,5-dimethylphenyl)-4-(4-pyridyl)isoxazole $^1$H-NMR(CDCl$_3$)δ:8.51(dd,J=1.5 Hz,4.6 Hz,2H),7.06-7.04(m,3H),7.01(s,2H),4.84(bs,2H),2.26(s,6H)
Mass,m/e:265(M$^+$),77(base)

b) 3-(3,5-Dimethylphenyl)-5-(phenylacetylamino)-4-(4-pyridyl)-isoxazole $^1$H-NMR(CDCl$_3$)δ:8.45(dd,J=1.7 Hz,4.6 Hz,2H),7.55(bs,1H),7.41-7.26(m,5H),7.04(s,1H),6.94(s,2H),6.89(dd,J=1.7 Hz,4.6 Hz,2H),3.75(s,2H),2.23(s,6H)
Mass,m/e:383(M$^+$),91(base)

Example 152

5-[(2-Chlorophenyl)acetylamino]-3-(3,5-dimethylphenyl)-4-(4-pyridyl)-isoxazole

$^1$H-NMR(CDCl$_3$)δ:8.47(dd,J=1.5 Hz,4.2 Hz,2H),7.63(bs,1H),7.44-7.42(m,1H),7.33-7.28(m,3H),7.04(s,1H),6.98(dd,J=1.5 Hz,4.2 Hz,2H),6.94(s,2H),3.87(s,2H),2.23(s,6H)

Mass,m/e:417(M$^+$),125(base)

Example 153

3-(3,5-Dimethylphenyl)-5-(3-phenylpropionylamino)-4-(4-pyridyl)-isoxazole

$^1$H-NMR(CDCl$_3$)δ:8.46(dd,J=1.1 Hz,4.6 Hz,2H),7.69(bs,1H),7.31-7.17(m,5H),7.04(s,1H),6.96-6.95(m,4H),3.00(t,J=7.3 Hz,2H),2.75(t,J=7.3 Hz,2H),2.23(s,6H)

Mass,m/e:397(M$^+$),91(base)

Example 154

5-[(2-Chlorophenyl)acetylamino]-3-(2,6-dimethylphenyl)-4-(4-pyridyl)-isoxazole a) 5-Amino-3-(2,6-dimethylphenyl)-4-(4-pyridyl)isoxazole $^1$H-NMR(DMSO-d$_6$)δ:8.28(dd,J=1.9 Hz,4.6 Hz,2H),7.44(bs,2H),7.28(t,J=7.9 Hz,1H),7.14(d,J=7.9 Hz,2H),6.85(dd,J=1.9 Hz,4.6 Hz,2H),2.03(s,6H)

Mass,m/e:265(M$^+$),77(base)

b) 5-[(2-Chlorophenyl)acetylamino]-3-(2,6-dimethylphenyl)-4-(4-pyridyl)isoxazole $^1$H-NMR(CDCl$_3$)δ:8.50(dd,J=1.6 Hz,4.5 Hz,2H),7.73-7.63(m,3H),7.49-7.46(m,2H),7.41-7.37(m,3H),7.29-7.27(m,1H),6.90(dd,J=1.6 Hz,4.5 Hz,2H),3.77(s,2H)

Mass,m/e:423(M$^+$),91(base)

Example 155

5-(Phenylacetylamino)-4-(4-pyridyl)-3-(3-trifluoromethylphenyl)-isoxazole a) 5-Amino-4-(4-pyridyl)-3-(3-trifluoromethylphenyl)isoxazole $^1$H-NMR(CDCl$_3$)δ:8.57(dd,J=1.5 Hz,4.6 Hz,2H),7.79(s,1H),7.70(d,J=7.7 Hz,1H),7.56(d,J=7.7 Hz,1H),7.50(t,J=7.7 Hz,1H),7.06(dd,J=1.5 Hz,4.6 Hz,2H),4.93(bs,2H)

Mass,m/e:305(M$^+$),173(base)

b) 5-(Phenylacetylamino)-4-(4-pyridyl)-3-(3-trifluoromethyl-phenyl)isoxazole $^1$H-NMR(CDCl$_3$)δ:8.50(dd,J=1.6 Hz,4.5 Hz,2H),7.73-7.63(m,3H),7.49-7.46(m,2H),7.41-7.37(m,3H),7.29-7.27(m,1H),6.90(dd,J=1.6 Hz,4.5 Hz,2H),3.77(s,2H)

Mass,m/e:423(M$^+$),91(base)

Example 156

5-[(2-Chlorophenyl)acetylamino]-4-(4-pyridyl)-3-(3-trifluoro-methylphenyl)isoxazole

$^1$H-NMR(DMSO-d$_6$)δ:11.17(bs,1H),8.52(dd,J=1.6 Hz,4.5 Hz,2H),7.88-7.84(m,1H),7.71-7.64(m,3H),7.45-7.40(m,1H),7.38-7.34(m,1H),7.31-7.26(m,2H),7,17(dd,J=1.6 Hz,4.5 Hz,2H),3.87(s,2H)

Mass,m/e:457(M$^+$),125(base)

Example 157

5-[(2-Chlorophenyl)acetylamino]-3-(2-fluoro-3-trifluoromethylphenyl)-4-(4-pyridyl)isoxazole a) 5-Amino-3-(2-fluoro-3-trifluoromethylphenyl)-4-(4-pyridyl)-isoxazole $^1$H-NMR(CDCl$_3$)δ:8.50(dd,J=1.5 Hz,4.4 Hz,2H),7.71(m,2H),7.33(t,J=7.7 Hz,1H),6.97(dd,J=1.5 Hz,4.4 Hz,2H),4.98(bs,2H)

Mass,m/e:323(M$^+$),63(base)

b) 5-[(2-Chlorophenyl)acetylamino]-3-(2-fluoro-3-trifluoromethyl-phenyl)-4-(4-pyridyl)isoxazole $^1$H-NMR(DMSO-d$_6$)δ:11.31(bs,1H),8.48(dd,J=1.5 Hz,4.2 Hz,2H),7.98(t,J=6.9 Hz,1H),7.91(t,J=7.7 Hz,1H),7.58(t,J=7.7 Hz,1H),7.46-7.38(m,2H),7.33-7.28(m,2H),7.10(dd,J=1.5 Hz,4.2 Hz,2H),3.92(s,2H)

Mass,m/e:475(M$^+$),125(base)

Example 158

3-(2-Fluoro-4-trifluoromethylphenyl)-5-(phenylacetylamino)-4-(4-pyridyl)-isoxazole a) 5-Amino-3-(2-fluoro-4-trifluoromethylphenyl)-4-(4-pyridyl)-isoxazole $^1$H-NMR(CDCl$_3$)δ:8.48(dd,J=1.5 Hz,4.6 Hz,2H),7.64(t,J=7.3 Hz,1H),7.50(d,J=8.0 Hz,1H),7.34(d,J=9.6 Hz,1H),6.97(dd,J=1.5 Hz,4.6 Hz,2H),5.13(bs,2H)

Mass,m/e:323(M$^+$),63(base)

b) 3-(2-Fluoro-4-trifluoromethylphenyl)-5-(phenylacetylamino)-4-(4-pyridyl)isoxazole $^1$H-NMR(CDCl$_3$)δ:8.45(dd,J=1.5 Hz,4.2 Hz,2H),7.63(t,J=7.3 Hz,1H),7.54(bs,1H),7.51(d,J=9.25 Hz,1H),7.39-7.38(m,3H),7.32-7.27(m,3H),6.79(dd,J=1.5 Hz,4.2 Hz,2H),3.78(s,2H)

Mass,m/e:441(M$^+$),91(base)

Example 159

5-[(2-Chlorophenyl)acetylamino]-3-(2-fluoro-4-trifluoromethylphenyl)-4-(4-pyridyl)isoxazole

$^1$H-NMR(DMSO-d$_6$)δ:11.29(bs,1H),8.49(dd,J=1.9 Hz,4.6 Hz,2H),7.85-7.82(m,2H),7.77(d,J=8.0 Hz,1H),7.46-7.38(m,2H),7.33-7.30(m,2H),7.12(dd,J=1.9 Hz,4.6 Hz,2H),3.91(s,2H)

Mass,m/e:475(M$^+$),125(base)

Example 160

3-(2-Fluoro-5-trifluoromethylphenyl)-5-(phenylacetylamino)-4-(4-pyridyl)isoxazole a) 5-Amino-3-(2-fluoro-5-trifluoromethylphenyl)-4-(4-pyridyl)-isoxazole $^1$H-NMR(CDCl$_3$)δ:8.51(dd,J=1.5 Hz,4.6 Hz,2H),7.85(dd,J=2.3 Hz,6.1 Hz,1H),7.75-7.71(m,1H),7.18(t,J=8.8 Hz,1H),6.98(dd,J=1.5 Hz,4.6 Hz,2H),4.97(bs,2H)
Mass,m/e:323(M$^+$),63(base)

b) 3-(2-Fluoro-5-trifluoromethylphenyl)-5-(phenylacetylamino)-4-(4-pyridyl)isoxazole $^1$H-NMR(CDCl$_3$)δ:8.45(dd,J=1.7 Hz,4.6 Hz,2H),7.83(dd,J=2.3 Hz,6,1 Hz,1H),7.75-7.71(m,1H),7.53(bs,1H),7.43-7.23(m,5H),7.15(t,J=9.3 Hz,1H),6.80(dd,J=1.7 Hz,4.6 Hz,2H),3.78(s,2H)
Mass,m/e:441(M$^+$),91(base)

Example 161

5-[(2-Chlorophenyl)acetylamino]-3-(2-fluoro-5-trifluoromethylphenyl)-4-(4-pyridyl)isoxazole $^1$H-NMR(CDCl$_3$)δ:8.45(dd,J=1.5 Hz,4.6 Hz,2H),7.83(dd,J=2.3 Hz,5.8 Hz,2H),7.75-7.71(m,1H),7.46-7.44(m,1H),7.36-7.28(m,3H),7.15(t,J=8.8 Hz,1H),6.90(dd,J=1.5 Hz,4.6 Hz,2H),3.89(s,2H)
Mass,m/e:475(M$^+$),125(base)

Example 162

3-(2-Fluoro-5-trifluoromethylphenyl)-5-(3-phenylpropionylamino)-4-(4-pyridyl)isoxazole $^1$H-NMR(CDCl$_3$)δ:8.40(dd,J=1.6 Hz,4.4 Hz,2H),8.19(bs,1H),7.82(dd,J=2.3 Hz,6.1 Hz,1H),7.75-7.71(m,1H),7.32-7.13(m,6H),6.86(dd,J=1.6 Hz,4.4 Hz,2H),3.01(t,J=7.3 Hz,2H),2.77(t,J=7.3 Hz,2H)
Mass,m/e:455(M$^+$),91(base)

Example 163

3-(3-(Fluoro-5-trifluoromethylphenyl)-5-(phenylacetylamino)-4-(4-pyridyl)isoxazole a) 5-Amino-3-(3-fluoro-5-trifluoromethylphenyl)-4-(4-pyridyl)-isoxazole $^1$H-NMR(CDCl$_3$)δ:8.53(dd,J=1.5 Hz,4.4 Hz,2H),7.52(s,1H),7.38(d,J=8.0 Hz,1H),7.29(d,J=8.8 Hz,1H),7.04(dd,J=1.5 Hz,4.4 Hz,2H),5.15(bs,2H)
Mass,m/e:323(M$^+$),63(base)

b) 3-(3-(Fluoro-5-trifluoromethylphenyl)-5-(phenylacetylamino)-4-(4-pyridyl)isoxazole $^1$H-NMR(CDCl$_3$)δ:8.51(m,2H),7.71(bs,1H),7.47(s,1H),7.41-7.37(m,4H),7.26-7.23(m,3H),6.90(dd,J=1.5 Hz,4.2 Hz,2H),3.75(s,2H)
Mass,m/e:441(M$^+$),91(base)

Example 164

5-[(2-Chlorophenyl)acetylamino]-3-(3-fluoro-5-trifluoromethylphenyl)-4-(4-pyridyl)isoxazole $^1$H-NMR(CDCl$_3$)δ:8.52(d,J=5.7 Hz,2H),7.83(bs,1H),7.48(s,1H),7.44-7.42(m,1H),7.38(d,J=8.0 Hz,1H),7.34-7.28(m,3H),7.25(d,J=5.4 Hz,1H),6.99(d,J=5.7 Hz,2H),3.87(s,2H)
Mass,m/e:475(M$^+$),125(base)

Example 165

3-(3-Fluoro-5-trifluoromethylphenyl)-5-(3-phenylpropionylamino)-4-(4-pyridyl)isoxazole $^1$H-NMR(CDCl$_3$)δ:8.49(dd,J=1.7 Hz,4.5 Hz,2H),7.98(bs,1H),7.46(s,1H),7.38(d,J=8.0 Hz,1H),7.31-7.17(m,6H),6.95(dd,J=1.7 Hz,4.5 Hz,2H),3.01(q,J=7.3 Hz,2H),2.76(q,J=7.3 Hz,2H)
Mass,m/e:455(M$^+$),91(base)

Example 166

3-(4-Fluoro-3-trifluoromethylphenyl)-5-(phenylacetylamino)-4-(4-pyridyl)isoxazole a) 5-Amino-3-(4-fluoro-3-trifluoromethylphenyl)-4-(4-pyridyl)-isoxazole $^1$H-NMR(CDCl$_3$)δ:8.57(dd,J=1.5 Hz,4.2 Hz,2H),7.79(dd,J=2.1 Hz,6.7 Hz,1H),7.56-7.51(m,1H),7.19(t,J=9.2 Hz,1H),7.05(dd,J=1.5 Hz,4.2 Hz,2H),4.92(bs,2H)
Mass,m/e:323(M$^+$,base)

b) 3-(4-Fluoro-3-trifluoromethylphenyl)-5-(phenylacetylamino)-4-(4-pyridyl)isoxazole $^1$H-NMR(CDCl$_3$)δ:8.52(dd,J=1.7 Hz,4.4 Hz,2H),7.73(dd,J=2.1 Hz,6.7 Hz,1H),7.54(bs,1H),7.49-7.44(m,1H),7.43-7.36(m,3H),7.28-7.24(m,2H),7.17(t,J=9.2 Hz,1H),6.90(dd,J=1.7 Hz,4.4 Hz,2H),3.76(s,2H)
Mass,m/e:441(M$^+$),91(base)

Example 167

5-[(2-Chlorophenyl)acetylamino]-3-(4-fluoro-3-trifluoromethylphenyl)-4-(4-pyridyl)isoxazole $^1$H-NMR(CDCl$_3$)δ:8.53(dd,J=1.7 Hz,4.4 Hz,2H),7.74(dd,J=2.1 Hz,6.7 Hz,1H),7.69(bs,1H),7.51-7.42(m,2H),7.35-7.28(m,3H),7.17(t,J=9.2 Hz,1H),6.99(dd,J=1.7 Hz,4.4 Hz,2H),3.87(s,2H)
Mass,m/e:475(M$^+$),125(base)

Example 168

3-(3-Fluoro-5-trifluoromethylphenyl)-5-(3-phenylpropionylamino)-4-(4-pyridyl)isoxazole $^1$H-NMR(CDCl$_3$)δ:8.52(dd,J=1.6 Hz,4.5 Hz,2H),7.76-7.71(m,2H),7.50-7.44(m,1H),7.32-7.27(m,2H),7.25-7.16(m,3H),6.96(dd,J=1.6 Hz,4.5 Hz,2H),3.01(t,J=7.3 Hz,2H),2.75(t,J=7.3 Hz,2H)
Mass,m/e:455(M$^+$),91(base)

Example 169

3-(4-Chloro-3-trifluorophenyl)-5-(phenylacetylamino)-4-(4-pyridyl)-isoxazole a) 5-Amino-3-(4-chloro-3-trifluorophenyl)-4-(pyridyl)isoxazl $^1$H-NMR(CDCl$_3$)δ:8.58(dd,J=1.5 Hz,4.5 Hz,2H),7.85(m,1H),7.47(m,2H),7.05(dd,J=1.5 Hz,4.5 Hz,2H),4.90(bs,2H)
Mass,m/e:339(M$^+$),63(base)

b) 3-(4-Chloro-3-trifluorophenyl)-5-(phenylacetylamino)-4-(4-pyridyl)isoxazole $^1$H-NMR(CDCl$_3$)δ:8.53(dd,J=1.5 Hz,4.4 Hz,2H),7.80(d,J=1.9 Hz,1H),7.51(bs,1H),7.47(d,J=8.5 Hz,1H),7.40-7.35(m,4H),7.27-7.24(m,2H),6.90(dd,J=1.5 Hz,4.4 Hz,2H),3.76(s,2H)
Mass,m/e:457(M$^+$),91(base)

Example 170

3-(4-Chloro-3-trifluorophenyl)-5-[2-(2-chlorophenyl)acetylamino]-4-(4-pyridyl)isoxazole $^1$H-NMR(CDCl$_3$)δ:8.54(dd,J=1.5 Hz,4.6 Hz,2H),7.81(d,J=1.9 Hz,1H),7.60(bs,1H),7.49-7.39(m,3H),7.35-7.29(m,3H),6.99(dd,J=1.5 Hz,4.6 Hz,2H),3.87(s,2H)
Mass,m/e:491(M$^+$),125(base)

Example 171

3-(4-Chloro-3-trifluorophenyl)-5-(3-phenylpropionylamino)-4-(4-pyridyl)isoxazole $^1$H-NMR(CDCl$_3$)δ:8.53(dd,J=1.5 Hz,4.2 Hz,2H),7.80(d,J=1.9 Hz,1H),7.75(bs,1H),7.48-7.37(m,2H),7.32-7.17(m,5H),6.96(dd,J=1.5 Hz,4.2 Hz,2H),3.00(t,J=7.3 Hz,2H),2.75(t,J=7.3 Hz,2H)
Mass,m/e:471(M$^+$),91(base)

Example 172

3-(4-Biphenyl)-5-(phenylacetylamino)-4-(4-pyridyl)isoxazole a) 5-Amino-3-(4-biphenyl)-4-(4-pyridyl)isoxazole $^1$H-NMR(CDCl$_3$)δ:8.56(dd,J=1.5 Hz,4.4 Hz,2H), 7.63-7.58(m,4H),7.52-7.42(m,4H),7.39-7.33(m,1H),7.11(dd,J=1.5 Hz,4.4 Hz,2H),4.82(bs,2H)
Mass,m/e:313(M$^+$),152(base)

b) 3-(4-Biphenyl)-5-(phenylacetylamino)-4-(4-pyridyl)isoxazole $^1$H-NMR(CDCl$_3$)δ:8.48(dd,J=1.7 Hz,4.6 Hz,2H),7.61(bs,1H),7.58-7.56(m,4H),7.45-7.34(m,9H),7.28-7.25(m,1H),6.94(dd,J=1.7 Hz,4.6 Hz,2H),3.77(s,2H)
Mass,m/e:431(M$^+$),91(base)

Example 173

5-[(2-Chlorophenyl)acetylamino)]-3-(4-biphenyl)-4-(4-pyridyl)-isoxazole $^1$H-NMR(CDCl$_3$)δ:8.50(dd,J=1.7 Hz,4.6 Hz,2H),7.66(bs,1H),7.57(d,J=8.1 Hz,4H),7.45-7.41(m,5H),7.38-7.28(m,4H),7.04(dd,J=1.7 Hz,4.6 Hz,2H),3.88(s,2H)
Mass,m/e:465(M$^+$),179(base)

Example 174

3-(4-Biphenyl)-5-(3-phenylpropionylamino)-4-(4-pyridyl)isoxazole $^1$H-NMR(DMSO-d$_6$)δ:10.84(bs,1H),8.52(dd,J=1.5 Hz,4.2 Hz,2H),7.75(d,J=8.5 Hz,2H),7.71(d,J=7.3 Hz,2H),7.50-7.44(m,4H),7.39(t,J=7.3 Hz,1H),7.31-7.27(m,2H),7.23-7.20(m,3H),7.12(dd,J=1.5 Hz,4.2 Hz,2H),2.87(t,J=7.5 Hz,2H),2.68(t,J=7.5 Hz,2H)
Mass,m/e:445(M$^+$),91(base)

Example 175

3-(1-Naphthyl)-5-(phenylacetylamino)-4-(4-pyridyl)isoxazole a) 5-Amino-3-(1-naphthyl)-4-(4-pyridyl)isoxazole $^1$H-NMR(CDCl$_3$)δ:8.30(dd,J=1.5 Hz,4.6 Hz,2H),7.97-7.92(m,1H),7.87(d,J=7.7 Hz,1H),7.83(d,J=8.5 Hz,1H),7.51-7.44(m,3H),7.39-7.35(m,1H),6.83(dd,J=1.5 Hz,4.6 Hz,2H),5.02(bs,2H)
Mass,m/e:287(M$^+$,base)

b) 3-(1-Naphthyl)-5-(phenylacetylamino)-4-(4-pyridyl)isoxazole $^1$H-NMR(CDCl$_3$)δ:8.22(dd,J=1.9 Hz,4.6 Hz,2H),7.94(d,J=8.1 Hz,1H),7.86(d,J=8.1 Hz,1H),7.84(bs,1H),7.67(d,J=8.5 Hz,1H),7.49-7.29(m,9H),6.65(dd,J=1.9 Hz,4.6 Hz,2H),3.82(s,2H)
Mass,m/e:405(M$^+$),91(base)

Example 176

5-[(2-Chlorophenyl)acetylamino]-3-(1-naphthyl)-4-(4-pyridyl)-isoxazole $^1$H-NMR(CDCl$_3$)δ:8.25(dd,J=1.5 Hz,4.6 Hz,2H),7.94(d,J=8.1 Hz,1H),7.86(bs,1H),7.86(d,J=8.1 Hz,1H),7.70(d,J=9.2 Hz,1H),7.48-7.30(m,8H),6.77(dd,J=1.5 Hz,4.6 Hz,2H),3.94(s,2H)
Mass,m/e:439(M$^+$),125(base)

Example 177

3-(1-(Naphthyl)-5-(3-phenylpropionylamino)-4-(4-pyridyl)isoxazole $^1$H-NMR(CDCl$_3$)δ:8.23(dd,J=1.5 Hz,4.6 Hz,2H),8.05(bs,1H),7.92(d,J=8.1 Hz,1H),7.86(d,J=8.1 Hz,1H),7.72(d,J=8.1 Hz,1H),7.46(t,J=6.9 Hz,2H),7.41-7.20(m,8H),6.73(dd,J=1.5 Hz,4.6 Hz,1H),3.04(t,J=7.3 Hz,2H),2.81(t,J=7.3 Hz,2H)
Mass,m/e:419(M$^+$),91(base)

Example 178

3-(2-Naphthyl)-5-(phenylacetylamino)-4-(4-pyridyl)isoxazole a) 5-Amino-3-(2-naphthyl)-4-(4-pyridyl)isoxazole $^1$H-NMR(CDCl$_3$)δ:8.52(dd,J=1.6 Hz,4.5 Hz,2H),7.97(s,1H),7.87-7.76(m,3H),7.56-7.44(m,3H),7.08(dd,J=1.6 Hz,4.5 Hz,2H),4.87(bs,2H)
Mass,m/e:287(M$^+$),154(base)

b) 3-(2-Naphthyl)-5-(phenylacetylamino)-4-(4-pyridyl)isoxazole

¹H-NMR(CDCl₃)δ:8.46(dd,J=1.6 Hz,4.3 Hz,2H),7.90-7.72(m,4H),7.63(bs,1H),7.55-7.46(m,2H),7.43-7.34(m,4H),7.30-7.26(m,2H),6.92(dd,J=1.6 Hz,4.3 Hz,2H),3.78(s,2H)
Mass,m/e:405(M⁺),91(base)

Example 179

5-[2-(2-Chlorophenyl)acetylamino]-3-(2-naphthyl)-4-(4-pyridyl)-isoxazole

¹H-NMR(CDCl₃)δ:8.47(dd,J=1.6 Hz,4.5 Hz,2H),7.90(bs,1H),7.85-7.73(m,4H),7.55-7.27(m,7H),7.02(dd,J=1.6 Hz,4.5 Hz,2H),3.89(s,2H)
Mass,m/e:439(M⁺),153(base)

Example 180

3-(2-Naphthyl)-5-(3-phenylpropionylamino)-4-(4-pyridyl)isoxazole

¹H-NMR(CDCl₃)δ:8.45(dd,J=1.5 Hz,4.6 Hz,2H),7.92(bs,1H),7.88(s,1H),7.81(dd,J=8.2 Hz,14.8 Hz,2H),7.73(d,J=8.2 Hz,1H),7.56-7.46(m,2H),7.39(dd,J=1.9 Hz,8.5 Hz,1H),7.32-7.17(m,4H),6.99(dd,J=1.5 Hz,4.6 Hz,2H),3.02(t,J=7.3 Hz,2H), 2.78(t,J=7.3 Hz,2H)
Mass,m/e:419(M⁺),91(base)

Example 181

3-[2-(5-Methylfuryl)]-5-phenylacetylamino-4-(4-pyridyl)isoxazole a) 5-Amino-3-[2-(5-methylfuryl)]-4-(4-pyridyl)isoxazole

¹H-NMR(CDCl₃)δ:8.61(dd,J=4.2 Hz,5.8 Hz,2H),7.26(dd,J=1.7 Hz,4.2 Hz,2H),6.46(d,J=3.5 Hz,1H),6.02(dd,J=3.5 Hz,4.2 Hz,1H),4.82-4.72(bs,2H),2.30(s,3H)
Mass,m/e:241(M⁺),118(base)

b) 3-[2-(5-Methylfuryl)]-5-phenylacetylamino-4-(4-pyridyl)-isoxazole

¹H-NMR(CDCl₃)δ:8.57(dd,J=4.6 Hz,6.2 Hz,2H),7.41-7.31(m,4H),7.24-7.20(m,2H),7.10(dd,J=4.6 Hz,6.2 Hz,2H),6.35(d,J=3.5 Hz,1H),6.01-5.98(m,1H),3.72(s,2H),2.28(s,3H)
Mass,m/e:359(M⁺),91(base)

Example 182

5-[2-(2-Chlorophenyl)acetylamino]-3-[2-(5-methylfuryl)]-4-(4-pyridyl)-isoxazole ¹H-NMR(CDCl₃)δ:8.58(dd,J=4.6 Hz,6.2 Hz,2H),7.53-7.50(bs,1H),7.44-7.40(m,1H),7.33-7.24(m,3H),7.17(dd,J=4.6 Hz,6.2 Hz,2H),6.36(d,J=3.1 Hz,1H),6.02-5.98(m,1H),3.83(s,2H),2.28(s,3H)
Mass,m/e:393(M⁺),125(base)

Example 183

3-[2-(5-Methylfuryl)]-5-(3-phenylpropionylamino)-4-(4-pyridyl)-isoxazole

¹H-NMR(CDCl₃)δ:8.58(dd,J=4.4 Hz,6.2 Hz,2H),7.56-7.50(bs,1H),7.30-7.19(m,5H),7.15(dd,J=4.4 Hz,6.2 Hz,2H),6.34(d,J=3.5 Hz,1H),6.01-5.98(m,1H),2.97(t,J=7.4 Hz,2H),2.71(t,J=7.4 Hz,2H),2.28(s,3H)
Mass,m/e:373(M⁺),91(base)

Example 184

3-(4-Fluorophenyl)-4-[4-(2-fluoropyridyl)]-5-(phenylacetylamino)-isoxazole a) 4-(2-Fluoropyridyl)acetonitrile

A mixture of 1.0 g of 2-fluoro-4-methylpyridine and 2.2 g of t-butoxybisdimethylaminomethane was stirred at 180° C. for 18 hours. The reaction solution was cooled, from which t-butoxybisdimethyl-aminomethane was distilled off under reduced pressure, to provide a dark brown, oily residue. To the residue, 10 mL of water and 2.5 g of hydroxylamine-O-sulfonic acid were added and stirred at room temperature for 30 minutes. The reaction solution was rendered basic by addition of saturated aqueous sodium hydrogencarbonate solution under cooling with ice, and extracted with methylene chloride. The methylene chloride extract was dried over anhydrous magnesium sulfate, and removed of the solvent by reduced pressure distillation to provide 0.93 g (yield, 76%) of the title compound as pale yellow crystals.
¹H-NMR(CDCl₃)δ:8.26(d,J=5.0 Hz,1H),7.20-7.17(m,1H),6.97-6.95(m,1H),3.81(s,2H)
Mass,m/e:136(M⁺,base)

b) 5-Amino-3-(4-fluorophenyl)-4-[4-(2-fluoropyridyl)]isoxazole

In 5 ml of ethanol, 0.132 g of sodium ethoxide was dissolved and into which a solution of 0.39 g of 2-fluoro-4-pyridylacetonitrile in 5 mL of THF was dropped, followed by 20 minutes' stirring under cooling with ice. Then a solution of 0.50 g of 4-fluorobenz-hydroxymoyl chloride in 5 mL of ethanol was added dropwise under cooling with ice, and thereafter stirred at room temperature for 2 hours. After distilling the solvent off from the reaction solution under reduced pressure, water was added, and the precipitated residue was recovered by filtration, washed with water and dried under reduced pressure. The residue was purified on 20 g silica gel column chromatography (eluent, chloroform→chloroform:methanol=100:1) to provide 0.597 g (yield: 76%) of the title compound as light brown crystals.
¹H-NMR(DMSO-d₆)δ:8.05(d,J=5.4 Hz,1H),7.43-7.37(m,4H),7.30-7.24(m,2H),6.86-6.84(m,1H),6.78(bs,1H)
Mass,m/e:273(M⁺),123(base)

c) 3-(4-Fluorophenyl)-4-[4-(2-fluoropyridyl)]-5-(phenylacetyl-amino)isoxazole In 5 mL of THF, 0.180 g of imidazole and 0.43 mL of DBU were dissolved, and while stirring it under cooling with ice, 0.24 mL of phenylacetyl chloride was dropped thereinto, followed by 10 minutes' stirring at room temperature. Then a solution of 0.120 g of 5-amino-3-(4-fluorophenyl)-4-[4-(2-fluoropyridyl)]isoxazole in 4 mL of THF was added dropwise, followed by 8 hours' stirring at room temperature. Distilling the solvent off from the reaction solution under reduced pressure, water was added to the residue, followed by extraction with methylene chloride. The organic layer was dried over anhydrous magnesium sulfate and from which the solvent was distilled off under reduced pressure. The resultant residue was purified on 20 g silica gel column chromatography (eluent, chloroform→chloroform:methanol=50:1) and recrystallized from ether-hexane to provide 0.132 g (yield: 77%) of the title compound as colorless crystals.
$^1$H-NMR(CDCl$_3$)δ:8.10(d,J=5.4 Hz,1H),7.50-7.24(m, 8H),7.10-7.04(m,2H),6.89 (dt,J=1.5 Hz,5.4 Hz,1H),6.57(bs, 1H),3.77(s,2H)
Mass,m/e:391(M$^+$),91(base)

Example 185

5-[2-(2-Chlorophenyl)acetylamino]-3-(4-fluorophenyl)-4-[4-(2-fluoropyridyl)]isoxazole The title compound was synthesized in the manner similar to Example 184.
$^1$H-NMR(CDCl$_3$)δ:8.11(d,J=5.4 Hz,1H),7.53(bs,1H), 7.47-7.45(m,1H),7.37-7.30(m,5H),7.09-7.04(m,2H),6.85 (dt,J=1.5 Hz,5.4 Hz,1H),6.63(bs,1H),3.87(s,2H)
Mass,m/e:425(M$^+$),125(base)

Example 186

4-[4-(2-Bromopyridyl)]-3-(4-fluorophenyl)-5-(phenylacetylamino)-isoxazole a) 4-(2-Bromopyridyl)acetonitrile A mixture of 1.5 g of 2-bromo-4-methylpyridine and 3.0 g of t-butoxybisdimethylaminomethane was stirred at 110° C. for 15 hours. The reaction solution was cooled, and from which t-butoxybisdimethylaminomethane was distilled off under reduced pressure to provide dark brown oily residue. To this residue 20 mL of water and 2.5 g of hydroxylamine-O-sulfonic acid were added and stirred at room temperature for an hour. The crystals precipitated in the reaction solution were recovered by filtration, washed with water, and dried to provide 1.06 g (yield: 62%) of the title compound as brown crystals.
$^1$H-NMR(CDCl$_3$)δ:8.40(d,J=5.0 Hz,1H),7.51(dd,J=0.8 Hz,1.5 Hz,1H),7.27-7.24(m,1H),3.75(s,2H)
Mass,m/e:196(M$^+$),117(base)

b) 5-Amino-4-[4-(2-bromopyridyl)]-3-(4-fluorophenyl)isoxazole

In 5 mL of ethanol, 0.380 g of sodium ethoxide was dissolved, and into which a solution of 1.0 g of 2-bromo-4-pyridylacetonitrile in 10 mL of THF was dropped, followed by 30 minutes' stirring at room temperature. Then a solution of 0.881 g of 4-fluorobenzhydroxymoyl chloride in 5 mL of ethanol was dropped, followed by 5 hours' stirring at room temperature. After distilling the solvent off from the reaction solution under reduced pressure, saturated aqueous ammonium chloride solution was added and extracted with methylene chloride. The methylene chloride extract was dried over anhydrous magnesium sulfate, from which the solvent was distilled off under reduced pressure The resultant residue was purified on 50 g silica gel column chromatography (eluent, chloroform→chloroform:methanol=50:1) to provide 0.77 g (yield: 45%) of the title compound as reddish dark brown crystals.
$^1$H-NMR(CDCl$_3$)δ:8.26(d,J=5.0 Hz,1H),7.41-7.38(m, 2H),7.28(d,J=1.2 Hz,1H),7.11-7.07(m,2H),6.93(dd,J=1.5 Hz,5.0 Hz,1H),4.91(bs,2H)
Mass,m/e:335(M$^+$),123(base)

c) 4-[4-(2-Bromopyridyl)]-3-(4-fluorophenyl)-5-(phenylacetyl-amino)isoxazole

In 3 mL of THF, 0.124 g of imidazole and 0.54 mL of DBU were dissolved, to which 0.23 mL of phenylacetyl chloride was added dropwise under stirring and cooling with ice, followed by 10 minutes' stirring at room temperature. Then a solution of 0.200 g of 5-amino-3-(4-fluorophenyl)-4-[4-(2-bromopyridyl)]isoxazole in 10 mL of THF was added dropwise, followed by 17 hours' stirring at room temperature. Distilling the solvent off from the reaction solution under reduced pressure, water was added to the residue and extracted with methylene chloride. The organic layer was dried over anhydrous magnesium sulfate and from which the solvent was distilled off under reduced pressure. The resultant residue was purified on 10 g silica gel column chromatography (eluent, chloroform→chloroform:methanol=100:1) to provide 0.260 g (yield: 96%) of the title compound as pale yellow crystals.
$^1$H-NMR(CDCl$_3$)δ:8.24(d,J=5.0 Hz,1H),7.44-7.26(m, 8H),7.17(bs,1H),7.10-7.03(m,2H),6.84(dd,J=1.5 Hz,5.0 Hz,1H),3.76(s,2H)
Mass,m/e:453(M$^+$),91(base)

Example 187

3-(4-Fluorophenyl)-4-[4-(2-methoxypyridyl)]-5-(phenylacetylamino)-isoxazole a) 5-Amino-3-(4-fluorophenyl)-4-[4-(2-methoxypyridyl)]isoxazole A mixture of 0.100 g of 5-amino-3-(4-fluorophenyl)-4-[4-(2-fluoropyridyl)]isoxazole, 3 mL of methanol and 0.2 mL of methanol solution containing 28% NaOMe was heated and refluxed under atmosphere of argon for 4.5 hours. After termination of the reaction, the reaction solution was distilled off under reduced pressure. The residue was dissolved in chloroform and washed with saturated aqueous ammonium chloride solution. The organic layer was dried over magnesium sulfate, and from which the solvent was distilled off under reduced pressure. The resultant residue was purified on 5 g silica gel column chromatography (eluent, chloroform:methanol=50:1) to provide 0.162 g (yield: 97%) of the title compound.
$^1$H-NMR(CDCl$_3$)δ:8.08(d,J=5.0 Hz,1H),7.47-7.41(m, 2H),7.11-7.03(m,2H),6.57(dd,J=1.5 Hz,5.2 Hz,1H),6.54(m, 1H),4.78(bs,2H),3.92(s,3H)
Mass,m/e:285(M$^+$,base)

b) 3-(4-Fluorophenyl)-4-[(4-(2-methoxypyridyl)]-5-(phenylacetyl-amino)isoxazole

In 5 mL of THF, 0.050 g of imidazole and 0.22 mL of DBU were dissolved, to which 0.10 mL of phenylacetyl chloride was added dropwise under stirring and cooling with ice, followed by ten minutes' stirring at room temperature. Then a solution of 0.050 g of 5-amino-3-(4-fluorophenyl)-4-[4-(2-methoxypyridyl)]isoxazole in 5 mL of THF was added dropwise, followed by 5 hours' stirring at room temperature. Distilling the solvent off from the reaction solution under reduced pressure, water was added to the residue and extracted with ethyl acetate. The organic layer was dried over anhydrous magnesium sulfate, and from which the solvent was distilled off under reduced pressure. The resultant residue was purified on 10 g silica gel column chromatography (eluent, chloroform→chloroform:methanol=60:1) to provide 0.132 g (yield: 61%) of the title compound as colorless crystals.
$^1$H-NMR(CDCl$_3$)δ:8.05(d,J=5.4 Hz,1H),7.40-7.36(m, 5H),7.30-7.26(m,1H),7.06-7.02(m,2H),6.45(dd,J=1.5 Hz,5.2 Hz,1H),6.39(bs,1H),4.78(bs,2H),3.93(s,3H),3.77(s, 2H)
Mass,m/e:403(M$^+$),91(base)

Example 188

3-(4-Fluorophenyl)-4-[4-(2-methoxypyridyl)]-5-[(2-chlorophenyl)-acetylamino] isoxazole The title compound was synthesized in the manner similar to Example 187.
$^1$H-NMR(CDCl$_3$)δ:8.09-8.05(m,1H),7.45-7.23(m,7H),7.08-7.02(m,2H),6.58-6.52(m,1H),6.47(bs,1H),3.93(s,3H),3.88(s,2H)
Mass,m/e:437(M$^+$),125(base)

Example 189

4-[4-(2-aminopyridyl)]-3-(4-fluorophenyl)-5-(phenylacetylamino)-isoxazole a) 2-[1-(2,4-dimethylpyrrolyl)]-4-methylpyridine To 100 mL of a benzene solution containing 5.00 g of 2-amino-4-methylpyridine and 5.96 g of acetonylacetone, 3.20 mL of acetic acid was added and heated under reflux for 12 hours. Thereafter 2.98 g of acetonylacetone and 1.6 mL of acetic acid were added, followed by further 9 hours' heating under reflux. Then water-methanol was added to the reaction solution and stirred for an hour at room temperature. The crystals precipitated were recovered by filtration and dried under reduced pressure to provide 6.24 g (yield: 73%) of the title compound as light brown crystal.
$^1$H-NMR(CDCl$_3$)δ:8.44(d,J=5.1 Hz,1H),7.20-7.00(m,2H),5.87(s,2H),2.42(s,3H),2.11(s,6H)

b) 2-[1-(2,5-dimethylpyrrolyl)]-4-pyridylacetonitrile

A mixture of 3.0 g of 2-[1-(2,4-dimethylpyrrolyl)]-4-methylpyridine and 8.3 g of t-butoxybisdimethylaminomethane was stirred at 110° C. for 4 hours. The reaction solution was cooled and from which the t-butoxybisdimethylaminomethane was distilled off under reduced pressure, to obtain blackish brown, oily residue. Ten (10) mL of water and 4.6 g of hydroxylamine-O-sulfonic acid were added to the residue and stirred at room temperature for an hour. The reaction solution was rendered basic by addition of saturated aqueous sodium hydrogencarbonate solution under cooling with ice, and extracted with methylene chloride. The methylene chloride extract was dried over anhydrous magnesium sulfate and from which the solvent was distilled off under reduced pressure. The resultant residue was purified on 100 g silica gel column chromatography (eluent, chloroform:methanol=100:1) to provide 2.8 g (yield: 82%) of the title compound as pale yellow crystal.
$^1$H-NMR(CDCl$_3$)δ:8.62(d,J=5.1 Hz,1H),7.40-7.20(m,2H),5.91(s,2H),3.84(s,2H),2.13(s,6H)

c) 5-Amino-3-(4-fluorophenyl)-4-[2-[1-(2,5-dimethylpyrrolyl)]-pyridyl]isoxazole

In 10 mL of ethanol, 0.707 g of sodium ethoxide was dissolved, and into which 10 mL of THF solution containing 1.1 g of 2-[1-(2,5-dimethylpyrrolyl)]-4-pyridylacetonitrile was dropped, followed by 30 minutes' stirring at room temperature. Then 10 mL of an ethanol solution containing 0.900 g of 4-fluorobenzhydroxymoyl chloride was added dropwise, followed by 2 hours' stirring at room temperature. The solvent was distilled off under reduced pressure, and saturated aqueous ammonium chloride solution was added to the residue, followed by extraction with methylene chloride. The organic layer was dried over anhydrous magnesium chloride and from which the solvent was distilled off under reduced pressure. The resultant residue was purified on 50 g silica gel column chromatography (eluent, chloroform:methanol=50:1) to provide 0.96 g (yield: 53%) of the title compound as pale brown crystal.
$^1$H-NMR(CDCl$_3$)δ:8.55(d,J=5.0 Hz,1H),7.44-7.40(m,2H),7.12-7.06(m,3H),6.89(d,J=1.5 Hz,1H),5.85(s,2H),4.88(bs s,2H),2.01(s,6H)
Mass,m/e:348(M+base)

d) 3-(4-Fluorophenyl)-4-[4-[2-[1-(2,5-dimethylpyrrolyl)]pyridyl]]-5-(phenylacetylamino)isoxazole To a mixture of 0.080 g of imidazole and 3 mL of THF, first 0.17 mL of DBU and then 0.15 mL of phenylacetyl chloride was added and stirred at room temperature for 15 minutes. Five (5) mL of THF solution containing 0.10 g of 5-amino-3-(4-fluorophenyl)-4-[4-[2-[1-(2,5-dimethylpyrrolyl)]pyridyl]]isoxazole and 0.17 mL of DBU was added, followed by 2 hours' stirring at room temperature. Water was added to the reaction solution which was then extracted with methylene chloride. The extract was washed first with saturated aqueous NaHCO$_3$ solution and then with saturated brine, dried over anhydrous magnesium sulfate and from which the solvent was distilled off under reduced pressure. The resultant residue was purified on 10 g silica gel column chromatography (eluent, chloroform→chloroform:methanol=50:1) and washed with ether to provide 0.037 g (yield: 27%) of the crystalline title compound.
$^1$H-NMR(CDCl$_3$)δ:8.49(dd,J=0.8 Hz,5.1 Hz,1H),7.39-7.33(m,6H),7.23-7.21(m,2H),7.07-7.03(m,2H),6.93(dd,J=1.5 Hz,5.1 Hz,1H),6.83(bs,1H),5.86(s,2H),3.74(s,2H),2.00(s,6H)
Mass,m/e:466(M$^+$),91(base)

e) 4-[4-(2-Aminopyridyl)]-3-(4-fluorophenyl)-5-(phenylacetyl-amino)isoxazole

A mixture of 0.032 g of 3-(4-fluorophenyl)-4-[2-[1-(2,5-dimethylpyrrolyl)]pyridyl]]-5-(phenylacetylamino)isoxazole, 0.058 g of hydroxylamine hydrochloride, 1 mL of ethanol and 1 mL of water was stirred at room temperature for 19 hours. The reaction solution was cooled, from which the solvent was distilled off under reduced pressure and water was added to the residue, followed by extraction with chloroform. The chloroform extract was washed with saturated brine, dried over anhydrous magnesium sulfate, and from which the solvent was distilled off under reduced pressure. The resultant residue was purified on 10 g silica gel column chromatography (eluent, chloroform→chloroform:methanol=50:1) to provide 0.011 g (yield: 41%) of the crystalline title compound.
$^1$H-NMR(CDCl$_3$)δ:7.93(d,J=5.4 Hz,1H),7.42-7.35(m,5H),7.29-7.26(m,3H),7.06-7.02(m,2H),6.20(dd,J=1.5 Hz,5.4 Hz,1H),6.05(bs,1H),4.39(bs,2H),3.79(s,2H)
Mass,m/e:388(M$^+$),91(base)

In the following, the compounds of Examples 190-193 were synthesized in the manner similar to Example 189.

Example 190

4-[4-(2-Aminopyridyl)]-5-[2-(2-chlorophenyl)acetylamino]-3-(4-fluorophenyl)isoxazole $^1$H-NMR(CDCl$_3$)δ:7.93(d,J=5.4 Hz,1H),7.44-7.40(m,3H),7.35-7.28(m,3H),7.26-23(m,1H),7.07-7.02(m,2H),6.28(dd,J=1.5 Hz,5.4 Hz,1H),6.21(bs,1H),4.53(bs,2H),3.89(s,2H)
Mass,m/e:422(M$^+$),125(base)

Example 191

4-[4-(2-Aminopyridyl)]-5-[2-(2,6-dichlorophenyl)acetylamino]-3-(4-fluorophenyl)isoxazole $^1$H-NMR(DMSO-d$_6$)δ:11.03(bs,1H),7.88(d,J=5.4 Hz,1H),7.49-7.46(m,4H),7.36-7.28(m,3H),6.32(dd,J=1.5 Hz,5.4 Hz,1H),6.21(bs,1H),5.93(bs,2H),4.04(s,2H)
Mass,m/e:456(M$^+$),159(base)

Example 192

4-[4-(2-Aminopyridyl)]-5-[2-(2,4-dichlorophenyl)acetylamino]-3-(4-fluorophenyl)isoxazole $^1$H-NMR(CDCl$_3$)δ:7.96(d,J=5.4 Hz,1H),7.45-7.41(m,3H),7.25(bs,3H),7.05(t,J=8.9 Hz,2H),6.31(dd,J=1.5 Hz,5.4 Hz,1H),6.22(bs,1H),4.48(bs,2H),3.86(s,2H)
Mass,m/e:456(M$^+$),159(base)

Example 193

4-[4-(2-Aminopyridyl)]-3-(4-fluorophenyl)-5-[2-methyl-2-phenyl-(acetylamino)]isoxazole $^1$H-NMR(CDCl$_3$)δ:7.87(d,J=5.4 Hz,1H),7.41-7.27(m,8H),7.04(t,J=8.9 Hz,2H),6.13(d,J=5.4 Hz,1H),5.96(bs,1H),4.50(bs,2H),3.81-3.74(m,1H),1.57 and 1.55(s,3H)
Mass,m/e:402(M$^+$),105(base)

Example 194

4-[4-(2-Dimethylaminopyridyl)]-3-(4-fluorophenyl)-5-(phenylacetyl-amino)isoxazole A mixture of 80 mg of 4-[4-(2-bromopyridyl)]-3-(4-fluoro-phenyl)-5-(phenylacetylamino)isoxazole and 0.3 mL of HMPA was stirred at 200° C. for 50 minutes. The solvent was distilled off from the reaction solution under reduced pressure. The resultant residue was purified on thin-layer chromatography (developer, chloroform:methanol=100:1) to provide 2 mg (yield: 3%) of the title compound.
$^1$H-NMR(CDCl$_3$) δ: 8.05(d,J=5.7 Hz,1H),7.53-6.93(m,10H),6.13-6.07(m,2H),3.77(s,2H),2.95(s,6H)
Mass,m/e:416(M$^+$),91(base)

Example 195

4-[4-(2-Dimethylaminopyridyl)]-3-(4-fluorophenyl)-5-[2-methyl-2-phenyl(acetylamino)] isoxazole The title compound was synthesized in the manner similar to Example 194.
$^1$H-NMR(CDCl$_3$)δ:8.01(dd,J=0.8 Hz,5.0 Hz,1H),7.45-7.40(m,2H),7.37-7.31(m,4H),7.26-7.22(m,2H),7.05-7.00(m,2H),6.06(bs,1H),6.03(dd,J=1.2 Hz,5.0 Hz,1H),3.79(bs,1H),2.93(s,6H),1.54(d,J=7.3 Hz,3H)
Mass,m/e:430(M$^+$),105(base)

Example 196

5-[(2-Chlorophenyl)acetylamino]-3-(4-fluorophenyl)-4-[4-(2-methylpyridyl)]isoxazole a) 4-Chloromethyl-2-methylpyridine Into 100 mL of methylene chloride solution containing 2.16 g of 4-(2-methylpyridyl)methanol (cf. PCT International Publication WO98/21210 Pamphlet), 23 mL of thionyl chloride was dropped at room temperature, followed by 20 hours' stirring at room temperature. The solvent was distilled off from the reaction solution under reduced pressure, and the residue was extracted with methylene chloride, after addition of saturated aqueous NaHCO$_3$ solution. The methylene chloride extract was dried over anhydrous magnesium sulfate, and from which the solvent was distilled off under reduced pressure to provide 2.46 g (yield: 100%) of brown crystalline title compound.
$^1$H-NMR(CDCl$_3$)δ:8.45(d,J=5.0 Hz,1H),7.31(s,1H),7.25(d,J=5.0 Hz,1H),4.74(s,2H),2.48(s,3H)
Mass,m/e:141(M$^+$,base)

b) 4-(2-Methylpyridyl)acetonitrile

To 10 mL of DMSO solution containing 1.7 g of sodium cyanide, 3 mL of DMSO solution containing 2.46 g of 4-chloromethyl-2-methylpyridine was added under cooling with ice, and stirred at room temperature for 3 hours. After addition of water, the reaction solution was extracted with ethyl acetate. The ethyl acetate extract was washed with water, dried over anhydrous magnesium sulfate and removed of the solvent by reduced pressure distillation to provide 1.86 g (yield: 80%) of the title compound which was a reddish brown, oily substance.
$^1$H-NMR(CDCl$_3$)δ:8.43(d,J=5.0 Hz,1H),7.22(s,1H),7.16(d,J=5.0 Hz,1H),4.08(s,2H),2.47(s,3H)
Mass,m/e:132(M$^+$,base)

c) 5-Amino-3-(4-fluorophenyl)-4-[4-(2-methylpyridyl)]isoxazole

To 3.3 mL of 28% sodium methoxide-methanol solution, 15 mL of methanol and 15 mL of THF solution containing 1.86 g of 4-(2-methylpyridyl)acetonitrile were added and stirred at room temperature for 30 minutes. Then 15 mL of a methanol solution containing 2.9 g of 4-fluorobenzhydroxymoyl chloride was added, followed by 30 minutes' stirring at room temperature. The solvent was distilled off from the reaction solution under reduced pressure, and the residue was extracted with a mixed solvent of chloroform:methanol=1:1, after addition of water. The organic layer was dried over anhydrous magnesium sulfate and removed of the solvent by reduced pressure distillation. The resultant residue was purified on 100 g silica gel column chromatography (eluent, chloroform:methanol=100:1→20:1) to provide 0.955 g (yield: 25%) of the title compound as reddish brown crystals.
$^1$H-NMR(CDCl$_3$)δ:8.41(d,J=5.2 Hz,1H),7.32(dd,J=5.4 Hz,8.6 Hz,2H),7.05(t,J=8.6 Hz,2H),6.93(bs,1H),6.83(dd,J=1.5 Hz,5.2 Hz,1H),4.80(bs,2H),2.50(s,3H)
Mass,m/e:269(M$^+$,base)

d) 5-[(2-Chlorophenyl)acetylamino]-3-(4-fluorophenyl)-4-[4-(2-methylpyridyl)]isoxazole To 5 mL of THF solution containing 0.21 g of 2-chlorophenyl-acetic acid, 0.2 g of CDI was added and stirred at room temperature for an hour. Then 10 mL of THF solution containing 0.1 g of 5-amino-3-(4-fluorophenyl)-4-[4-(2-methylpyridyl)]isoxazole and 0.4 mL of DBU were added and stirred for 12 hours. After distilling the solvent off from the reaction solution under reduced pressure, water was added to the residue, followed by extraction with ethyl acetate. The ethyl acetate extract was dried over anhydrous magnesium sulfate and from which the solvent was distilled off under reduced pressure. The resultant residue was purified on 15 g silica gel column chromatography (eluent, chloroform: methanol=100:1) to provide 0.12 g (yield: 77%) of the colorless crystalline title compound.

¹H-NMR(CDCl₃)δ:8.38(d,J=5.2 Hz,1H),7.55(bs,1H), 7.44-7.42(m,1H),7.38-7.28(m,5H),7.04(t,J=8.4 Hz,2H),6.87 (s,1H),6.77(dd,J=1.1 Hz,5.2 Hz,1H),3.87(s,2H),2.47(s,3H)

Mass,m/e:421(M⁺), 125(base)

Example 197

3-(4-Fluorophenyl)-4-[4-(2-methylpyridyl)]-5-(3-phenylpropionyl-amino)isoxazole

The title compound was synthesized in the manner similar to Example 196.

¹H-NMR(CDCl₃)δ:8.38(d,J=5.0 Hz,1H),7.66(bs,1H), 7.35(dd,J=5.3 Hz,8.6 Hz,2H),7.29-7.16(m,5H),7.03(t,J=8.6 Hz,2H),6.86(s,1H),6.78(d,J=5.0 Hz,1H),3.00(t,J=7.3 Hz,2H),2.75(t,J=7.3 Hz,2H),2.46(s,3H)

Mass,m/e:401(M⁺), 91(base)

Example 198

4-[4-(2,6-Dimethylpyridyl)]-3-(4-fluorophenyl)-5-phenylacetylamino-isoxazole a) 4-Chloromethyl-2,6-dimethylpyridine To 45 mL of methylene chloride solution containing 1.0 g of 4-(2,6-dimethylpyridyl)methanol (cf. PCT International Publication WO98/21210 Pamphlet), thionyl chloride was added dropwise at room temperature, followed by 21 hours' stirring. The solvent was distilled off from the reaction solution under reduced pressure, and to the residue saturated aqueous NaHCO₃ solution was added, followed by extraction with methylene chloride. The organic layer was dried over anhydrous magnesium sulfate and removed of the solvent by reduced pressure distillation to provide 1.0 g (yield: 88%) of the title compound as a yellow oily substance.

¹H-NMR(CDCl₃)δ:6.95(s,2H),4.43(s,2H),2.50(s,6H)

Mass,m/e:155(M⁺,base)

b) 4-(2,6-Dimethylpyridyl)acetonitrile

To 4 mL of DMSO solution containing 0.63 g of sodium cyanide, 1 mL of DMSO solution containing 1.00 g of 4-chloromethyl-2,6-dimethylpyridine was added under cooling with ice, and stirred at room temperature for 2 hours. Water was added to the reaction solution which was then extracted with ethyl acetate. The ethyl acetate extract was washed with water, dried over anhydrous magnesium sulfate and removed of the solvent by reduced pressure distillation to provide 0.86 g (yield: 92%) of the title compound as a reddish brown, oily substance.

¹H-NMR(CDCl₃)δ:7.01(s,2H),4.02(s,2H),2.49(s,6H)

Mass,m/e:146(M⁺,base)

c) 5-Amino-4-[4-(2,6-dimethylpyridyl)]-3-(4-fluorophenyl)isoxazole

To 1.4 mL of 28% sodium methoxide-methanol solution, 7 mL of THF solution containing 0.86 g of 4-(2,6-dimethylpyridyl)-acetonitrile was added and stirred at room temperature for 20 minutes. Then 7 mL of methanol solution containing 1.23 g of 4-fluorobenzhydroxymoyl chloride was added and stirred at room temperature for 13 hours. The solvent was distilled off from the reaction solution under reduced pressure, and water was added to the residue, followed by extraction with chloroform. The organic layer was dried over anhydrous magnesium sulfate and removed of the solvent by reduced pressure distillation. The resultant residue was purified on 80 g silica gel column chromatography (eluent, chloroform:methanol=100:1→40:1) to provide 0.425 g (yield: 25%) of reddish brown, crystalline title compound.

¹H-NMR(CDCl₃)δ:7.41(dd,J=5.4 Hz,8.4 Hz,2H),7.04(t, J=8.4 Hz,2H),6.72(s,2H),4.78(bs,2H),2.45(s,6H)

Mass,m/e:283(M⁺,base)

d) 4-[4-(2,6-Dimethylpyridyl)]-3-(4-fluorophenyl)-5-phenylacetyl-aminoisoxazole

To 8 mL of THF solution containing 90 mg of imidazole and 0.4 mL of DBU, 0.16 mL of phenylacetyl chloride was added under cooling with ice, and stirred for an hour at room temperature. Then 8 mL of THF solution containing 0.1 g of 5-amino-4-[4-(2,6-dimethylpyridyl)]-3-(4-fluorophenyl) isoxazole was added, followed by 3 days' stirring. The solvent was distilled off from the reaction solution under reduced pressure, and to the resultant residue water was added, followed by extraction with ethyl acetate. The ethyl acetate extract was dried over anhydrous magnesium sulfate and removed of the solvent by reduced pressure distillation. The resultant residue was purified on 15 g silica gel column chromatography (eluent, chloroform:methanol=100:1) and then on thin-layer chromatography (developer, chloroform: methanol=100:1) to provide 53 mg (yield: 37%) of yellow crystalline title compound.

¹H-NMR(CDCl₃)δ:7.38-7.23(m,8H),7.03(t,J=8.4 Hz,2H),6.56(s,2H),3.76(s,2H),2.42(s,6H)

Mass,m/e:401(M⁺), 91(base)

In the following, the compounds of Examples 199-200 were synthesized in the manner similar to Example 198.

Example 199

5-[(2-Chlorophenyl)acetylamino]-4-[4-(2,6-dimethylpyridyl)]-3-(4-fluorophenyl)isoxazole ¹H-NMR(DMSO-d₆)δ:11.02(bs,1H),7.45-7.42(m,3H), 7.39-7.36(s,1H),7.33-7.27(m,4H),6.82(s,2H),3.86(s,2H), 2.35(s,6H)

Mass,m/e:435(M⁺), 125(base)

Example 200

4-[4-(2,6-Dimethylpyridyl)]-3-(4-fluorophenyl)-5-(3-phenylpropionyl-amino)isoxazole ¹H-NMR(CDCl₃)δ:7.40(bs,1H),7.37(dd,J=5.3 Hz,8.8 Hz,2H),7.29-7.27(m,2H),7.22-7.16(m,3H),7.03(t,J=8.8 Hz,2H),6.69(s,2H),3.00(t,J=7.3 Hz,2H),2.76(m,2H),2.46(s, 6H)

Mass,m/e:415(M⁺),91(base)

Formulation Example 1

Tablet:

|  | mg/tablet |
| --- | --- |
| Active ingredient | 5.0 |
| Starch | 10.0 |

-continued

|  | mg/tablet |
|---|---|
| Lactose | 73.0 |
| Carboxymethyl cellulose calcium | 10.0 |
| Talc | 1.0 |
| Magnesium stearate | 1.0 |
|  | 100.0 |

The active ingredient is pulverized to a grain size not greater than 70 μm, and to which starch, lactose and carboxymethyl cellulose calcium are added and thoroughly mixed. Ten (10) % starch paste is added to the mixture, mixed by stirring and granulated. After drying, the granules are dressed to around 1000 μm in particle size. Mixing talc and magnesium stearate therewith, the blend is tabletted.

The invention claimed is:

1. An isoxazole compound represented by formula (I)

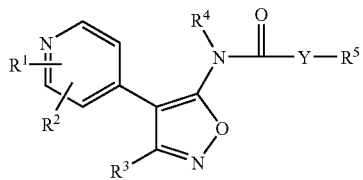

where in the formula,
R¹ and R² each independently stands for hydrogen, halogen, lower alkyl, lower alkoxy, amino, lower alkylamino, di-lower alkyl-amino, phenyl-lower alkylamino, acylamino, lower alkylthio or lower alkylsulfinyl,
R³ stands for a group represented by the following formula (A)

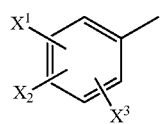

wherein X¹, X² and X³ each independently stands for hydrogen, halogen, lower alkyl, lower haloalkyl, lower alkoxy, lower haloalkoxy, hydroxyl, lower alkanoyl, lower haloalkanoyl or phenyl,
R⁴ stands for hydrogen or lower alkyl,
R⁵ stands for phenyl, which may be optionally substituted with 1-3 substituents selected from halogen, lower alkyl, lower haloalkyl, lower alkoxy, hydroxyl, lower alkanoyl, lower haloalkanoyl, lower alkylthiocarbonyl, lower haloalkylthio-carbonyl, amino, lower alkylamino, di-lower alkylamino and nitro, Y stands for —(CH₂)ₙ—, —CO—, —CH(CH₃)—, —C(CH₃)₂—, —O—, —NH— or

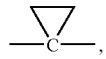

wherein n is an integer of 1-3, with the proviso that, where both of R¹ and R² stand for hydrogen and two of X¹, X² and X³ stand for hydrogen, the remaining one of X¹, X² and X³ is a group other than hydrogen atom or halogen atom,
or a pharmaceutically acceptable salt thereof.

2. An isoxazole compound or pharmaceutically acceptable salt according to claim 1, in which R¹ and R² each independently stands for hydrogen, amino, lower alkylamino or di-lower alkylamino.

3. An isoxazole compound or pharmaceutically acceptable salt according to claim 1, in which X¹, X² and X³ each independently stands for hydrogen, halogen, lower alkyl or lower alkoxy.

4. An isoxazole compound or pharmaceutically acceptable salt according to claim 1 or 2, in which R⁴ stands for hydrogen.

5. An isoxazole compound or pharmaceutically acceptable salt according to claim 1, in which R⁵ stands for phenyl which is optionally substituted with 1 or 2 substituents selected from halogen and lower alkyl.

6. An isoxazole compound or pharmaceutically acceptable salt according to claim 5, in which R⁵ is phenyl, 2-halophenyl, 2,6-dihalophenyl, 2-lower alkylphenyl, 3-lower alkylphenyl or 2,5-di-lower alkylphenyl.

7. An isoxazole compound or pharmaceutically acceptable salt according to claim 1 or 2, in which Y stands for —CH₂— or —CH₂CH₂—.

8. An isoxazole compound selected from the group consisting of:
3-(3-methylphenyl)-5-(3-phenylpropionylamino)-4-(4-pyridyl)-isoxazole,
3-(3-methylphenyl)-5-[(2-methylphenyl) propionylamino]-4-(4-pyridyl)isoxazole,
5-[(3-chlorophenyl)propionylamino]-3-(2-fluoro-5-methyl-phenyl)-4-(4-pyridyl)isoxazole,
3-(4-fluoro-3-methylphenyl)-5-(phenylacetylamino)-4-(4-pyridyl)isoxazole,
5-[(2-chlorophenyl)acetylamino]-3-(4-fluoro-3-methylphenyl)-4-(4-pyridyl)isoxazole, and
3-(4-fluoro-3-methylphenyl)-5-(3-phenylpropionylamino)-4-(4-pyridyl)isoxazole,
or a pharmaceutically acceptable salt thereof.

9. A pharmaceutical composition which comprises an effective amount of the isoxazole compound or pharmaceutically acceptable salt according to claim 1 or 2, together with a non-toxic excipient.

10. A pharmaceutical composition which comprises an effective amount of the isoxazole compound or pharmaceutically acceptable salt according to claim 8, together with a non-toxic excipient.

* * * * *